US010849985B2

(12) United States Patent
Krizhanovsky et al.

(10) Patent No.: US 10,849,985 B2
(45) Date of Patent: Dec. 1, 2020

(54) METHOD OF TARGETING SENESCENT CELLS

(71) Applicant: Yeda Research and Development Co. Ltd., Rehovot (IL)

(72) Inventors: Valery Krizhanovsky, Rehovot (IL); Yossi Ovadya, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/573,550

(22) PCT Filed: May 19, 2016

(86) PCT No.: PCT/IL2016/050535
§ 371 (c)(1),
(2) Date: Nov. 13, 2017

(87) PCT Pub. No.: WO2016/185481
PCT Pub. Date: Nov. 24, 2016

(65) Prior Publication Data
US 2018/0117173 A1  May 3, 2018

Related U.S. Application Data

(60) Provisional application No. 62/164,025, filed on May 20, 2015.

(51) Int. Cl.
| | |
|---|---|
| *A61K 47/68* | (2017.01) |
| *A61P 35/00* | (2006.01) |
| *A61K 45/06* | (2006.01) |
| *C07K 16/18* | (2006.01) |
| *C12N 15/113* | (2010.01) |

(52) U.S. Cl.
CPC .......... *A61K 47/6843* (2017.08); *A61K 45/06* (2013.01); *A61K 47/6807* (2017.08); *A61K 47/6849* (2017.08); *A61P 35/00* (2018.01); *C07K 16/18* (2013.01); *C12N 15/1137* (2013.01); *C12N 2310/14* (2013.01); *C12N 2310/3513* (2013.01)

(58) Field of Classification Search
CPC ............... A61K 45/06; A61K 47/6843; A61K 47/6849; A61P 35/00; C07K 16/18; C12N 15/1137; C12N 15/1138
USPC ............ 435/6.1, 91.1, 91.31, 375, 455, 458; 514/1, 2, 44; 530/300, 350; 536/23.1, 536/24.5
See application file for complete search history.

(56) References Cited

U.S. PATENT DOCUMENTS

| | | | |
|---|---|---|---|
| 8,158,347 B2 | 4/2012 | Sharpless et al. | |
| 10,100,095 B2* | 10/2018 | Yoshimura | ........... A61K 31/437 |
| 2004/0152651 A1* | 8/2004 | Rana | .................... C12N 15/113 |
| | | | 514/44 A |
| 2017/0056421 A1* | 3/2017 | Zhou | ....................... C07K 1/00 |

FOREIGN PATENT DOCUMENTS

| | | |
|---|---|---|
| WO | WO 96/13610 | 5/1996 |
| WO | WO 2009/059425 | 5/2009 |
| WO | WO 2009/085216 | 7/2009 |
| WO | WO 2013/152038 | 10/2013 |
| WO | WO 2014/089124 | 6/2014 |
| WO | WO 2014/174511 | 10/2014 |
| WO | WO 2016/185481 | 11/2016 |

OTHER PUBLICATIONS

Weidle et al, Cancer Genomics & Proteomics, vol. 8, pp. 49-64 (Year: 2011).*
Schosserer et al, Frontiers in Oncology, vol. 6, Article 278, pp. 1-13. (Year: 2017).*
Childs et al, Nature Reviews, Drug Discovery, Advance Online Publication, Senescent cells: an emerging target for diseases and ageing, pp. 1-18. (Year: 2017).*
Spisek et al., Blood, vol. 109, No. 11, pp. 4839-4845. (Year: 2007).*
Communication Relating to the Results of the Partial International Search dated Aug. 18, 2016 From the International Searching Authority Re. Application No. PCT/IL2016/050535.
International Preliminary Report on Patentability dated Nov. 30, 2017 From the International Bureau of WIPO Re. Application No. PCT/IL2016/050535. (13 Pages).
International Search Report and the Written Opinion dated Nov. 17, 2016 From the International Searching Authority Re. Application No. PCT/IL2016/050535. (22 Pages).
Cabreiro et al. "Identification of Proteins Undergoing Expression Level Modifications in WI-38 SV40 Fibroblasts Overexpressing Methionine Sulfoxide Reductase A", Biochimie, XP022302862, 89(11): 1388-1395, Available Online May 24, 2007. Abstract, p. 1393, r-h Col.
Chan et al., "A Novel Hsp90 Inhibitor AT13387 Induces Senescence in EBV-Positive Nasopharyngeal Carcinoma Cells and Suppresses Tumor Formation", Molecular Cancer, XP021168133, 12(1): 128-1-128-15, Oct. 24, 2013. Abstract, Figs., p. 11, r-h Col., Para Conclusion.

(Continued)

*Primary Examiner* — Jane J Zara
(74) *Attorney, Agent, or Firm* — Mark S. Cohen; Pearl Cohen Zedek Latzer Baratz LLP

(57) ABSTRACT

A method of targeting a pharmaceutical agent to a senescent cell is disclosed. The method comprises administering the pharmaceutical agent to the subject, wherein said pharmaceutical agent is attached to an affinity moiety, said affinity moiety being capable of binding specifically to a polypeptide selected from the group consisting of HSP90B1, DNAJB4, PI4K2A, DBN1, PRKCSH, SPTBN1, NPM1, ITGA3 and a polypeptide set forth in Table 1. The targeting may be for therapeutics or diagnostics.

3 Claims, 6 Drawing Sheets
(6 of 6 Drawing Sheet(s) Filed in Color)
Specification includes a Sequence Listing.

(56) References Cited

OTHER PUBLICATIONS

Doran et al. "Aging Skeletal Muscle Shows a Drastic Increase in the Small Heat Shock Proteins AlphaB-Crystallin/HspB5 and cvHsp/HspB7", European Journal of Cell Biology, XP022257735, 86(10): 629-640, Sep. 19, 2007. Abstract, p. 635.

Garnacho et al. "A Fibrinogen-Derived Peptide Provides Intercellular Adhesion Molecule-a-Specific Targeting and Intraendothelial Transport of Polymer Nanocarriers in Human Cell Cultures and Mice", The Journal of Pharmacology and Experimental Therapeutics, 340(3): 638-647, 2012.

Naylor et al. "Senescent Cells: A Novel Therapeutic Target for Aging and Age-Related Diseases", Clinical Pharmacology and Therapeutics, XP002710105, 93(1): 105-116, Published Online Dec. 5, 2012. Abstract, p. 111.

Stolzing et al. "Age-Related Changes in Human Bone Marrow-Derived Mesenchymal Stem Cells: Consequences for Cell Therapies", Mechanisms of Ageing and Development, XP022472720, 129(3): 163-173, Available Online Dec. 17, 2007. Abstract, p. 167-168, 170, Fig.5.

Yoo et al. "Expression Profiles of Subtracted mRNAs During Cellular Senescence in Human Mesenchymal Stem Cells Derived From Bone Marrow", Experimental Gerontology, XP055291836, 48(5): 464-471, Available Online Mar. 4, 2013. Abstract, p. 467, 1-h Col., p. 469, Fig.4.

Childs, B. G., Gluscevic, M., Baker, D. J., Laberge, R. M., Marquess, D., Denenberg, J., & van Deursen, J. M. (2017). "Senescent cells: an emerging target for diseases of ageing." Nature reviews Drug discovery, 16(10), 718.

Hoter, A., El-Sabban, M., & Naim, H. (2018). "The HSP90 family: structure, regulation, function, and implications in health and disease." International Journal of Molecular Sciences, 19(9), 2560.

Lee, S., & Schmitt, C. A. (2019). "The dynamic nature of senescence in cancer." Nature Cell Biology, 21(1), 94. Abstract only.

Schosserer, M., Grillari, J., & Breitenbach, M. (2017). "The dual role of cellular senescence in developing tumors and their response to cancer therapy." Frontiers in Oncology, 7: 278.

Subbarao Sreedhar, A., Kalmár, É., Csermely, P., & Shen, Y. F. (2004). "Hsp90 isoforms: functions, expression and clinical importance." FEBS Letters, 562(1-3), 11-15.

Ullrich, S. J., Robinson, E. A., Law, L. W., Willingham, M., & Appella, E. (1986). "A mouse tumor-specific transplantation antigen is a heat shock-related protein." Proceedings of the National Academy of Sciences, 83(10), 3121-3125.

\* cited by examiner

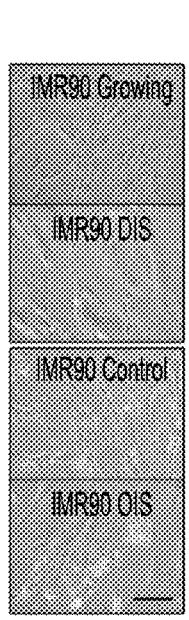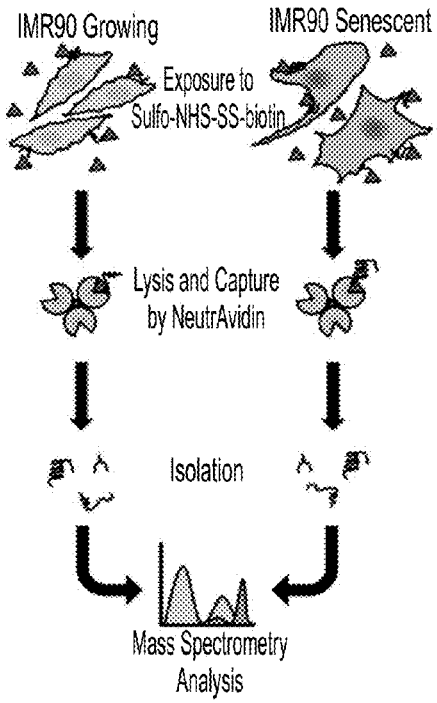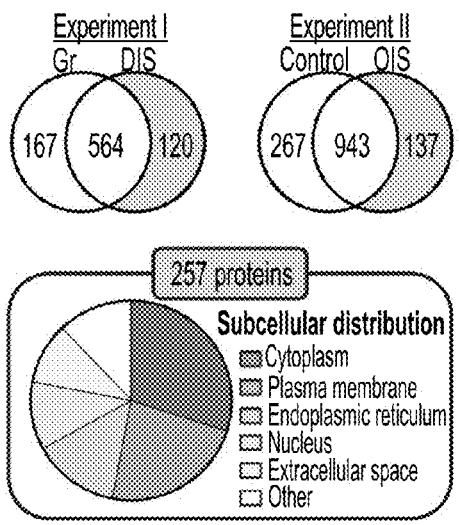
FIG. 1A   FIG. 1B   FIG. 1C
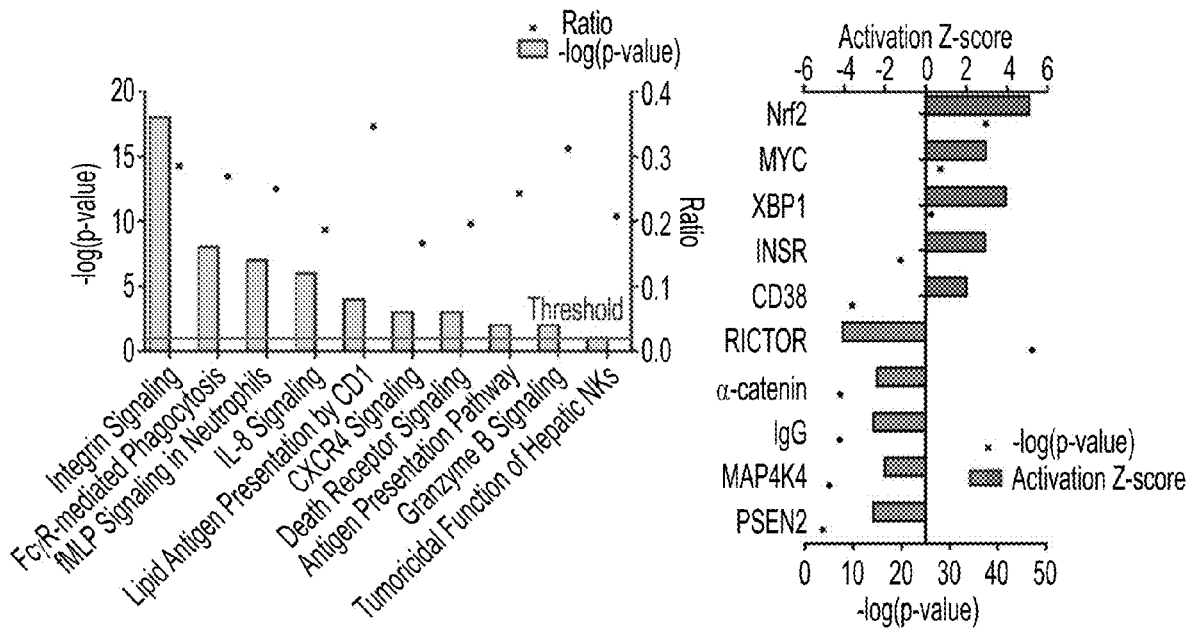
FIG. 1D   FIG. 1E

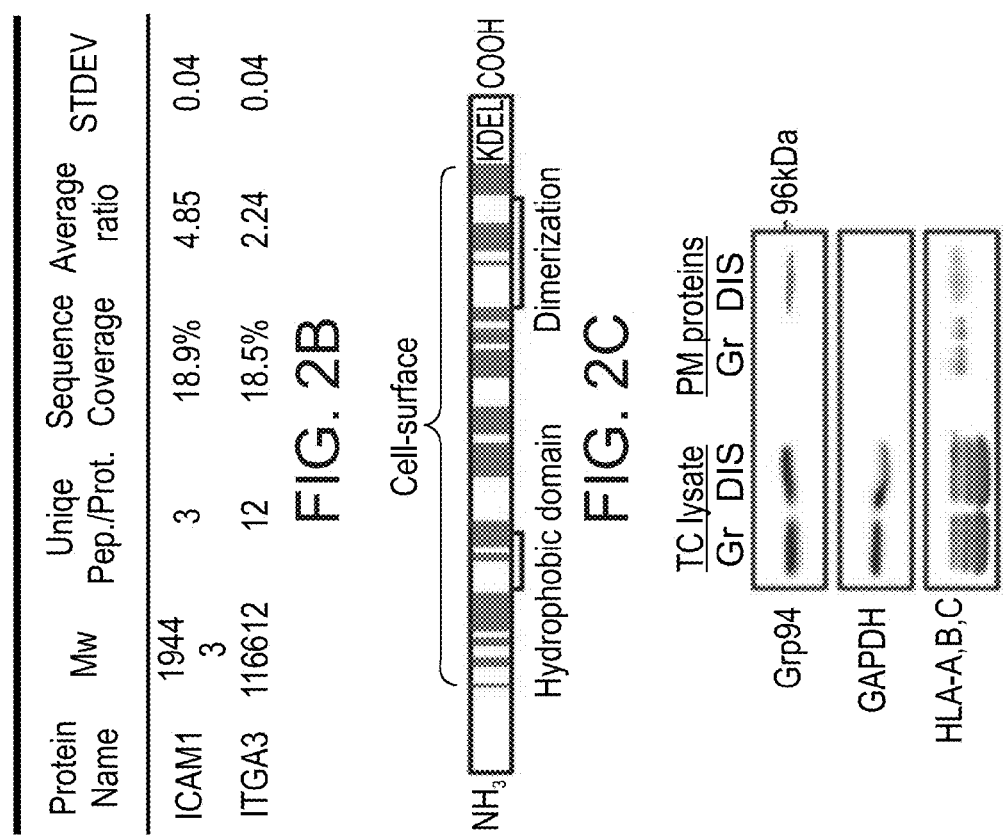
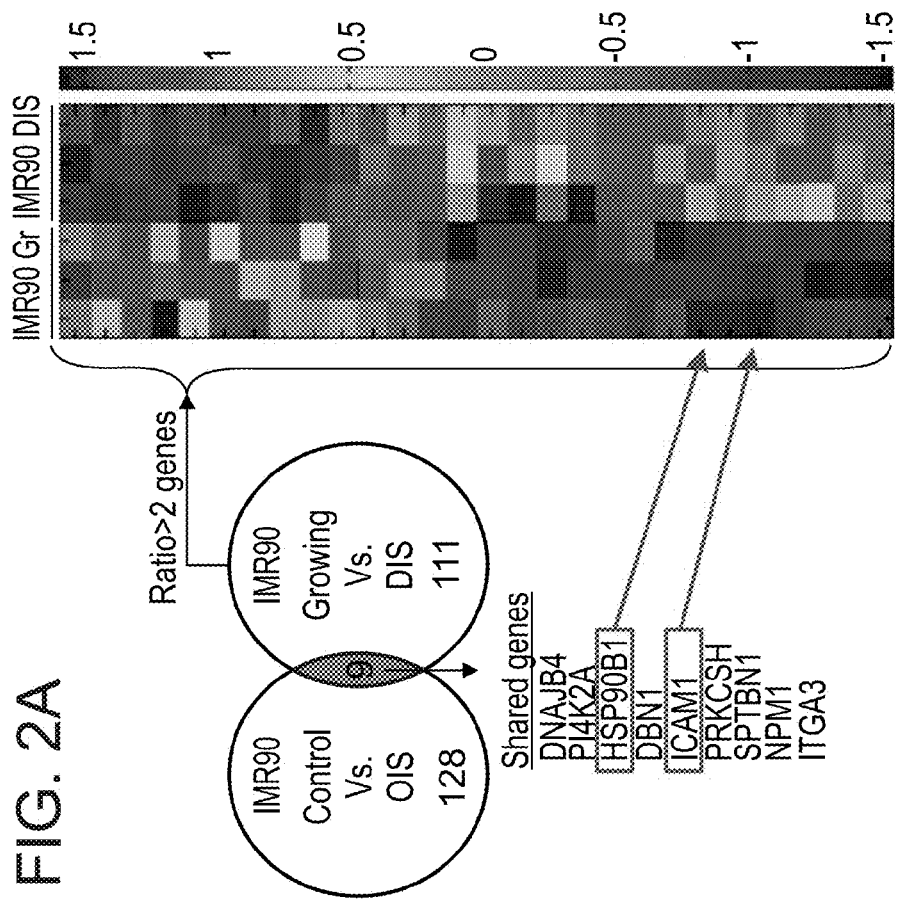
FIG. 2A
FIG. 2B
FIG. 2C
FIG. 2D

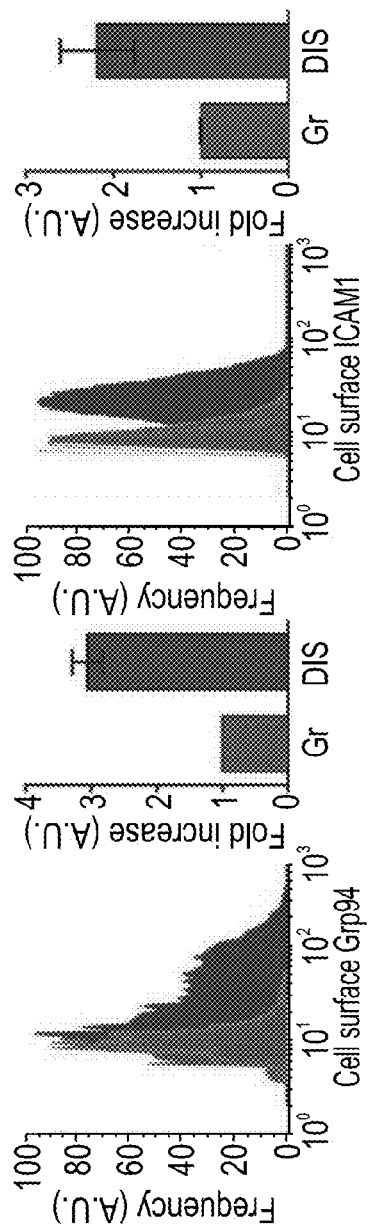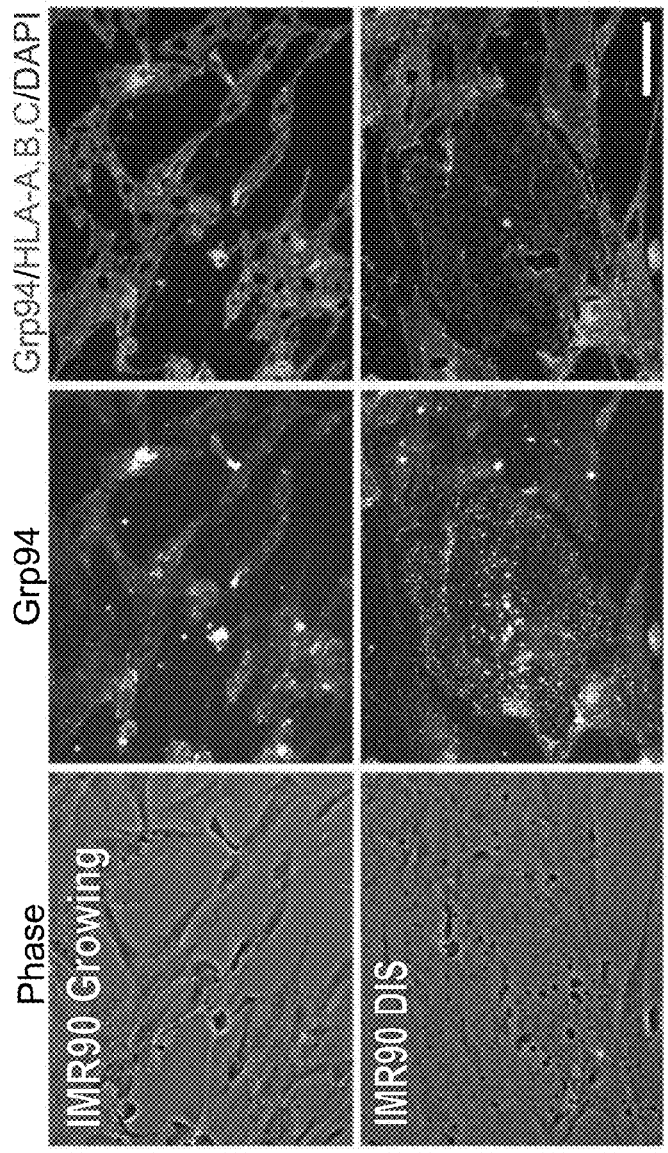

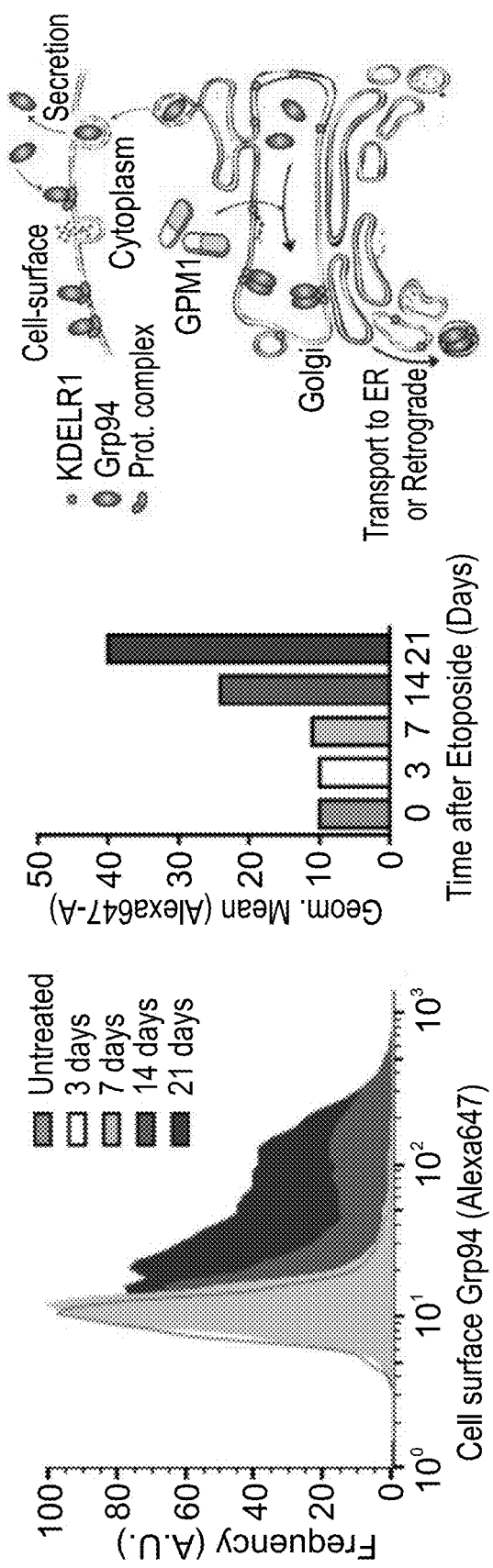
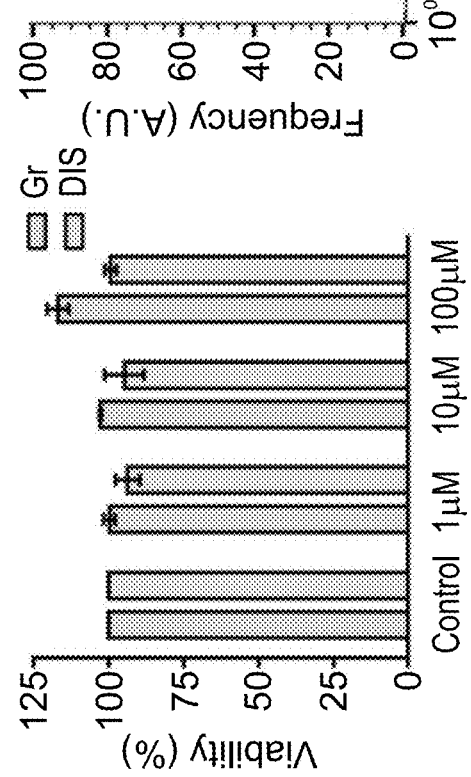

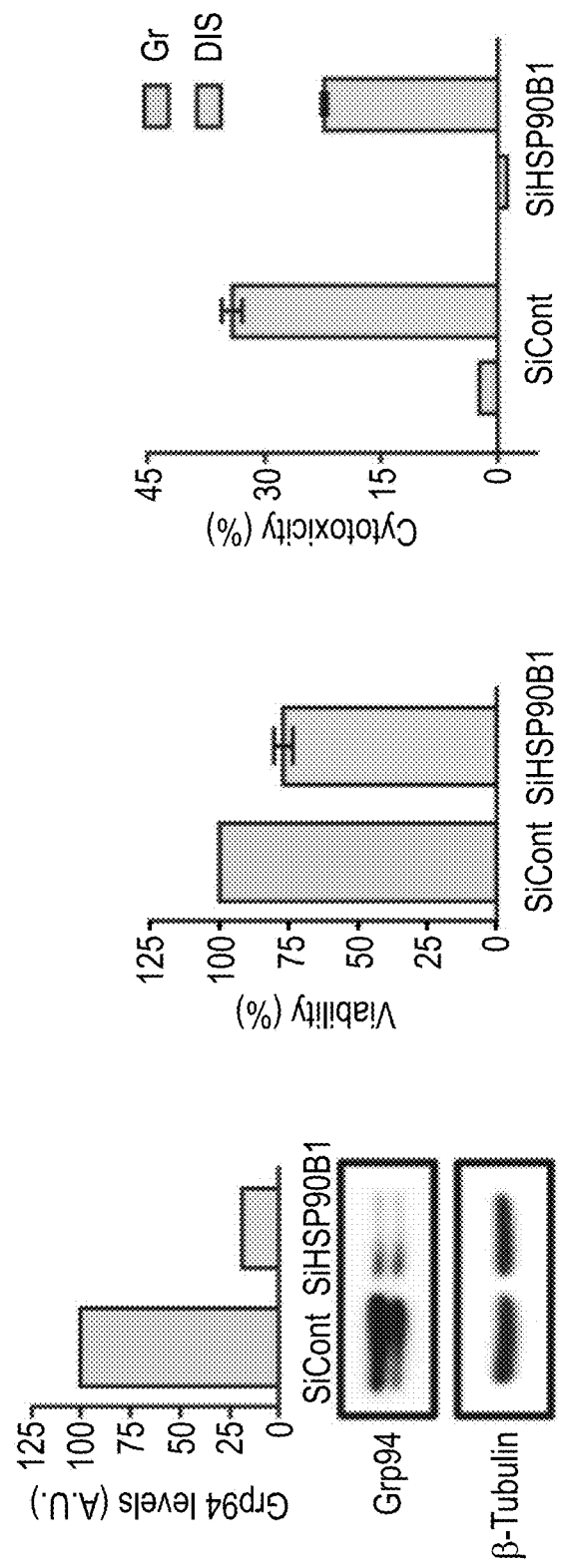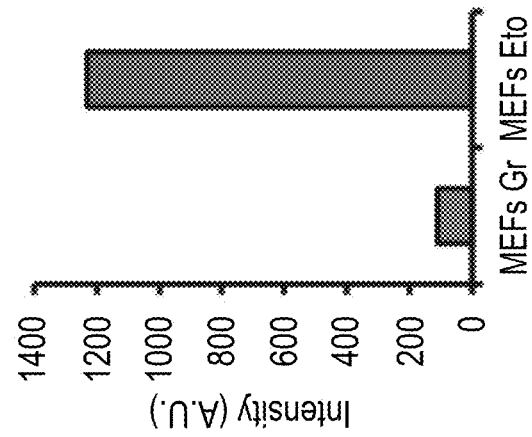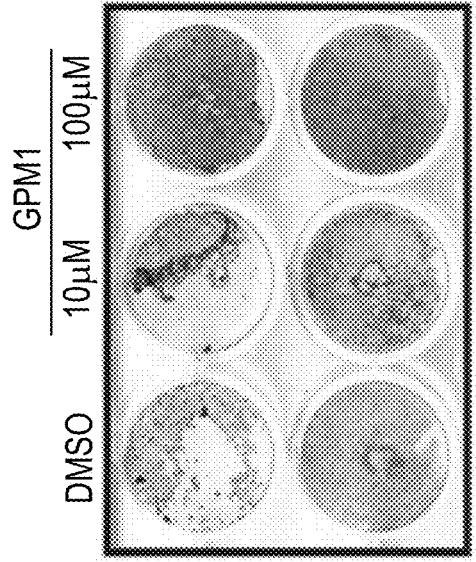
FIG. 4A FIG. 4B FIG. 4C FIG. 4D FIG. 4E ued States Patent US 10,849,985 B2

METHOD OF TARGETING SENESCENT CELLS

RELATED APPLICATIONS

This application is a National Phase of PCT Patent Application No. PCT/IL2016/050535 having International filing date of May 19, 2016 which claims the benefit of priority under 35 USC § 119(e) of U.S. Provisional Patent Application No. 62/164,025 filed on May 20, 2015. The contents of the above applications are all incorporated by reference as if fully set forth herein in their entirety.

SEQUENCE LISTING STATEMENT

The ASCII file, entitled 71478_ST25.txt, created on Mar. 19, 2019, comprising 199,000 bytes, submitted on Mar. 25, 2019 is incorporated herein by reference.

FIELD AND BACKGROUND OF THE INVENTION

The present invention, in some embodiments thereof, relates to methods of targeting senescent cells for treating and diagnosing diseases.

Cellular senescence, a stable form of cell cycle arrest, is a mechanism limiting the proliferative potential of cells. Senescence can be triggered in many cell types in response to diverse forms of cellular stress. It is a potent barrier to tumorigenesis and contributes to the cytotoxicity of certain anti-cancer agents. While senescence limits tumorigenesis and tissue damage in a cell autonomous manner, senescent cells induce inflammation, tissue ageing, tissue destruction and promote tumorigenesis and metastasis in a cell non-autonomous manner in the sites of their presence. Therefore, their elimination might lead to tumor prevention and inhibition of tissue ageing. Indeed, elimination of senescent cells was shown to slow down tissue ageing in an animal model (Baker et al., 2011).

Organisms may have developed elaborate mechanisms to eliminate senescent cells in order to avoid their deleterious effects on the microenvironment. However, their fate in tissue is not well characterized. On one hand, benign melanocytic nevi (moles) are highly enriched for senescent cells yet can exist in skin throughout a lifetime, implying that senescent cells can be stably incorporated into tissues. On the other hand, it has been previously shown that components of the innate immune system specifically recognize and eliminate senescent cells in vitro and target senescent cells in vivo leading to tumor regression and reversion of liver fibrosis (Krizhanovsky et al., 2008b; Sagiv et al., 2012; Xue et al., 2007). Therefore, senescent cells can turn over in vivo and the immune system contributes to this turnover. The effort that the immune system invests in recognition and elimination of senescent cells suggests, although not directly, that senescent cells are deleterious for the organism and their elimination is beneficial.

Background art includes WO2014/174511, WO2013/152038, WO2014/089124, and Garnacho et al., Journal of Pharmacology and Experimental Therapeutics, March 2012 vol. 340 no. 3 638-647.

SUMMARY OF THE INVENTION

According to an aspect of some embodiments of the present invention there is provided a method of targeting a pharmaceutical agent to a senescent cell in a subject comprising administering the pharmaceutical agent to the subject, wherein the pharmaceutical agent is attached to an affinity moiety, the affinity moiety being capable of binding specifically to a polypeptide selected from the group consisting of HSP90B1, DNAJB4, PI4K2A, DBN1, PRKCSH, SPTBN1, NPM1, ITGA3 and a polypeptide set forth in Table 1, thereby targeting the pharmaceutical agent to the senescent cell.

According to an aspect of some embodiments of the present invention there is provided a method of treating a disease associated with cell senescence in a subject in need thereof comprising administering to the agent a therapeutically effective amount of a cytotoxic agent attached to an affinity moiety, the affinity moiety being capable of binding specifically to a polypeptide selected from the group consisting of HSP90B1, DNAJB4, PI4K2A, DBN1, PRKCSH, SPTBN1, NPM1, ITGA3 and a polypeptide set forth in Table 1, thereby treating the disease.

According to an aspect of some embodiments of the present invention there is provided a particle having a senescent cell affinity moiety attached to an outer surface thereof, the senescent cell affinity moiety capable of specifically binding a polypeptide selected from the group consisting of HSP90B1, DNAJB4, PI4K2A, DBN1, PRKCSH, SPTBN1, NPM1, ITGA3 and a polypeptide set forth in Table 1.

According to an aspect of some embodiments of the present invention there is provided a composition of matter comprising an affinity moiety attached to a therapeutic agent, wherein the affinity moiety specifically binds to a polypeptide selected from the group consisting of HSP90B1, DNAJB4, PI4K2A, DBN1, PRKCSH, SPTBN1, NPM1, ITGA3 and a polypeptide set forth in Table 1.

According to an aspect of some embodiments of the present invention there is provided a pharmaceutical composition comprising the composition of matter or particle described herein as the active agent and a pharmaceutically acceptable carrier.

According to an aspect of some embodiments of the present invention there is provided a method of diagnosing a disease associated with cell senescence in a subject comprising analyzing the amount of at least one polypeptide selected from the group consisting of HSP90B1, DNAJB4, PI4K2A, DBN1, PRKCSH, SPTBN1, NPM1, ITGA3 and a polypeptide set forth in Table 1 on the membrane of cells of the subject, wherein a level of the at least one polypeptide above a predetermined amount is indicative of the disease.

According to an aspect of some embodiments of the present invention there is provided a method of identifying senescent cells in a cell population comprising analyzing the amount of at least one polypeptide selected from the group consisting of HSP90B1, DNAJB4, PI4K2A, DBN1, PRKCSH, SPTBN1, NPM1, ITGA3 and a polypeptide set forth in Table 1 on the membrane of the cells of the cell population, wherein a level of the at least one polypeptide above a predetermined amount is indicative of senescent cells.

According to an aspect of some embodiments of the present invention there is provided a composition of matter comprising senescent cells, wherein a polypeptide of the cells is attached to an affinity moiety, the polypeptide being selected from the group consisting of HSP90B1, DNAJB4, PI4K2A, DBN1, PRKCSH, SPTBN1, NPM1, ITGA3 and a polypeptide set forth in Table 1.

According to an aspect of some embodiments of the present invention there is provided a method of eliciting or boosting an immune response to a senescent cell in a subject comprising administering to the subject a pharmaceutical composition comprising at least one polypeptide or a polynucleotide encoding same selected from the group consisting of HSP90B1, DBN1, PRKCSH, SPTBN1, NPM1 and a polypeptide set forth in Table 1, wherein the composition does not comprise senescent cells or membranes thereof, thereby eliciting or boosting the immune response to the senescent cell.

According to an aspect of some embodiments of the present invention there is provided a vaccine comprising at least one polypeptide or a polynucleotide encoding same as an active agent, the polypeptide being selected from the group consisting of HSP90B 1, DBN1, PRKCSH, SPTBN1, NPM1, an adjuvant, wherein the vaccine does not comprise senescent cells or membranes thereof and an immunologically acceptable carrier.

According to an aspect of some embodiments of the present invention there is provided a vaccine comprising cells expressing a heterogeneous polypeptide, as an active agent and an immunologically acceptable carrier, the polypeptide being selected from the group consisting of HSP90B1, DBN1, PRKCSH, SPTBN1, NPM1.

According to some embodiments of the invention, the pharmaceutical agent is a therapeutic agent.

According to some embodiments of the invention, the therapeutic agent is a cytotoxic agent.

According to some embodiments of the invention, the pharmaceutical agent is a diagnostic agent.

According to some embodiments of the invention, the cytotoxic agent is directly attached to the affinity moiety.

According to some embodiments of the invention, the cytotoxic agent is indirectly attached to the affinity moiety.

According to some embodiments of the invention, the cytotoxic agent is comprised in a particle.

According to some embodiments of the invention, the affinity moiety is attached to the outer surface of the particle.

According to some embodiments of the invention, the cytotoxic agent comprises a polynucleotide agent.

According to some embodiments of the invention, the cytotoxic agent comprises an RNA silencing agent.

According to some embodiments of the invention, the cytotoxic agent down-regulates an activity and/or an amount of an apoptosis related polypeptide.

According to some embodiments of the invention, the apoptosis related polypeptide is selected from the group consisting of Bcl-xL, Bcl-w and p21.

According to some embodiments of the invention, the cytotoxic agent is selected from the group consisting of ABT-737, ABT-263, Gossypol, AT-101, TW-37 and Obatoclax.

According to some embodiments of the invention, the affinity moiety is selected from the group consisting or an antibody, an aptamer and a peptide.

According to some embodiments of the invention, the polypeptide is HSP90B1.

According to some embodiments of the invention, the disease is a fibrotic disease or an inflammatory disease.

According to some embodiments of the invention, the inflammatory disease is cancer.

According to some embodiments of the invention, the method further comprises administering to the subject at least one agent selected from the group consisting of a sebum-regulating agent, an antibacterial and/or antifungal agent, a keratolytic agent and/or keratoregulating agent, an astringent, an anti-inflammatory and/or anti-irritant, an antioxidant and/or free-radical scavenger, a cicatrizing agent, an anti-aging agent and a moisturizing agent.

According to some embodiments of the invention, the at least one agent is an anti-aging agent.

According to some embodiments of the invention, the affinity moiety is an antibody or an aptamer.

According to some embodiments of the invention, the particle is attached to or encapsulating a therapeutic agent or a diagnostic agent.

According to some embodiments of the invention, the therapeutic agent comprises a cytotoxic moiety.

According to some embodiments of the invention, the cytotoxic moiety comprises a polynucleotide agent.

According to some embodiments of the invention, the polynucleotide agent comprises an RNA silencing agent.

According to some embodiments of the invention, the cytotoxic agent down-regulates an activity and/or an amount of an apoptosis related polypeptide.

According to some embodiments of the invention, the apoptosis related polypeptide is selected from the group consisting of Bcl-xL, Bcl-w and p21.

According to some embodiments of the invention, the pharmaceutical composition is formulated for topical administration.

According to some embodiments of the invention, the pharmaceutical composition further comprises at least one agent selected from the group consisting of a sebum-regulating agent, an antibacterial and/or antifungal agent, a keratolytic agent and/or keratoregulating agent, an astringent, an anti-inflammatory and/or anti-irritant, an antioxidant and/or free-radical scavenger, a cicatrizing agent, an anti-aging agent and a moisturizing agent.

According to some embodiments of the invention, the at least one agent is an anti-aging agent.

According to some embodiments of the invention, the senescent cells are lysed cells.

According to some embodiments of the invention, the senescent cells are non-lysed cells.

According to some embodiments of the invention, the disease is a fibrotic disease or an inflammatory disease.

According to some embodiments of the invention, the inflammatory disease is cancer.

According to some embodiments of the invention, the identifying is effected in vivo.

According to some embodiments of the invention, the identifying is effected ex vivo.

According to some embodiments of the invention, the identifying is effected in vitro.

According to some embodiments of the invention, the at least one polypeptide is HSP90B 1.

According to some embodiments of the invention, the analyzing is effected using an antibody that selectively binds the at least one polypeptide.

According to some embodiments of the invention, the antibody is attached to a detectable moiety.

According to some embodiments of the invention, the vaccine further comprises an adjuvant.

According to some embodiments of the invention, the polypeptide is expressed on a cell surface.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 5A:
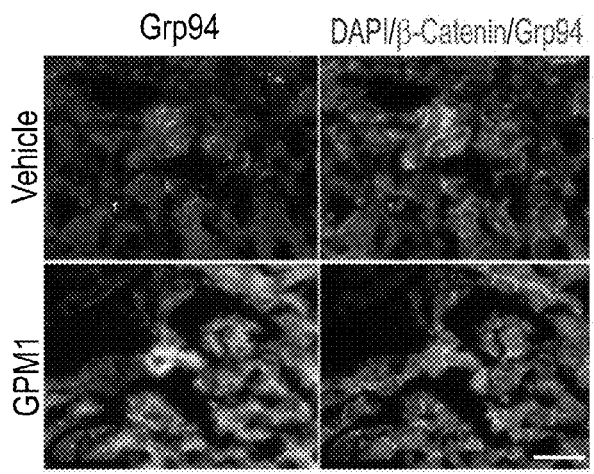

FIGS. 1A-E. Isolation and identification of senescence-specific membrane proteins. (A) Images of senescent IMR90 cells 9 days after Etoposide (DIS), and senescent IMR90 cells 9 days after infection with H-Ras (OIS). Scale bar-100 µm. (B) Schematic description of isolation and identification of membrane proteins. (C-E) Integrative analysis of senescence restricted cell surface proteins. (C) Distribution of identified proteins in the two experiments (each experiment in at least 3 repeats). The upper part shows distribution of proteins exclusively detected in each senescent cell type-DIS and OIS. The lower part shows primary sub-cellular location of cell-surface proteome of senescent cells combined from both experiments. (D) Immune-related canonical pathways attributed to the identified proteins. (E) Candidate upstream regulators potentially responsible for the changes observed in identified proteins as revealed by analysis using Ingenuity.

FIGS. 2A-I. Grp94 is upregulated on the surface of senescent cells. (A) Intersection of senescence specific cell-surface proteins from DIS and OIS experiments, and the list of the nine shared proteins. (B) Main features obtained from MS analysis regarding ICAM1, ITGA3, and Grp94. (C) Location of unique peptides detected in MS analysis on the sequence of Grp94 protein (in blue). (D) Western blot analysis of Grp94, GAPDH and HLA-A,B,C from Qiagen surface-proteins isolation kit comparing to total cell-lysate. (E) Flow cytometry histogram for the frequency of cell-surface Grp94 on live IMR90 cells. (F) Quantitative analysis of cell-surface Grp94 on live IMR90 cells. (G) Flow cytometry histogram for the frequency of cell-surface ICAM1 on live IMR90 cells. (H) Quantitative analysis of cell-surface ICAM1 on live IMR90 cells. (I) Immunofluorescent staining of live IMR90 cells for Grp94 (Alexa-647) against cell-surface marker HLA-A,B,C (Alexa-488). Scale bar-100 µm.

FIGS. 3A-F. Grp94 translocates to cell-surface of senescent cells. (A) Flow cytometry histogram for the frequency cell-surface Grp94 of live IMR90 cells 0, 3, 7, 14, or 21 days after etoposide treatment. (B) Quantitative analysis of cell-surface Grp94 on live IMR90 cells 0, 3, 7, 14, or 21 days after etoposide treatment. (C) Scheme describing the mechanism of GPM1-mediated blockage of Grp94 translocation to cell-surface. (D) PrestoBlue viability assay for IMR90 growing or senescent Etoposide-treated cells after 24 hrs treatment with 1, 10, or 100 µM GPM1. GPM1 does not affect cell viability. (E) Flow cytometry histogram for the frequency of cell-surface Grp94 of live senescent etoposide-treated IMR90 cells after 24 hrs treatment with 10 or 100 µM GPM1. (F) Quantitative analysis of cell-surface Grp94 on live senescent etoposide-treated IMR90 cells after 24 hrs treatment with 10 or 100 µM GPM1.

FIGS. 4A-E. Extracellular Grp94 on senescent cells mediate cytotoxicity of innate components in-vitro. (A) Western blot analysis for Grp94/β-Tubulin in Etoposide-treated IMR90 cells 4 days after transfection with siControl or siHSP90B1 (HSP90B1 is a gene coding for Grp94). (B) PrestoBlue viability assay for Etoposide-treated IMR90 4 days after Transfection with siControl or siHSP90B1. (C) Cytotoxicity of NK92 cells in cultures of IMR90 cells treated with siControl or siHSP90B1. NK92 were added for 1 hour at a ratio of 1:3 (D) Crystal Violet staining for IMR90 cells after co-culturing with MM6 monocytes in the presence of GPM1. (E) Quantitative analysis of cell-surface Grp94 of Mouse embryonic fibroblasts (MEFs) 14 days after Etoposide treatment compared to growing MEFs.

FIGS. 5A-D illustrate that GPM1 administration prevents immune surveillance of senescent hepatic stellate cells in vivo. Mice treated with 12 intraperitoneal (i.p.) injections of $CCl_4$ (1 ml/kg, twice a week) to induce liver fibrosis were subsequently subjected to 12 daily i.p. injections of Vehicle or GPM1 (30 mg/kg/day), n=5. (A) IF staining on frozen sections of fibrotic livers treated with Vehicle or GPM1, for Grp94 (orange) and cell surface marker β-Catenin (green). Scale bar-20 µm. (B) SA-β-Gal staining (upper panel), H&E staining (middle panel), and Sirius Red staining (lower panel) of frozen sections from control liver, fibrotic liver, and fibrotic livers after 12 days of Vehicle or GPM1. Scale bar of SA-β-Gal images-100 µm. Scale bar of Sirius Red images-200 µm (C) Quantification of SA-β-Gal positive cells in the livers. Values are means+standard error of the mean (SEM). (D) Quantification of fibrosis based on Sirius Red staining. Values are means+standard error of the mean (SEM). Fibrotic area in GPM1 treated mice was compared to the one of Vehicle treated mice using Student's t test (***$p<0.01$).

DESCRIPTION OF SPECIFIC EMBODIMENTS OF THE INVENTION

The present invention, in some embodiments thereof, relates to methods of targeting senescent cells for treating and diagnosing diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cellular senescence, a stable irreversible cell-cycle arrest, prevents propagation of damaged cells in the organism. Senescent cells can be found in fibrotic or inflammatory diseases of skin, liver, lung, pancreas, prostate, as well as in articular cartilage, atherosclerotic plaques and other age-related diseases. Moreover, senescent cells were shown to accumulate in normal tissues, especially skin, with age and suggested to contribute to tissue ageing.

The immune system recognizes and eliminates senescent cells to facilitate their removal from tissues. In order to unravel the molecular mechanisms behind this process, the present inventors evaluated the cell surface proteome specific to human senescent fibroblasts. Nine proteins were identified that were expressed exclusively on the surface of senescent cells (FIG. 2A). One of these proteins is glucose regulated protein 94 (Grp94), an ER chaperone which translocates to cell surface, and acts there as a potent regulator of the immune response. Cell-surface Grp94 was shown to accumulate in senescent cells in a time-dependent manner (FIG. 3A). This accumulation was inhibited by GPM1, a small-molecule which specifically promote Grp94 dimerization and retention in the ER.

Whilst reducing the present invention to practice, the present inventors validated the presence of the full-size Grp94 protein on the surface of senescent cells (FIG. 2D), and evaluated its functional role in the interaction with immune cells. The present inventors showed that downregulation of cell-surface Grp94 decreases NK-cell mediated cytotoxicity toward senescent cells. In a similar manner, GPM1 has decreased susceptibility of senescent cells for elimination by monocytes.

The present inventors propose that the identified surface proteins specific for senescent cells may provide a target not only for the immune system, but also for delivering specific agents to these cells for their labeling or elimination. The elimination of senescent cells might be valuable strategy to prevent cancer, treat cancer and treat variety of age-related diseases where senescent cells are present.

Thus, according to a first aspect of the present invention there is provided a method of targeting an agent to a senescent cell in a subject comprising administering the agent to the subject, wherein the agent is attached to an affinity moiety, the affinity moiety being capable of binding specifically to a polypeptide selected from the group consisting of HSP90B1, DNAJB4, PI4K2A, DBN1, PRKCSH, SPTBN1, NPM1, ITGA3 and a polypeptide set forth in Table 1, thereby targeting the agent to the senescent cell.

The term "senescent cells" refers to cells that exhibit cell cycle arrest, generally during the G1 transition of the cell cycle or in few cases in G2, elicited by replicative exhaustion due to telomere attrition or in response to stresses such as DNA damage, chemotherapeutic drugs, or aberrant expression of oncogenes.

According to a particular embodiment, the senescent cells are characterized by at least one or more of the following characteristics:
1. activation of the p53/p21CIP1 and/or pRb/p16INK4A tumor suppressor pathways;
2. cells whose proliferation is irreversibly arrested;
3. shortening of telomere size;
4. expression of senescent-associated beta-galactosidase activity;
5. Specific chromatin modification;
6. Specific secretome;
7. Increase in reactive oxygen species and altered overall mitochondrial activity.

Irreversible cell cycle arrest may be assessed by FACS or BrdU incorporation assay. Shortening of telomere size may be characterized by evaluating the mean terminal restriction fragment (TRF) length for example by Southern blot analysis. Other methods of ascertaining whether a cell is senescent are described in U.S. Patent No. 20140056860, the contents of which are incorporated herein by reference.

Agents which may be targeted to the senescent cells include but are not limited to therapeutic agents and diagnostic agents.

Exemplary therapeutic agents include nucleic acid, polypeptides e.g. antibodies, anticancer agent (e.g., chemotherapy, radioisotopes, immunotherapy), antibiotic, enzyme, antioxidant, lipid intake inhibitor, hormone, anti-inflammatory, steroid, vasodilator, angiotensin converting enzyme inhibitor, angiotensin receptor antagonist, inhibitor for smooth muscle cell growth and migration, platelet aggregation inhibitor, anticoagulant, inhibitor for release of chemical mediator, promoter or inhibitor for endothelial cell growth, aldose reductase inhibitor, inhibitor for mesangium cell growth, lipoxygenase inhibitor, immunosuppressive, immunostimulant, antiviral agent, Maillard reaction suppressor, amyloidosis inhibitor, nitric oxide synthetic inhibitor, AGEs (Advanced glycation end-products) inhibitor, radical scavenger, protein, peptide; glycosaminoglycan and derivatives thereof; and oligosaccharide, polysaccharide, and derivatives thereof.

According to a particular embodiment, the pharmaceutical agent is a cytotoxic agent.

As used herein, the term "cytotoxic agent" refers to refers to a substance that inhibits or prevents the function of cells and/or causes destruction of cells. The term is intended to include radioactive isotopes (e.g., $^{211}At$, $^{131}I$, $^{125}I$, $^{32}P$, $^{35}S$ and radioactive isotopes of Lu, including $^{177}Lu$, $^{86}Y$, $^{90}Y$, $^{111}In$, $^{177}Lu$, $^{225}Ac$, $^{212}Bi$, $^{213}Bi$, $^{66}Ga$, $^{67}Ga$, $^{68}Ga$, $^{64}Cu$, $^{67}CU$, $^{71}As$, $^{72}As$, $^{76}As$, $^{77}As$, $^{65}Zn$, $^{48}V$, $^{203}Pb$, $^{209}Pb$, $^{212}Pb$, $^{166}Ho$, $^{149}Pm$, $^{153}Sm$, $^{201}Tl$, $^{188}Re$, $^{186}Re$ and $^{99m}Tc$), anti cancer agents as otherwise described herein, including chemotherapeutic (anticancer drugs e.g. methotrexate, adriamicin, vinca alkaloids (vincristine, vinblastine, etoposide), taxol, doxoruicin, cisplatin, 5-fluorouridine, melphalan, ethidium bromide, mitomycin C, chlorambucil, daunorubicin and other intercalating agents, enzymes and fragments thereof such as nucleolytic enzymes, antibiotics, therapeutic RNA molecules (e.g., siRNA, antisense oligonucleotides, microRNA, ribozymes, RNA decoys, aptamers), DNA-zymes, antibodies, proteins and polynucleotides encoding same, and toxins such as small molecule toxins or enzymatically active toxins of bacterial, fungal, plant or animal origin, such as pokeweed antiviral protein (PAP), ricin toxin A, abrin, gelonin, saporin, cholera toxin A, diphtheria toxin, Pseudomonas exotoxin, and alpha-sarcin, including fragments and/or variants thereof.

As mentioned, the present invention contemplates the use of RNA silencing agents as pharmaceutical agents and more specifically as cytotoxic agents. The RNA silencing agents may be directed against anti-apoptotic proteins including but not limited to Bcl-xL, Bcl-w and/or p21. Other targets for RNA silencing are described in WO2013152038 and WO2014089124, the contents of which are incorporated herein by reference.

The term "Bcl-xL" refers to the human protein also known as B-cell lymphoma-extra large, having a sequence as set forth in SEQ ID NO: 1 and homologs and orthologs thereof. The cDNA sequence of human Bcl-xL is set forth in SEQ ID NO: 2.

The term "Bcl-w" refers to the human protein also known as Bcl-2-like protein 2, having a sequence as set forth in SEQ ID NO: 3 and homologs and orthologs thereof. The cDNA sequence of human Bcl-w is set forth in SEQ ID NO: 4.

The term "p21" also known as "cyclin-dependent kinase inhibitor 1" refers to the human protein having a sequence as set forth in SEQ ID NO: 5 and homologs and orthologs thereof. The cDNA sequence of human p21 is set forth in SEQ ID NO: 6.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433 and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [*Genes&Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

It will be appreciated that more than one siRNA agent may be used to down-regulate a target gene. Thus, for example, the present invention contemplates use of at least two siRNAs that target Bcl-xL, at least three siRNAs that target Bcl-xL, or even at least four siRNAs that target Bcl-xL, each targeting a different sequence in the Bcl-xL gene. Further, the present invention contemplates use of at least two siRNAs that target Bcl-w, at least three siRNAs that target Bcl-w, or even at least four siRNAs that target Bcl-w, each targeting a different sequence in the Bcl-w gene. Further, the present invention contemplates use of at least two siRNAs that target p21, at least three siRNAs that target p21, or even at least four siRNAs that target p21, each targeting a different sequence in the p21 gene.

The strands of a double-stranded interfering RNA (e.g., a siRNA) may be connected to form a hairpin or stem-loop structure (e.g., a shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 7; Brummelkamp, T. R. et al. (2002) Science 296: 550) and 5'-UUUGUGUAG-3' (SEQ ID NO: 8; Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to a miRNA, rather than triggering RNA degradation.

A suitable siRNA capable of downregulating Bcl-xL can be the siRNA of SEQ ID NO: 9, 10 or 11. A suitable siRNA capable of downregulating Bcl-w can be the siRNA of SEQ ID NO: 12, 13 or 14. A suitable siRNA capable of downregulating p21 can be the siRNA of SEQ ID NO: 15, 16 or 17.

It will be appreciated that the RNA silencing agent of the present invention need not be limited to those molecules containing only RNA, but further encompasses chemically-modified nucleotides and non-nucleotides.

Other cytotoxic agents contemplated by the present invention are polynucleotides that encode pro-apoptotic proteins. Non-limiting examples of pro-apoptotic genes include caspases, Bik, Puma, Bim, Bax, Bak, Bid, Bad, Bmf, Noxa, and Hrk.

The term "caspase" refers to proteases that play essential roles in apoptosis (programmed cell death) and necrosis. At least 12 caspases have been identified in humans. There are two types of apoptotic caspases: initiator (apical) caspases and effector (executioner) caspases. Initiator caspases (e.g., CASP2 (Genbank Accession: NM001224.4), CASP8 (Genbank Accession: NM001080124.1), CASP9 (Genbank Accession: NM001229.3), and CASP10 (Genbank Accession: NM001206524.1)) cleave inactive pro-forms of effector caspases, thereby activating them. Effector caspases (e.g., CASP3 (Genbank Accession: NM004346.3), CASP6 (Genbank Accession: NM001226.3), CASP7 (Genbank Accession: NM001227.3)) in turn cleave other protein substrates within the cell, to trigger the apoptotic process. The initiation of this cascade reaction is regulated by caspase inhibitors.

Polynucleotide agents (e.g. encoding pro-apoptotic polypeptides or encoding an RNA silencing agent targeted against anti-apoptotic polypeptides) are typically administered as part of an expression construct. In this case, the polynucleotide agent is ligated in a nucleic acid construct under the control of a cis-acting regulatory element (e.g. promoter) capable of directing an expression of the cytotoxic agent in a constitutive or inducible manner. An exemplary promoter which is active in senescent cells is the p16 promoter—see for example U.S. Patent No. 20150064137, the contents of which are incorporated herein by reference.

The nucleic acid agent may be delivered using an appropriate gene delivery vehicle/method (transfection, transduction, etc.). Optionally an appropriate expression system is used. Examples of suitable constructs include, but are not limited to, pcDNA3, pcDNA3.1 (±), pGL3, PzeoSV2 (±), pDisplay, pEF/myc/cyto, pCMV/myc/cyto each of which is commercially available from Invitrogen Co. (www(dot) invitrogen(dot)com).

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpes-viral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

Double stranded RNA may be synthesized by adding two opposing promoters to the ends of the gene segments, wherein one promoter is placed immediately 5' to the gene and the opposing promoter is placed immediately 3' to the gene segment. The dsRNA may then be transcribed with the appropriate polymerase.

Other cytotoxic agents known to down-regulate anti-apoptotic proteins are also contemplated by the present inventors—these include for example ABT-737, ABT-263, Gossypol, AT-101, TW-37 and Obatoclax.

According to another embodiment, the pharmaceutical agent is a diagnostic agent.

Exemplary diagnostic drugs include in vivo diagnostics such as an X ray contrast medium, a diagnostic agent for ultrasound, an isotope-labeled agent for diagnosis by nuclear medicine, and an agent for diagnosis by nuclear magnetic resonance.

As mentioned, the pharmaceutical agents of this aspect of the present invention are attached either directly or indirectly to an affinity moiety.

The affinity moiety may comprise a chemical (non-peptide) molecule, an aptamer, a peptide or an antibody (e.g. antibody-derived epitope binding domain) which is capable of specifically binding to one of the following proteins:

HSP90B1, also referred to herein as Grp94, Refseq no: NM_003299.2, (SEQ ID NO: 18), DNAJB4 Refseq no: NM_007034.3 (SEQ ID NO: 19), PI4K2A Refseq no: NM_018425.3 (SEQ ID NO: 20), DBN1 Refseq no: NM_004395.3 or NM_080881.2 (SEQ ID NOs: 21), PRKCSH NM_001001329.2 or NM_001289102.1 (SEQ ID NO: 22), SPTBN1 Refseq no: NM_178313.2 (SEQ ID NO: 23), NPM1 Refseq no: NM_001037738.2 (SEQ ID NO: 24), ITGA3 NM_002204.2 (SEQ ID NO: 25) and any of the polypeptides listed in Table 1 herein below.

For any of the aspects of the present invention, the polypeptide may be selected from the group consisting of HSP90B1, also referred to herein as Grp94, Refseq no: NM_003299.2, (SEQ ID NO: 18), DNAJB4 Refseq no: NM_007034.3 (SEQ ID NO: 19), PI4K2A Refseq no: NM_018425.3 (SEQ ID NO: 20), DBN1 Refseq no: NM_004395.3 or NM_080881.2 (SEQ ID NOs: 21), PRKCSH NM_001001329.2 or NM_001289102.1 (SEQ ID NO: 22), SPTBN1 Refseq no: NM_178313.2 (SEQ ID NO: 23), NPM1 Refseq no: NM_001037738.2 (SEQ ID NO: 24), ITGA3 NM_002204.2 (SEQ ID NO: 25).

For any of the aspects of the present invention, the polypeptide may be selected from the group consisting of HSP90B1, also referred to herein as Grp94, Refseq no: NM_003299.2, (SEQ ID NO: 18), DBN1 Refseq no: NM_004395.3 or NM_080881.2 (SEQ ID NOs: 21), PRKCSH NM_001001329.2 or NM_001289102.1 (SEQ ID NO: 22), SPTBN1 Refseq no: NM_178313.2 (SEQ ID NO: 23) and NPM1 Refseq no: NM_001037738.2 (SEQ ID NO: 24).

For any of the aspects of the present invention, the polypeptide may be HSP90B1, also referred to herein as Grp94, Refseq no: NM_003299.2, (SEQ ID NO: 18).

In one embodiment binding or specifically binding means a binding affinity (KD) of $10^{-8}$ mol/l or less, preferably $10^{-9}$ M to $10^{-13}$ mol/l.

In one embodiment, the affinity moiety binds to one of the above proteins with at least 5 fold higher affinity, 10 fold higher affinity or even 20 fold higher affinity than to a non-related protein.

The term "antibody" as used in this invention includes intact molecules as well as functional fragments thereof.

As used herein, the phrase "antibody fragment" refers to a functional fragment of an antibody (such as Fab, F(ab')2, Fv, scFv, dsFv, or single domain molecules such as VH and VL) that is capable of binding to an epitope of an antigen.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as a Fv, a single chain Fv (scFv), a disulfide-stabilized Fv (dsFv), an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Antibodies directed against any of the proteins HSP90B1, DNAJB4, PI4K2A, DBN1, PRKCSH, SPTBN1, NPM1, ITGA3 and those listed in Table 1 are commercially available from Pierce (e.g. anti-Grp94; PA5-24824).

As mentioned, the affinity moiety of this aspect of the present invention may also be an aptamer.

As used herein, the term "aptamer" refers to a nucleic acid that specifically binds to a target, such as a protein, through interactions other than Watson-Crick base pairing. In a particular embodiment, the aptamer specifically binds to one or more targets (e.g., a protein or protein complex) to the general exclusion of other molecules in a sample. The aptamer may be a nucleic acid such as an RNA, a DNA, a modified nucleic acid, or a mixture thereof. The aptamer may also be a nucleic acid in a linear or circular form and may be single stranded or double stranded. The aptamer may comprise oligonucleotides that are at least 5, at least 10, at least 15, at least 20, at least 25, at least 30, at least 35, at least 40 or more nucleotides in length. Aptamers may comprise sequences that are up to 40, up to 60, up to 80, up to 100, up to 150, up to 200 or more nucleotides in length. Aptamers may be from about 5 to about 150 nucleotides, from about 10 to about 100 nucleotides, or from about 20 to about 75 nucleotides in length. While aptamers are discussed herein as nucleic acid molecules (e.g., oligonucleotides) aptamers, aptamer equivalents may also be used in place of the nucleic acid aptamers, such as peptide aptamers.

According to one embodiment, the pharmaceutical agent and the affinity moiety (e.g. antibody or aptamer) are attached directly to one another.

Thus according to another aspect of the present invention there is provided a composition of matter (e.g. complex) comprising an affinity moiety attached to a therapeutic agent, wherein the affinity moiety specifically binds to a polypeptide selected from the group consisting of HSP90B1, DNAJB4, PI4K2A, DBN1, PRKCSH, SPTBN1, NPM1, ITGA3 and any of the polypeptides listed in Table 1, herein below.

Affinity moieties have been described herein above.

The pharmaceutical agent of the invention may be attached or conjugated to the affinity moiety of the invention in various ways, depending on the context, application and purpose.

When both the pharmaceutical agent and the affinity moiety are polypeptides, the conjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding an antibody of the invention and be expressed in a host cell to produce a recombinant conjugated antibody. Alternatively, at least one of the affinity moiety or pharmaceutical agent may be chemically synthesized by, for example, the stepwise addition of one or more amino acid residues in defined order such as solid phase peptide synthetic techniques.

A pharmaceutical agent may also be attached to the affinity moiety of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like.

Exemplary methods for conjugating peptide pharmaceutical agent to polypeptide affinity moieties (e.g. antibodies) are described herein below:

SPDP conjugation—A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions are incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM KH2PO4 pH 6.5. The reduced peptide is combined with the SPDP-antibody in a molar ratio of 1:10 antibody:peptide and incubated at 4° C. overnight to form a peptide-antibody conjugate.

Glutaraldehyde conjugation—A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes).

Carbodiimide conjugation—Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

When both the pharmaceutical agent and the affinity moiety are antibodies, the present invention contemplates generation of bispecific antibodies wherein each arm of the antibody recognizes a different antigen.

It will be appreciated that the affinity moiety and the pharmaceutical agent of this aspect of the present invention may be attached indirectly—e.g. via a particle, wherein the pharmaceutical agent is inside the particle or on the outer surface thereof and the affinity moiety is on the outer surface of the particle.

Thus, according to another aspect of the present invention there is provided a particle having a senescent cell affinity moiety attached to an outer surface thereof, the senescent cell affinity moiety capable of specifically binding a polypeptide selected from the group consisting of HSP90B1, DNAJB4, PI4K2A, DBN1, PRKCSH, SPTBN1, NPM1, ITGA3 and any of the polypeptides listed in Table 1, herein below.

Senescent cell affinity moieties have been described herein above.

As used herein, "particles" refers to nano-micro structures which are not biological cells.

The particle may be a synthetic carrier, gel or other object or material having an external surface which is capable of being loadable with (e.g., encapsulating) a pharmaceutical agent. The particle may be either polymeric or non-polymeric preparations.

Exemplary particles that may be used according to this aspect of the present invention include, but are not limited to polymeric particles, microcapsules, liposomes, microspheres, microemulsions, nanoparticles, nanocapsules, nano-spheres, nano-liposomes, nano-emulsions and nanotubes.

According to a particular embodiment, the particles are nanoparticles.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

The particles of this aspect of the present invention may have a charged surface (i.e., positively charged or negatively charged) or a neutral surface.

Agents which are used to fabricate the particles may be selected according to the desired charge required on the outer surface of the particles.

Thus, for example if a negatively charged surface is desired, the particles may be fabricated from negatively charged lipids (i.e. anionic phospholipids) such as described herein below.

When a positively charged surface is desired, the particles may be fabricated from positively charged lipids (i.e. cationic phospholipids), such as described herein below.

As mentioned, non charged particles are also contemplated by the present invention. Such particles may be fabricated from neutral lipids such as phosphatidylethanolamine or dioleoylphosphatidylethanolamine (DOPE).

It will be appreciated that combinations of different lipids may be used to fabricate the particles of the present invention, including a mixture of more than one cationic lipid, a mixture of more than one anionic lipid, a mixture of more than one neutral lipid, a mixture of at least one cationic lipid and at least one anionic lipid, a mixture of at least one cationic lipid and at least one neutral lipid, a mixture of at least one anionic lipid and at least one neutral lipid and additional combinations of the above. In addition, polymer-lipid based formulations may be used.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), poly-(lactic-co-glycolic)poly-(vinyl-alcohol), polyvinylpyrrolidone, polyethyloxazoline, polyllydroxyetlyloxazolille, solyhydroxypryloxazoline, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose.

The polymers may be employed as homopolymers or as block or random copolymers.

The particles may also include other components. Examples of such other components includes, without being limited thereto, fatty alcohols, fatty acids, and/or cholesterol esters or any other pharmaceutically acceptable excipients which may affect the surface charge, the membrane fluidity and assist in the incorporation of the biologically active lipid into the lipid assembly. Examples of sterols include cholesterol, cholesterol hemisuccinate, cholesterol sulfate, or any other derivatives of cholesterol. Preferred lipid assemblies according the invention include either those which form a micelle (typically when the assembly is absent from a lipid matrix) or those which form a liposome (typically, when a lipid matrix is present).

The particles of the present invention may be modified. According modified to enhance their circulatory half-life (e.g. by PEGylation) to reduce their clearance, to prolong their scavenging time-frame and to allow antibody binding. The PEG which is incorporated into the articles may be characterized by of any of various combinations of chemical composition and/or molecular weight, depending on the application and purpose.

Methods of coupling affinity moieties (e.g. antibodies) on particle's outer surface (e.g., liposomes) are known in the art.

As used herein "coupling" or "coupled on" refers to covalent or non-covalent attachment of the affinity moiety to the particle.

Antibody conjugation methods which can be used in accordance with the teachings of the present invention can be divided to direct binding or indirect binding. Some methods are provided hereinbelow and are summarized in Ansell, Supra. While specifically referring to liposomes, the procedures described hereinbelow may be applied to a variety of particles, while using modified protocols simply applied by the ordinary artisan.

Direct conjugation methods are well known to those of skill in the art. See for example, G. Gregoriadis, (1984) "Liposome Technology" CRC Press, Boca Raton, Fla. and D. D. Lasic, "Liposomes: from physics to applications" (1993) Elsevier, Amsterdam; N.Y. Particularly preferred is conjugation through a thioether linkage. This may be accomplished by reacting the antibody with a maleimide derivatized lipid such as maleimide derivatized phosphatidylethanolamine (M-PE) or dipalmitoylethanolamine (M-DEP). This approach is described in detail by Martin et al. J. Biol. Chem., 257: 286-288 (1982) which is incorporated herein by reference.

In another preferred embodiment, the antibody can be coupled to a hydrophilic polymer (e.g., a PEG). Means of attaching targeting molecules to polymer linkers are well known to those of skill in the art (see, e.g., chapter 4 in Monoclonal Antibodies: Principles and Applications, Birch and Lennox, eds., John Wiley & Sons, Inc., New York (1995); and Blume et al. Biochem. Biophys. Acta. 1149: 180-184 (1993). In a particularly preferred embodiment, an antibody or a fragment thereof (e.g., Fab' fragment) is linked to a maleimide derivatized PEG through the —SII group of the antibody. The maleimide-derivative of PEG-PE is included in the liposome preparation as described above and below and the antibody can be conjugated with the liposome via the sulfhydryl group at pH 7.2.

Amine modifications making use of cross-linking agents such as EDC are taught in Endoh et al. 1981 J. Immun. Meth. 44:79-85; Dunnick 1975 J. Nuclear. Med. 16:483-487; Alternatively, direct modification of antibodies with activated fatty acids, such as N-hydroxysuccinimide (NHS) eater or palmitic acid, prior to incorporation into a liposome membrane, typically by detergent dialysis procedures (Huang et al. 1980, J. Biol. Chem. 255:8015-8018. Reagents, such as EDC, are used in conjunction with NHS to activate acidic functions on liposomes, which are then conjugated to the amino groups on antibodies. Better control of the conjugation reaction can be achieved using heterobifunctional cross-linkers which efficiently introduce a unique and selective reactive function, such as a protected thiol or maleimide group. Examples of these crosslinkers are SPDP (Barbet et al. 1981 J. Supramolec. Struct. Cell. Biochem. 16:243-258), S-acetylthioglycolic acid N-hydroxysuccinimide ester (SATA, Jones 1993 Biochim. Biophys. Acta. 1152: 23:1-32; Schwendener 1990 Biochim. Biophys. Acta. 1026:69-79 and 4-(p-maleimidophenyl)butyric acid N-hydroxysuccinimide ester(SMPB (Hansen 1995 Biochim. Biophys. Acta. 1239:133-144). Antibodies which have been activated by these crosslinkers can, after deprotection where appropriate, react with activated lipids in liposome bilayers. Maleimide and protected thiol-derivatized lipids are available from commercial sources for this purpose.

Deprotection of 3-pyridyl disulfides is usually effected by DTT and occasionally by some other mercaptan. Once deprotected, sulfhydryl groups can react with maleimide (for example SMPB-modified conjugates) or iodo (for example, iodoacetic acid N-hydroxysuccinimide ester (SIAA)-modified conjugates) groups. Maleimide groups are recommended since iodo functions can react with amino groups in either of the substrates, leading to undesirable side products. Deprotection is not required for these reagents.

Indirect conjugation methods:

Biotin-avidin—For example, a biotin conjugated antibody may be bound to a particle (e.g., liposome) containing a streptavidin. Alternatively, the biotinylated antibody may be conjugated to a biotin derivatized liposome by an avidin or streptavidin linker. Ahmad et al., Cancer Res., 52: 4817-4820 (1992) which is herein incorporated by reference, describes such a mode of coupling. When monovalent Fab molecules are used, typically about 30 to 125 and more typically about 50 to 100 Fab' molecules per liposome are used.

Binding via protein A/G/L-liposome conjugates targeted to the Fc chain of antibodies is taught in Matthay et al. 1986 Cancer Res. 46:4904-4910; Machy et al. 1983 Biochem. Biophys. Acta. 901:157-160.

Loading of the particle with the pharmaceutical agent can be effected concomitant with, or following particle assembly.

Thus, in one preferred embodiment, for example, when the pharmaceutical agent is a nucleic acid, e.g., DNA, RNA, siRNA, plasmid DNA, short-hairpin RNA, small temporal RNA (stRNA), microRNA (miRNA), RNA mimetics, or heterochromatic siRNA, the nucleic acid agent of interest has a charged backbone that prevents efficient encapsulation in the lipid particle. Accordingly, the nucleic acid agent of interest may be condensed with a cationic polymer, e.g., PEI, polyamine spermidine, and spermine, or cationic peptide, e.g., protamine and polylysine, prior to encapsulation in the lipid particle. In one embodiment, the agent is not condensed with a cationic polymer.

In another embodiment, the agent of interest is encapsulated in the lipid particle in the following manner. The particle is provided lyophilized. The agent of interest is in an aqueous solution. The agent of interest in aqueous solution is utilized to rehydrate the lyophilized lipid particle. Thus, the agent of interest is encapsulated in the rehydrated lipid particle.

In one embodiment, two agents of interest may be delivered by the particles (e.g., lipid based particle). One agent is hydrophobic and the other is hydrophilic. The hydrophobic agent may be added to the lipid particle during formation of the lipid particle. The hydrophobic agent associates with the lipid portion of the lipid particle. The hydrophilic agent is added in the aqueous solution rehydrating the lyophilized lipid particle. In an exemplary embodiment of two agent delivery a condensed siRNA is encapsulated in a liposome and wherein a drug that is poorly soluble in aqueous solution is associated with the lipid portion of the lipid particle. As used herein, "poorly soluble in aqueous solution" refers to a composition that is less that 10% soluble in water.

As used herein "loading" refers to encapsulating or absorbing.

The term "encapsulated" as used herein refers to the pharmaceutical agent being distributed in the interior portion of the particles. Preferably, the pharmaceutical agents are homogenously distributed. Homogeneous distribution of a pharmaceutical agent in polymer particles is known as a matrix encapsulation. However, due to the manufacturing process it is foreseen that minor amounts of the pharmaceutical agent may also be present on the outside of the particle and/or mixed with the polymer making up the shell of the particle.

As used herein "absorbed" refers to binding of the pharmaceutical agent to the outer surface of the particle.

Since pharmaceutical agents described herein (e.g. cytotoxic agents) are attached to affinity moieties which target senescent cells, the present inventors propose that these complexes may be used to treat subjects having diseases associated with cell senescence.

As used herein, the term "subject" refers to a mammalian subject, preferably a human.

A number of diseases and conditions, which involve an inflammatory response can be treated using the methodology described hereinabove. Examples of such diseases and conditions are summarized infra.

Inflammatory diseases—Include, but are not limited to, chronic inflammatory diseases and acute inflammatory diseases.

Inflammatory Diseases

Examples of inflammatory diseases include, but are not limited to the diseases listed below.

An inflammatory disease such as asthma.

Inflammatory diseases include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Tract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Dickman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998:7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauciimmune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C R et al., Eur J Gastroenterol Hepatol. 1999 June; 11 (6):595).

Further, inflammatory diseases include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 March, 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of inflammatory diseases include, but are not limited to, contact dermatitis and drug eruption.

Examples of types of T lymphocyte mediating inflammatory diseases include, but are not limited to, helper T lymphocytes and cytotoxic T lymphocytes.

Examples of helper T lymphocyte-mediated inflammatory diseases include, but are not limited to, $T_h1$ lymphocyte mediated inflammation and $T_h2$ lymphocyte mediated inflammation.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauciimmune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau YE. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg CP. et al., Eur J Gastroenterol Hepatol. 1999 June; 11 (6):595) and autoimmune hepatitis (Manns MP. J Hepatol 2000 August; 33 (2):326).

Examples of autoimmune neurological diseases include, but are not limited to, multiple sclerosis (Cross AH. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2): 140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan OT. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a particular embodiment, the agents (and combinations thereof) are used to treat pre-malignant lesions.

As used herein, the phrase "pre-malignant lesion" refers to a mass of cells and/or tissue having increased probability of transforming into a malignant tumor. Examples of pre-malignant lesions include, but are not limited to, adenomatous polyps, Barrett's esophagus, Pancreatic Intraepithelial Neoplasia (PanIN), IPMN (Intraductal Papillary Mucinus Neoplasia), DCIS (Ductal Carcinoma in Situ) in the breast, leukoplakia and erythroplakia. Thus, the pre-malignant lesion which is treated using the agents of this aspect of the present invention can transform into a malignant solid or non-solid (e.g., hematological malignancies) cancer (or tumor). According to a particular embodiment, the pre-malignant lesion which is treated using the agents of the present invention is an adenomatous polyp of the colon, an adenomatous polyp of the rectum, an adenomatous polyp of the small bowel and Barrett's esophagus.

Examples of fibrotic diseases include diseases of an epithelial barrier tissue, diseases of the skin, lung or gut.

Contemplated fibrotic diseases which may be treated using the agents described herein include but are not limited to eosinophilic esophagitis, hypereosinophilic syndromes (HES), Loeffler's endomyocarditis, endomyocardial fibrosis, idiopathic pulmonary fibrosis, and scleroderma.

According to a particular embodiment the agents are used for treating liver fibrosis, wound healing, skin fibrosis, pulmonary disease, kidney fibrosis, prostatitis, atherosclerosis, arthritis, osteoporosis or pancreatitis.

An exemplary pulmonary disease contemplated by the present invention is chronic obstructive pulmonary disease (COPD) or Idiopathic pulmonary fibrosis.

According to sill another embodiment, the disease is associated with cartilage degeneration—e.g. arthritis.

According to still another embodiment, the disease is associated with bone degeneration—e.g. osteoporosis.

According to still another embodiment, the disease is not cancer. The complexes of the present invention may be provided per se or may be formulated in compositions intended for a particular use.

Since the complexes of the present invention selectively target senescent cells, the present inventors contemplate that another use thereof is in cosmetic compositions as anti-aging agents for rejuvenating the skin. Thus, the agents of the present invention may be formulated for cosmetics.

Such compositions typically comprise pharmaceutically acceptable excipient, notably dermatologically acceptable suitable for external topical application.

The cosmetic composition according to the present invention may further comprise at least one pharmaceutical adjuvant known to the person skilled in the art, selected from thickeners, preservatives, fragrances, colorants, chemical or mineral filters, moisturizing agents, thermal spring water, etc.

The composition may comprise at least one agent selected from a sebum-regulating agent, an antibacterial agent, an antifungal agent, a keratolytic agent, a keratoregulating agent, an astringent, an anti-inflammatory/anti-irritant, an antioxidant/free-radical scavenger, a cicatrizing agent, an anti-aging agent and/or a moisturizing agent.

The term "sebum-regulating agent" refers, for example, to 5-α-reductase inhibitors, notably the active agent 5-α-Avocuta® sold by Laboratoires Expanscience. Zinc and gluconate salts thereof, salicylate and pyroglutamic acid, also have sebum-suppressing activity. Mention may also be made of spironolactone, an anti-androgen and aldosterone antagonist, which significantly reduces the sebum secretion rate after 12 weeks of application. Other extracted molecules, for example from seeds of the pumpkin Cucurbita pepo, and squash seed oil, as well as palm cabbage, limit sebum production by inhibiting 5-α-reductase transcription and activity. Other sebum-regulating agents of lipid origin that act on sebum quality, such as linoleic acid, are of interest.

The terms "anti-bacterial agent" and "antifungal agent" refer to molecules that limit the growth of or destroy pathogenic microorganisms such as certain bacteria like P. acnes or certain fungi (Malassezia furfur). The most traditional are preservatives generally used in cosmetics or nutraceuticals, molecules with anti-bacterial activity (pseudo-preservatives) such as caprylic derivatives (caproyl glycine, glyceryl caprylate, etc.), such as hexanediol and sodium levulinate, zinc and copper derivatives (gluconate and PCA), phytosphingosine and derivatives thereof, benzoyl peroxide, piroctone olamine, zinc pyrithione, selenium sulfide, econazole, ketoconazole, or local antibiotics such as erythromycin and clindamycin, etc.

The terms "keratoregulating agent" and "keratolytic agent" refer to an agent that regulates or helps the elimination of dead cells of the stratum corneum of the epidermis. The most commonly used keratoregulating/keratolytic agents include: alpha-hydroxy acids (AHAs) of fruits (citric acid, glycolic acid, malic acid, lactic acid, etc.), AHA esters, combinations of AHAs with other molecules such as the combination of malic acid and almond proteins (Keratolite®) the combination of glycolic acid or lactic acid with arginine or the combination of hydroxy acid with lipid molecules such as LHA® (lipo-hydroxy acid), amphoteric hydroxy acid complexes (AHCare), willow bark (Salix alba bark extract), azelaic acid and salts and esters thereof, salicylic acid and derivatives thereof such as capryloyl salicylic acid or in combination with other molecules such as the combination of salicylic acid and polysaccharide (betahydroxy acid, or BHA), tazarotene, adapalene, as well as molecules of the retinoid family such as tretinoin, retinaldehyde, isotretinoin and retinol.

The term "astringent" refers to an agent that helps constrict pores, the most commonly used being polyphenols, zinc derivatives and witch hazel.

The term "anti-inflammatory/anti-irritant" refers to an agent that limits the inflammatory reaction led by cytokines or arachidonic acid metabolism mediators and has soothing and anti-irritating properties. The most traditional are glycyrrhetinic acid (licorice derivative) and salts and esters thereof, alpha-bisabolol, Ginkgo biloba, Calendula, lipoic acid, beta-carotene, vitamin B3 (niacinamide, nicotinamide), vitamin E, vitamin C, vitamin B12, flavonoids (green tea, quercetin, etc.), lycopene or lutein, avocado sugars, avocado oleodistillate, arabinogalactan, lupin peptides, lupin total extract, quinoa peptide extract, Cycloceramide'® (oxazoline derivative), anti-glycation agents such as carnosine, N-acetyl-cysteine, isoflavones such as, for example, genistein/genistin, daidzein/daidzin, spring water or thermal spring water (eau d'Avene, eau de la Roche Posay, eau de Saint Gervais, eau d'Uriage, eau de Gamarde), goji extracts (Lycium barbarum), plant amino acid peptides or complexes, topical dapsone, or anti-inflammatory drugs.

The term "antioxidant" refers to a molecule that decreases or prevents the oxidation of other chemical substances. The antioxidants/free-radical scavengers that may be used in combination are advantageously selected from the group comprised of thiols and phenols, licorice derivatives such as glycyrrhetinic acid and salts and esters thereof, alpha-bisabolol, Ginkgo biloba extract, Calendula extract, Cycloceramide® (oxazoline derivative), avocado peptides, trace elements such as copper, zinc and selenium, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene, the family of polyphenols such as tannins, phenolic acids, anthocyanins, flavonoids such as, for example, extracts of green tea, of red berries, of cocoa, of grapes, of Passiflora incarnata or of Citrus, or isoflavones such as, for example, genistein/genistin and daidzein/daidzin. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The agents that cicatrize/repair the barrier function which may be used in combination are advantageously vitamin A, panthenol (vitamin B5), Avocadofurane®, avocado sugars, lupeol, maca peptide extract, quinoa peptide extract, arabinogalactan, zinc oxide, magnesium, silicon, madecassic or asiatic acid, dextran sulfate, coenzyme Q10, glucosamine and derivatives thereof, chondroitin sulfate and on the whole glycosaminoglycans (GAGs), dextran sulfate, ceramides, cholesterol, squalane, phospholipids, fermented or unfermented soya peptides, plant peptides, marine, plant or biotechnological polysaccharides such as algae extracts or fern extracts, trace elements, extracts of tannin-rich plants such as tannins derived from gallic acid called gallic or hydrolysable tannins, initially found in oak gall, and catechin tannins resulting from the polymerization of flavan units whose model is provided by the catechu (Acacia catechu). The trace elements that may be used are advantageously selected from the group comprised of copper, magnesium, manganese, chromium, selenium, silicon, zinc and mixtures thereof.

Anti-aging agents that can act in combination to treat acne in mature subjects are antioxidants and in particular vitamin C, vitamin A, retinol, retinal, hyaluronic acid of any molecular weight, Avocadofurane®, lupin peptides and maca peptide extract.

The most commonly used moisturizers/emollients are glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, monounsaturated and polyunsaturated omega-3, -6, -7 and -9 fatty acids (linoleic acid, palmitoleic acid, etc.), sunflower oleodistillate, avocado peptides and cupuacu butter.

For treatment of diseases, the agents of the present invention may be formulated in pharmaceutical compositions.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the therapeutic agent (as described herein above) accountable for the biological effect which is attached directly or indirectly to the targeting agent. It will be appreciated that the pharmaceutical compositions may comprise additional active agents known to be useful in treating a particular disease. Thus, for example for treatment of skin fibrotic diseases, the present inventors contemplate pharmaceutical compositions comprising the above described agents together with at least one sebum-regulating agent, an antibacterial agent, an antifungal agent, a keratolytic agent, a keratoregulating agent, an astringent, an anti-inflammatory/anti-irritant, an antioxidant/free-radical scavenger, a cicatrizing agent, an anti-aging agent and/or a moisturizing agent, as described herein above.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a particular embodiment, the route of administration is via topical delivery.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. siRNA agents together with targeting agents) effective to prevent, alleviate or ameliorate symptoms of a disorder (e.g., fibrotic or inflammatory disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. mouse models of liver fibrosis induced by $CCl_4$, mouse model of pancreatitis induced by Caerulein, mouse model of COPD) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Since the present inventors have found that the polypeptides HSP90B1, DNAJB4, PI4K2A, DBN1, PRKCSH, SPTBN1, NPM1, ITGA3 and any of the polypeptides listed in Table 1, herein below are selectively upregulated on the surface of senescent cells as compared to non-senescent cells, the present inventors propose that measuring the level of such proteins may be used to identify senescent cells.

Thus, according to still another aspect of the present invention there is provided a method of identifying senescent cells in a cell population comprising analyzing the amount of at least one polypeptide selected from the group consisting of HSP90B 1, DNAJB4, PI4K2A, DBN1, PRKCSH, SPTBN1, NPM1, ITGA3 and any of the polypeptides listed in Table 1 on the membrane of the cells of the cell population, wherein a level of the at least one polypeptide above a predetermined amount is indicative of senescent cells.

The identifying may be part of a method of diagnosing a disease associated with senescent cells as further described herein above.

The term "diagnosing" as used herein refers to determining the presence of a disease, classifying a disease, staging a disease, determining a severity of a disease, monitoring disease progression, forecasting an outcome of the disease, predicting survival and/or prospects of recovery (i.e. prognosis).

The subject may be a healthy animal or human subject undergoing a routine well-being check up. Alternatively, the subject may be at risk of having the disease (e.g., a genetically predisposed subject, a subject with medical and/or family history of cancer, a subject who has been exposed to carcinogens, occupational hazard, environmental hazard] and/or a subject who exhibits suspicious clinical signs of the disease [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Still alternatively, the subject may be diagnosed as having a disease associated with senescent cells, but the stage is being evaluated.

Determining an expression of any of the polypeptides listed above may be effected on the RNA or protein level as detailed below.

According to one embodiment, the determining is effected ex vivo.

According to another embodiment, the determining is effected in vivo.

Diseases which may be diagnosed are listed herein above. According to a particular embodiment, the disease is cancer or a premalignant disease (e.g. Pancreatic Intraepithelial Neoplasia (PanIN)).

Methods of Detecting Expression of the Polypeptides on the RNA Level

When the polypeptide is expressed solely on the membrane (e.g. ITGA3) and not in other cell compartments, RNA based methods on whole cell extracts may be used. In this scenario lysed cells may be used for the detection of the polypeptides.

Preferably, when the polypeptide is not expressed solely on the membrane and is expressed in other cell compartments, RNA based methods are performed on membrane extracts.

In order to detect expression of the polypeptides on the RNA level, typically polynucleotide probes (e.g. oligonucleotides or primers) are used that are capable of specifically hybridizing to their RNA or cDNA generated therefrom.

Preferably, the oligonucleotide probes and primers utilized by the various hybridization techniques described hereinabove are capable of hybridizing to their targets under stringent hybridization conditions.

By way of example, hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the Tm, final wash solution of 3 M TMACl, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the Tm, final wash solution of 3 M TMACl, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature at 2.5-3° C. below the Tm and final wash solution of 6×SSC at 22° C. (moderate hybridization solution).

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide Microarray—

In this method oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Methods of Detecting the Polypeptides on the Protein Level

When the polypeptide is expressed solely on the membrane (e.g. ITGA3) and not in other cell compartments, whole cell extracts may be analyzed. In this scenario lysed cells may be used for the detection of the polypeptides.

Preferably, when the polypeptide is not expressed solely on the membrane and is expressed in other cell compartments, membrane extracts are used for methods which require the generation of cellular extracts. In situ methods, such as immunostaining and FACS may be used regardless whether the polypeptide is expressed solely on the membrane or not.

Determining expression of the polypeptides on the protein level is typically effected using an antibody capable of specifically interacting with same. Methods of detecting the above described proteins include immunoassays which include but are not limited to competitive and non-competitive assay systems using techniques such as Western blots, radioimmunoassays, ELISA (enzyme linked immunosorbent assay), "sandwich" immunoassays, and immunoprecipitation assays and immunohistochemical assays as detailed herein below.

Below is a list of techniques which may be used to determine the level of the proteins described herein above on the protein level.

Enzyme Linked Immunosorbent Assay (ELISA):

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-Immunoassay (RIA):

In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously. It will be appreciated that when the protein is not expressed selectively on the cell membrane, care should be taken to avoid the antibody penetrating the cell membrane.

Immunohistochemical Analysis:

This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain. It will be appreciated that when the protein is not expressed selectively on the cell membrane, care should be taken to avoid the antibody penetrating the cell membrane.

In Situ Activity Assay:

According to this method, a chromogenic substrate is applied on the cells containing an active enzyme and the enzyme catalyzes a reaction in which the substrate is decomposed to produce a chromogenic product visible by a light or a fluorescent microscope.

As mentioned, the identifying/diagnosing/staging is carried out by analyzing an amount or activity of the polypeptides in a cell sample of the subject, wherein a difference in an amount or activity thereof beyond a predetermined threshold with respect to a control cell sample is indicative of the disease. It will be appreciated that the amount of change may correspond with a degree or a stage of the disease. Thus, larger differences may indicate a later stage of the disease with a poorer prognosis, whereas lower differences may indicate an early stage of the disease with a better prognosis.

The patient sample typically comprises cells. It may be part of a tissue sample, retrieved during a biopsy. Alternatively, the sample may be a bodily fluid, e.g. blood, urine, saliva, CSF, plasma etc.

For diagnosis of cancer, the cell sample may comprise cells of the primary tumor and/or metastatic effusion thereof.

The predetermined level may be established based on results from control (non-diseased) cells.

The control cell sample typically depends on the patient sample being analyzed. Thus, for example, in the case of colon cancer, the control sample may comprise colon cells of a healthy individual (or at least one not suffering from colon cancer) or from a known stage of colon cancer (e.g. non-metastatic stage). In the case of breast cancer, the control sample may comprise breast cells of a healthy individual (or at least one not suffering from breast cancer) or from a known stage of breast cancer.

The control cells are typically normally differentiated, non-senescent cells, preferably of the same tissue and specimen as the tested cells. Typically, the amount of change in expression of the polypeptides is statistically significant.

Preferably, the difference is at least 10%, 20%, 30%, 40%, 50%, 80%, 100% (i.e., two-fold), 3 fold, 5 fold or 10 fold different as compared to the control cells.

It will be appreciated that the control data may also be taken from databases and literature.

On obtaining the results of the analysis, the subject is typically informed. Additional diagnostic tests may also be performed so as to corroborate the results of the diagnosing (e.g. gold standard tests, assessing the aggressiveness of the tumor, the patient's health and susceptibility to treatment, etc.).

Imaging studies such as CT and/or MRI may be obtained to further diagnose the disease.

In addition, when the disease is cancer, the diagnosis or choice of therapy may be determined by further assessing the size of the tumor, or the lymph node stage or both, optionally together or in combination with other risk factors.

The present inventors propose that based on the results of the diagnosis, a suitable therapy may be selected—i.e. personalized medicine.

As mentioned, the present inventors showed that downregulation of cell-surface Grp94 decreases NK-cell mediated cytotoxicity toward senescent cells and decreased susceptibility of senescent cells for elimination by monocytes.

Thus, the present inventors propose that polypeptides which are expressed on the surface of senescent cells may be used to elicit or boost an immune response to a senescent cell.

Thus, according to another aspect of the present invention there is provided a method of eliciting or boosting an immune response to a senescent cell in a subject comprising administering to the subject a pharmaceutical composition comprising at least one polypeptide or a polynucleotide encoding same selected from the group consisting of HSP90B1, DBN1, PRKCSH, SPTBN1, NPM1 and a polypeptide set forth in Table 1, wherein the pharmaceutical composition does not comprise senescent cells, thereby eliciting or boosting the immune response to the senescent cell.

The immune response may comprise clearance of the senescent cell by the immune response (e.g. a helper T cell or a cytotoxic T-cell response).

The present inventors contemplate administering at least one, two, three, four, five, six, seven, eight, nine, ten or more of the polypeptides of this aspect of the present invention.

The polypeptides may be provided as full length polypeptides or as antigenic fragments thereof.

As used herein, the term "antigenic fragment" refers to an immunogenic portion of the full-length polypeptide, Such antigenic fragments may comprise at least 5, 10, 20, 25, 30, 35, 40, 45, 50, 55, or 60 or more contiguous amino acids (or any number of contiguous amino acids between 5-60, including 5-10, 10-15, 15-20, 20-25, 25-30, 30-35, 35-40, 40-45, 45-50, 40-55, or 55-60, or more than 60 contiguous amino acids) of the polypeptides. In a more particular embodiment, antigenic fragment comprises at least 20 contiguous amino acids. An antigenic fragment of a mature or full-length polypeptide has one or more epitopes that induce a specific immune response, which may comprise production of antibodies that specifically bind to the antigenic fragment and to the immunogenic portion within the mature and full-length polypeptide from which the antigenic peptide is derived, and to a senescent cell that expresses the polypeptide.

The polypeptides or fragments thereof of the present invention may be administered per se to induce an immune response, or alternatively, as part of a composition i.e. vaccine, which comprises an immunologically acceptable carrier.

It will be appreciated that the polypeptides may be administered in the form of an expression construct which comprises the corresponding nucleic acid sequence to the polypeptide. The expression construct may be administered instead of the polypeptides themselves (e.g. in a prime boost protocol) or in addition to the polypeptides of the present invention. It will be further appreciated that the polypeptides may be expressed in a cell population (e.g. dendritic cells) and the cell population may be provided. According to a particular embodiment, the polypeptides are not administered as part of a senescent cell population or membrane fraction thereof.

Suitable agents that provide a target antigen include recombinant vectors, for example, bacteria, viruses, and naked DNA. Recombinant vectors are prepared using standard techniques known in the art, and contain suitable control elements operably linked to the nucleotide sequence encoding the target antigen. See, for example, Plotkin, et al. (eds.) (2003) Vaccines, 4.sup.th ed., W. B. Saunders, Co., Phila., Pa.; Sikora, et al. (eds.) (1996) Tumor Immunology Cambridge University Press, Cambridge, UK; Hackett and Ham (eds.) Vaccine Adjuvants, Humana Press, Totowa, N.J.; Isaacson (eds.) (1992) Recombinant DNA Vaccines, Marcel Dekker, NY, N.Y.; Morse, et al. (eds.) (2004) Handbook of Cancer Vaccines, Humana Press, Totowa, N.J.), Liao, et al. (2005) Cancer Res. 65:9089-9098; Dean (2005) Expert Opin. Drug Deliv. 2:227-236; Arlen, et al. (2003) Expert Rev. Vaccines 2:483-493; Dela Cruz, et al. (2003) Vaccine 21:1317-1326; Johansen, et al. (2000) Eur. J. Pharm. Biopharm. 50:413-417; Excler (1998) Vaccine 16:1439-1443; Disis, et al. (1996) J. Immunol. 156:3151-3158). Peptide vaccines are described (see, e.g., McCabe, et al. (1995) Cancer Res. 55:1741-1747; Minev, et al. (1994) Cancer Res. 54:4155-4161; Snyder, et al. (2004) J. Virology 78:7052-7060. Virus-derived vectors include viruses, modified viruses, and viral particles (see, e.g., U.S. Pat. No. 8,926, 993, incorporated herein by reference). The virus-derived vectors can be administered directly to a mammalian subject, or can be introduced ex vivo into an antigen presenting cell (APC), where the APC is then administered to the subject.

Viral vectors may be based on, e.g., Togaviruses, including alphaviruses and flaviviruses; alphaviruses, such as Sindbis virus, Sindbis strain SAAR86, Semliki Forest virus (SFV), Venezuelan equine encephalitis (VEE), Eastern equine encephalitis (EEE), Western equine encephalitis, Ross River virus, Sagiyami virus, O'Nyong-nyong virus, Highlands J virus. Flaviviruses, such as Yellow fever virus, Yellow fever strain 17D, Japanese encephalitis, St. Louis encephalitis, Tick-borne encephalitis, Dengue virus, West Nile virus, Kunjin virus (subtype of West Nile virus); arterivirus such as equine arteritis virus; and rubivirus such as rubella virus, herpesvirus, modified vaccinia Ankara (MVA); avipox viral vector; fowlpox vector; vaccinia virus vector; influenza virus vector; adenoviral vector, human papilloma virus vector; bovine papilloma virus vector, and so on. Viral vectors may be based on an orthopoxvirus such as variola virus (smallpox), vaccinia virus (vaccine for smallpox), Ankara (MVA), or Copenhagen strain, camelpox, monkeypox, or cowpox. Viral vectors may be based on an avipoxvirus virus, such as fowlpox virus or canarypox virus.

Adenoviral vectors and adeno-associated virus vectors (AAV) are available, where adenoviral vectors include adenovirus serotype 5 (adeno5; Ad5), adeno6, adeno11, and adeno35. Available are at least 51 human adenovirus serotypes, classified into six subgroups (subgroups A, B, C, D, E, and F). Adenovirus proteins useful, for example, in assessing immune response to an "empty" advenoviral vector, include hexon protein, such as hexon 3 protein, fiber protein, and penton base proteins, and human immune responses to adenoviral proteins have been described (see, e.g., Wu, et al. (2002) J. Virol. 76:12775-12782; Mascola (2006) Nature 441:161-162; Roberts, et al. (2006) Nature 441:239-243).

General methods to prepare immunogenic or vaccine compositions are described in Remington's Pharmaceutical Science; Mack Publishing Company Easton, Pa. (latest edition). To increase immunogenicity, the polypeptides of the present invention may be adsorbed to or conjugated to beads such as latex or gold beads, ISCOMs, and the like. Immunogenic compositions may comprise adjuvants, which are substance that can be added to an immunogen or to a vaccine formulation to enhance the immune-stimulating properties of the immunogenic moiety. Liposomes are also considered to be adjuvants (Gregoriades, G. et al., Immunological Adjuvants and Vaccines, Plenum Press, New York, 1989) Examples of adjuvants or agents that may add to the effectiveness of proteinaceous immunogens include aluminum hydroxide, aluminum phosphate, aluminum potassium sulfate (alum), beryllium sulfate, silica, kaolin, carbon, water-in-oil emulsions, and oil-in-water emulsions. A preferred type of adjuvant is muramyl dipeptide (MDP) and various MDP derivatives and formulations, e.g., N-acetyl-D-glucosaminyl-(.beta.1-4)-N-acetylmuramyl-L-alanyl-D-isoglutami-ne (GMDP) (Hornung, R L et al. Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al. (1992) N. Engl. J. Med., 327:1209-1238). Other useful adjuvants are, or are based on, cholera toxin, bacterial endotoxin, lipid X, whole organisms or subcellular fractions of the bacteria Propionobacterium acnes or Bordetella pertussis, polyribonucleotides, sodium alginate, lanolin, lysolecithin, vitamin A, saponin and saponin derivatives such as QS21 (White, A. C. et al. (1991) Adv. Exp. Med. Biol., 303:207-210) which is now in use in the clinic (Helling, F et al. (1995) Cancer Res., 55:2783-2788; Davis, T A et al. (1997) Blood, 90: 509), levamisole, DEAE-dextran, blocked copolymers or other synthetic adjuvants. A number of adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Alhydrogel (aluminum hydroxide), or a mixture of Amphigen and Alhydrogel. Aluminum is approved for human use.

The present invention also contemplates antiserum induced in one subject using the polypeptides or fragments thereof of the present invention, removed from that subject and used to treat another subject by passive immunization or transfer of the antibodies. For disclosure of such passive immunization with patient sera, neutralizing antisera or mAbs, see Nishimura Y et al. (2003) Proc Natl Acad Sci USA 100:15131-36; Mascola J R (2003) Curr Mol Med. 3:209-16; Ferrantelli F et al. (2003) AIDS 17:301-9; Ferrantelli F et al (2002) Curr Opin Immunol. 14:495-502; Xu W et al. (2002) Vaccine 20:1956-60; Nichols C N et al. (2002) AIDS Res Hum Retrovir. 8:49-56; Cho M W et al. (2000) J. Virol. 74:9749-54; Mascola J R et al. (2000) Nat Med. 6:207-10; Andrus. L et al. (1998) J. Inf. Dis. 77: 889-897; Parren P W (1995) AIDS 9:F1-6; Hinkula J et al. (1994) J Acquir Immune Defic Syndr. 7:940-51; Prince A M et al. (1991) AIDS Res Hum Retrovir 7:971-73; Emini E A et al. (1990) J. Virol. 64:3674-84, all incorporated by reference.

The amount of polypeptide or fragment to be administered to induce an immune response depends on the precise polypeptide selected, the health and weight of the recipient, the route of administration, the existence of other concurrent treatment, if any, the frequency of treatment, the nature of the effect desired, and the judgment of the skilled practitioner.

An exemplary dose for treating a subject is an amount of up to about 100 milligrams of active polypeptide per kilogram of body weight. A typical single dosage of the polypeptide or chimeric protein is between about 1 ng and about 100 mg/kg body weight, and preferably from about 10 µg to about 50 mg/kg body weight. A total daily dosage in the range of about 0.1 milligrams to about 7 grams is preferred for intravenous administration. A useful dose of an antibody for passive immunization is between 10-100 mg/kg. It has been suggested (see references cited above for passive immunity) that an effective in vivo dose of an antibody/antiserum is between about 10- and 100-fold more than an effective neutralizing concentration or dose in vitro. These dosages can be determined empirically in conjunction with the present disclosure and state-of-the-art. The polypeptides of the present invention may be administered alone or in conjunction with other therapeutics directed to the treatment of the disease or condition.

The subject vaccines find use in methods for eliciting or boosting a cellular immune response, e.g., a helper T cell or a cytotoxic T-cell response to senescent cells. The vaccine of the present invention may be used, for example, both for immunization and to boost immunity after exposure. As such, the subject vaccines find use as both prophylactic and therapeutic vaccines to induce immune responses that are specific for senescent cells that are relevant to various disease conditions.

The vaccine may contain other antigenic polypeptides, e.g. comprised in a tumor cell lysate, an irradiated tumor cell, an antigen-presenting cell pulsed with peptides of the target antigen (e.g. a dendritic cell).

The vaccine of this aspect of the present invention may also comprise an agent which enhances the immunogenicity of the immunogen e.g. a helper antigen or carrier moiety. A helper antigen includes a T cell helper antigen, which is an antigen that is recognized by a T helper cell and evokes an immune response in a T helper cell. T helper cells are lymphocytes that are involved in activating and directing other immune cells such as cytotoxic T cells, B cells, and/or macrophages. Carrier moieties have been long known in the immunology art and include without limitation, keyhole limpet hemocyanin, bovine serum albumin, cationized BSA, or ovalbumin. For human use, toxoids of bacterial proteins (e.g., tetanus toxoid, diphtheria toxoid, cholera toxoid, and the like) are typically employed as carrier proteins.

In certain embodiments, the immunogen comprises at least one senescent cell associated antigen or at least one antigenic fragment thereof and a helper antigen or carrier moiety that is linked, conjugated, or attached to the antigen or antigenic fragment thereof. The helper antigen or carrier moiety may be recombinantly expressed in frame and directly linked to a senescent cell associated antigen or fragment thereof. In certain embodiments, a fusion protein comprising at least two senescent cell associated antigens or at least two antigenic fragments thereof or a combination of same may also comprise a helper antigen or carrier moiety. Alternatively, the helper antigen or carrier moiety may be chemically conjugated, linked, or attached to the senescent cell associated antigen or fragment thereof. In still another embodiment, the helper antigen or carrier moiety may be formulated together with any immunogen described herein but not covalently or non-covalently bound to the immunogen to form an immunogenic composition.

In another embodiment, the immunogenic compositions described herein include a co-stimulatory polypeptide. In certain embodiments, the immunogen comprises at least one senescent cell associated antigen (as described herein) or at least one antigenic fragment thereof and a co-stimulatory molecule that is linked, conjugated, or attached to the antigen or antigenic fragment thereof. The co-stimulatory molecule may be recombinantly expressed in frame and directly linked to a senescent cell associated antigen or fragment thereof. In certain embodiments, a fusion protein comprising at least two senescent cell associated antigen or at least two antigenic fragments thereof or a combination of same may also comprise a co-stimulatory molecule. Alternatively, the co-stimulatory molecule may be chemically conjugated, linked, or attached to the senescent cell associated antigen or fragment thereof. In still another embodiment, the co-stimulatory molecule may be formulated together with any immunogen described herein but not covalently or non-covalently bound to the immunogen to form the immunogenic composition.

Exemplary co-stimulatory molecules include, by way of example, GM-CSF, IL-2, IL-4, IL-6, IL-7, IL-15, IL-21, IL-23, TNFa, B7.1 (CD80), B7.2 (CD86), 41BB, CD40 ligand (CD40L), drug-inducible CD40 (iCD40), and the like. When an immunogenic composition comprises a polynucleotide encoding the co-stimulatory molecule, or a recombinant expression virus comprising the polynucleotide, expression of the co-stimulatory molecule is typically under the control of one or more regulatory elements selected to direct the expression of the coding sequences in a cell of choice, such as a dendritic cell.

Recombinantly engineered antigen-presenting cells such as dendritic cells, for example, may be modified by recombinant technology to express increased levels of antigen presenting machinery, adhesion and/or co-stimulatory molecules, including MHC class I/antigen complexes, MHC class II/antigen complexes, CD1, hsp70-90, CD9, CD63, CD81, CD1 1b, CD1 1c, CD40, CD54 (ICAM-1), CD63, CD80, CD86, 41BBL, OX40L, chemokine receptor CCR1-10 and CXCR1-6, mannose-rich C-type lectin receptor DEC205 and Toll-like receptors TLR4 and TLR9 or membrane-bound TGF-β. The exosomes derived from these recombinantly engineered antigen presenting cells will express these additional molecules and can transfer them to the T helper cells, T regulatory cells, or dendritic cells upon absorption.

As mentioned, the present invention contemplates antigen-presenting cells (APCs), e.g., dendritic cells (DCs), that include senescent cell-associated antigens, as described herein above, for example, by being presented on the surface of the antigen-presenting cells.

Dendritic cells play a critical role in coordinating innate and adaptive immune responses. DCs are bone-marrow derived cells characterized by dendritic morphology and high mobility that are seeded in all tissues. DCs are specialized antigen presenting cells that are capable of capturing and processing antigens, migrating from the periphery to a lymphoid organ, and presenting the antigens in a MHC-restricted manner to naive T-cells (see, e.g., Banchereau & Steinman, 1998, Nature 392:245-252; Steinman et al., 2003, Ann. Rev. Immunol. 21:685-711). Immature DCs are capable of processing and presenting antigens, which leads to immune regulation and/or suppression. Maturation (activation) of DCs is required to induce differentiation of antigen-specific T cells into effector T cells (see, e.g., Palucka et al, 2012, Nat. Rev. Cancer 12:265-277). Mature DCs express high levels of MHC-antigen complex and other co-stimulatory molecules, such as CD40, B7-1, B7-2, and CD 1a (see, e.g., Steinman, 1991, Ann. Rev. Immunol. 9:271-296; Banchereau & Steinman, 1998, Nature 392:245-252). These molecules play key roles in stimulating T cells. Due to their properties, DC-based vaccination strategies have been developed in cancer (see, e.g., Heiser et al, 2001, Cancer Res. 61:338; Heiser et al, 2001, J. Immunol. 166: 2953; Milazzo et al, 2002, Blood 101:977; Zu et al, 2003, Cancer Res. 63:2127) Likewise, DC based immunogens (vaccines) may be able to elicit CD8+ T cells capable of recognizing peptide-MHC Class complexes on senescent cells and target them for destruction.

Dendritic cells may be obtained from various sources using methods known in the art. DC precursors may be purified from peripheral blood (see, e.g., Fong et al., 2003, Annu Rev. Immunol. 15: 138). DCs may be also be differentiated from peripheral blood monocytes or CD34+ hematopoietic progenitor cells ex vivo (see, e.g., Sallusto et al, 1994, J. Exp. Med. 179: 1109; Banchereau et al, 2001, Cancer Res. 61:6451; Makensen et al, 2000, Int. J. Cancer 86:385). Methods for in vitro proliferation of dendritic cells from DC precursors and their use as immunogens are described in U.S. Pat. Nos. 5,851,756; 5,994,126; 6,475,483; and 8,283,163 each of which is incorporated herein by reference in its entirety. A method for isolating DCs from human peripheral blood is described in U.S. Pat. No. 5,643,786, incorporated herein by reference in its entirety. U.S. Patent Publication 2006/0063255, U.S. Patent Publication 2006/0057129, and U.S. Pat. No. 7,247,480, each of which is incorporated herein by reference in its entirety, describe methods for making dendritic cell vaccines from human embryonic stem cells.

Methods of isolating APCs, such as dendritic cells, are known in the art. Procedures such as repetitive density gradient separation, fluorescence activated cell sorting techniques, positive selection, negative selection, or a combination thereof are routinely used to obtain enriched populations of DCs. Methods for isolating DCs may be found in O'Doherty et al, 1993, J. Exp. Med. 178: 1067-78; Young and Steinman, 1990, J. Exp. Med. 171:1315-32; Freudenthal et al, 1990, Proc. Natl. Acad. Sci. USA 57:7698-7702; Markowicz and Engleman, 1990, J. Clin. Invest. 85:955-961; Mehta-Damani et al, 1994, J. Immunol. 153:996-1003; Thomas et al, 1993, J. Immunol. 151:6840-6852.

Dendritic cells may be loaded with specific antigens ex vivo and then administered to a subject (see, e.g., Banchereau et al, 2005, Nat. Rev. Immunol. 5:296-306; Figdor et al, 2004, Nat. Med. 10:475-480, each of which is incorporated herein by reference in its entirety). Various methods for loading antigens to DCs have been described and are known in the art. R A encoding a specific antigen may be pulsed into dendritic cells before administration to a subject by electroporation, cationic lipids, cationic peptides or using dendrimers (see, e.g., Boczkwoski et al. 1996, J. Exp. Med. 184:465; Heiser et al, 2001, Cancer Res. 61:338; Heiser et al, J. Immunol. 2001, 166:2953; U.S. Patent Publication 2006/0063255; Choi et al, 2005, Cell Cycle 4:669). DCs may also be loaded with protein or peptide that is purified or isolated from a target cell, chemically synthesized, or recombinantly expressed. Nucleic acid vectors encoding a specific antigen may also be used for DC loading (see, e.g., Frolkis et al., 2003, Cancer Gene Ther. 10:239). Exemplary vectors include plasmids, cationic lipid complexes, viral vectors, cDNA encoding antigen loaded onto dendrimers, or other small particulates that enhance uptake by phagocytic cells. U.S. Pat. Nos. 6,300,090 and 6,455,299 describe using non-replicating viral vectors comprising sequence encoding an antigen for infecting dendritic cells, resulting in antigen presentation on the DC surface.

Alternatively, DCs may be loaded with specific antigens in vivo.

Antigens may be delivered directly to DCs using chimeric proteins that are comprised of a DC receptor-specific antibody fused to a selected antigen (see, e.g., Bonifaz et al, 2004, J. Exp. Med. 199:815-824; Bonifaz et al, 2004, J. Exp. Med. 196: 1627-1638; Hawiger et al, 2001, J. Exp. Med. 194:769-780; each of which is incorporated herein by reference in its entirety). U.S. Patent Publication 2012/0070462, incorporated herein by reference in its entirety, describes targeted antigen delivery to dendritic cells using recombinant viral vectors comprising a polynucleotide encoding the antigen and a targeting molecule, which binds to a DC-specific surface marker (e.g., DC-SIGN).

Antigenic peptides useful for presentation by DCs for vaccination are peptides that stimulate a T cell mediated immune response (e.g., cytotoxic T cell response) by presentation to T cells on MHC molecules. Useful antigenic peptides and proteins for use in the present disclosure include those derived from senescent cells (e.g., senescent cell-associated antigens). Depending on the method of DC loading utilized, a senescent cell-associated antigen may be presented in a variety of forms. In some embodiments, a senescent cell-associated antigen is presented as a senescent cell lysate to DCs. In other embodiments, senescent cell-associated antigens are obtained by acid elution of peptides presented on MHC molecules of the senescent cell surface. For example, senescent cells are washed with an isotonic solution to remove media components. The cells are then treated with acid to dissociate peptides from surface MHCs, and the cells are removed from the solution containing the soluble peptides. Antigenic peptides may be obtained by chemical synthesis or produced using recombinant methods with host cells and vector expression systems. A senescent cell associated antigen may also be delivered as a polynucleotides (RNA or DNA) to a DC directly or indirectly (e.g., via a plasmid or viral vector). The antigenic peptides presented on MHC molecules are typically short peptides and may be 5, 6, 7, 8, 9, or 10 amino acids, for example.

A senescent cell associated antigen introduced into DCs may also be designed as a fusion peptide, wherein the antigen is joined to a protein or peptide sequence that enhances transport into endosomal and other intracellular compartments involved in Class II histocompatibility loading. For example, the N-terminus of such a fusion protein may comprise a suitable heterologous leader or signal sequence for the endosomal compartment and the C-terminus may comprise a transmembrane and luminal component of a member of the LAMP family for lysosomal targeting (see, e.g., U.S. Pat. No. 5,633,234; WO 02/080851; Sawada et al, 1993, J. Biol. Chem. 268:9014; each of which is incorporated by reference herein in its entirety). Endosomal and lysosomal sorting signals include tyrosine based signals, dileucine-based signals, acidic clusters, and transmembrane proteins labeled with ubiquitin (see, e.g., Bonifacino et al, 2003, Annu. Rev. Biochem. 72:395; U.S. Pat. No. 6,248, 565).

It is expected that during the life of a patent maturing from this application many relevant pharmaceutical agents will be developed and the scope of the term pharmaceutical agent is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell Culture:

Human IMR-90 fibroblasts were purchased from ATCC, and Mouse embryonic fibroblasts (MEFs) were derived according to standard procedures (Manipulating the Mouse Embryo: A Laboratory Manual, 3rd ed. A. Nagy, et al., Cold Spring Harbor Laboratory Press, 2003). Cells were cultured in Dulbecco's modified Eagle's medium (DMEM) supplemented with 2 mM L-glutamine, 100 units/ml of penicillin, 100 µg/ml of streptomycin, and 10% FBS, in a low oxygen incubator. DIS was induced by etoposide treatment (E1383, Sigma) at a concentration of 100 µM for 48 hours as described previously (Krizhanovsky et al. Cell 134.4 (2008): 657-667). OIS was induced by infection of IMR-90 cells with pWZL plasmid containing oncogenic Hras$^{V12}$.

Identification of Cell Surface Proteins:

Cell-surface proteins were purified from IMR-90 cells, 9 days post insult using commercial kit (Pierce). Briefly, cells were exposed to Sulfo-NHS—SS-biotin, lysed and loaded on columns to capture membrane proteome. Following several washing steps, purified cell surface proteins were finally eluted. Samples were then analyzed by Label-free mass spectrometry at the proteomic unit at the Grand Israel National Center for Personalized Medicine. Integrative analysis was done by Ingenuity Pathway Analysis software (Qiagen). Cell-surface proteins were analyzed according to their original subcellular localization using the cellular component branch of GO by online DAVID v6.7 software.

Validation of MS Results:

Grp94 translocation to cell surface was first validated by purification of plasma membrane proteome (Qproteome Plasma Membrane Protein Kit, Qiagen). Equal amounts of cell-surface proteins or total cell lysates from growing IMR-90 and senescent IMR-90 were separated on 12% SDS-polyacrylamide gels and transferred onto PVDF membrane (IPVH00010, Millipore). After blocking with 5% BSA in TBST (TBS with 0.01% Tween 20) for 1 hr, the membranes were probed with antibodies against Grp94 (PA5-24824, Thermo Fisher Scientific), HLA-A,B,C (BioLegend), GAPDH and β-tubulin (both, Santa Cruz) overnight at 4° C. Antibodies were visualized with HRP-based chemiluminescence detection kit (34080, Thermo Fisher Scientific).

Immunofluorescence Assay:

Cells were incubated with anti-Grp94 antibody (diluted in DMEM) for 3h in 37° C., washed 3 times with warm PBS and incubated with goat anti-rabbit Alexa647 conjugated antibody (111-605-003, Jackson immuno-research) for 30 minutes, washed 3 times with warm PBS and visualized in Olympus IX81 microscope and XM10 camera and processed using ImageJ v1.47 software.

Flow-Cytometry Assay

IMR-90 cells were gently dissociated from plates using TripLE express reagent (12604-013, Thermo Fisher Scientific), and maintained in cold FACS buffer (PBS containing 1% FCS and 0.1% Sodium Azid) throughout all procedure. Cells were incubated with anti-Grp94 antibody (1:20 in FACS buffer), followed by goat anti-rabbit Alexa647 conjugated antibody. DAPI was shortly introduced in order to exclude dead cells. Cells were analyzed in a SORP-LSRII instrument (BD Biosciences). Data was collected from at least 20,000 single-cell events. Cells were gated by their size (FSC/SSC), DAPI negative (live cells) and then analyzed for their fluorescence intensity at the wavelength of 647 (cell-surface Grp94 level), using FlowJo v10 software.

GPM1 Inhibitor:

GPM1 was synthesized by the Organic synthesis unit at the Weizmann institute as was described previously (Kim et al. 2012). Final product was characterized by NMR. GPM1 were dissolved in 5% DMSO in phosphate-buffered saline (PBS) and control vehicle was 5% DMSO in PBS.

Cytotoxicity Assays:

For in-vitro cytotoxicity assays target cells were plated in 12-well plates at $4 \times 10^4$ cells per well; $1 \times 10^5$ NK-92 cells were subsequently added to each well. Following 2 h of co-incubation, NK-92 cells were washed gently and the cytotoxicity was determined based on the viability of remaining adherent cells. To block Grp94-mediated cytotoxicity, ON-TARGETplus SMARTpool small-interfering RNA targeting HSP90B1 and the non-targeting (control) pool were transfected into senescent IMR-90 cells with Dharmafect 1 reagent (all from Dharmacon, Lafayette, Colo., USA). Transfections were performed overnight, and 4 days later cytotoxicity assays were executed. Viability was determined by using PrestoBlue reagent kit (A13262, Life Technologies Ltd.), and was calculated relatively to control DMSO treated cells.

For phagocytosis assay Etopoide-treated IMR-90 cells were plated in 12-well plates at $4 \times 10^4$ cells per well. Cells were incubated 24 hrs with GPM1 at the concentration of 0, 10 or 100 m/ml, and then co-cultures with MM6 cells for 6 days. Assessment of remaining cells was determined by crystal violet staining.

Statistical Analysis:

Statistical analysis of the results was analyzed using one-sided two-sample t-tests or one-way ANOVA followed by Tukey post-hoc test. Data are expressed as means±S.E.M, a P value<0.05 was considered significant.

Results

Senescent cells are known to express several common ligands which are required for natural killer immune cells recognition and subsequent cytotoxicity [5]. In order to identify the fraction proteome which is being expressed on cell surface of senescent cells, the present inventors analyzed membrane proteins using high-throughput proteomics analysis. Normal human fibroblasts cells IMR90 were used to execute two distinct sets of experiments; exposure to the chemotherapeutic agent Etoposide for 48 hrs, which results in DNA Damage Induced Senescence (DIS), and infection with oncogenic H-Ras$^{V12}$, leading to Oncogene-induced senescence (OIS). At day 9 post DNA damage or introduction of the oncogene, cells acquired senescent-like morphology and proliferative arrest (FIG. 1A). At this time point, the cells were exposed to Sulfo-NHS—SS-biotin, lysed and loaded on columns to capture membrane proteome. Following a few rounds of washing, the proteins were eluted to obtain membrane protein samples. The samples were then analyzed by mass spectrometry (FIG. 1B). 2198 different proteins were identified in the samples, 257 of them existed only in samples derived from senescent cells but not from growing cells (FIG. 1C).

An integrative list of human hits with 5 peptides and more +20% coverage and more is provided in Table 1, herein below.

TABLE 1

| SEQ ID NO: | GeneBank No. | Gene | Protein Names | Protein Description | Unique Peptides Per Protein | Protein Sequence Coverage (%) | Average Ratio |
|---|---|---|---|---|---|---|---|
| 26 | NM_001199954.1. | ACTG1 | ACTG_HUMAN, SW: P63261 | Actin, cytoplasmic 2 | 6 | 70.7 | 8.47 |
| 27 | NM_001150.2. | ANPEP | B4DP96_HUMAN, TR: B4DP96 | Uncharacterized protein | 7 | 26.3 | 2.70 |
| 28 | NM_001177.5. | ARL1 | B4DZG7_HUMAN, TR: B4DZG7 | ADP-ribosylation factor-like protein 1 | 5 | 57.0 | 2.11 |

TABLE 1-continued

| SEQ ID NO: | GeneBank No. | Gene | Protein Names | Protein Description | Unique Peptides Per Protein | Protein Sequence Coverage (%) | Average Ratio |
|---|---|---|---|---|---|---|---|
| 29 | NM_001693.3. | ATP6V1B2 | VATB2_HUMAN, SW: P21281 | V-type proton ATPase subunit B, brain isoform | 8 | 28.8 | 4.37 |
| 30 | NM_004859.3. | CLTC | CLH1_HUMAN, SW: Q00610-2 | Isoform 2 of Clathrin heavy chain 1 | 43 | 34.3 | 2.95 |
| 31 | NM_004094.4. | EIF2S1 | H0YJS4_HUMAN, TR: H0YJS4 | Eukaryotic translation initiation factor 2 subunit 1 | 5 | 23.8 | 2.52 |
| 32 | NM_002056.3. | GFPT1 | GFPT1_HUMAN, SW: Q06210-2 | Isoform 2 of Glucosamine-fructose-6-phosphate aminotransferase [isomerizing] 1 | 8 | 19.7 | 2.29 |
| 33 | NM_000424.3. | KRT5 | K2C5_HUMAN, SW: P13647 | Keratin, type II cytoskeletal 5 | 10 | 20.8 | 2.98 |
| 34 | NM_001256282.1 | KRT8 | K2C8_HUMAN, SW: P05787 | Keratin, type II cytoskeletal 8 | 5 | 20.5 | 2.14 |
| 35 | XM_005248567.1. | MCCC2 | MCCB_HUMAN, SW: Q9HCC0-2 | Isoform 2 of Methylcrotonoyl-CoA carboxylase beta chain, mitochondrial | 7 | 25.0 | 2.43 |
| 36 | NM_001114614.1. | MFGE8 | F5H7N9_HUMAN, TR: F5H7N9 | Lactadherin short form | 5 | 29.0 | 2.89 |
| 37 | NM_001024628.2. | NRP1 | Q5T7F1_HUMAN, TR: Q5T7F1 | Neuropilin 1 | 6 | 27.6 | 5.49 |
| 38 | NM_201381.2. | PLEC | PLEC_HUMAN, SW: Q15149-7 | Isoform 7 of Plectin | 106 | 45.8 | 1.93 |
| 39 | NM_152132.2. | PSMA3 | PSA3_HUMAN, SW: P25788-2 | Isoform 2 of Proteasome subunit alpha type-3 | 5 | 25.4 | 2.18 |
| 40 | NM_001199163.1. | PSMC5 | PRS8_HUMAN, SW: P62195-2 | Isoform 2 of 26S protease regulatory subunit 8 | 8 | 25.1 | 4.72 |
| 41 | NM_012232.5. | PTRF | PTRF_HUMAN, SW: Q6NZI2-2 | Isoform 2 of Polymerase I and transcript release factor | 5 | 28.3 | 2.01 |
| 42 | NM_004637.5. | RAB7A | RAB7A_HUMAN, SW: P51149 | Ras-related protein Rab-7a | 5 | 31.9 | 2.75 |
| 43 | NM_001256577.2. | RPL10 | F8W7C6_HUMAN, TR: F8W7C6 | 60S ribosomal protein L10 | 6 | 31.9 | 3.38 |
| 44 | NM_001042576.1. | RRBP1 | F8W7S5_HUMAN, TR: F8W7S5 | Ribosome-binding protein 1 | 9 | 24.4 | 3.70 |
| 45 | NM_001788.5 | SEPT7 | H0Y3Y4_HUMAN, TR: H0Y3Y4 | Septin-7 | 8 | 21.2 | 214.68 |
| 46 | NM_006288.3. | THY1 | E9PIM6_HUMAN, TR: E9PIM6 | Thy-1 membrane glycoprotein | 6 | 45.8 | 3.91 |

In order to understand the nature of the identified proteins, integrative analysis of the identified proteins was performed using the data mining software, Ingenuity. The distribution of the protein's original subcellular origin was analyzed. Surprisingly, much of the cell-surface proteome was recognized as an intra-cellular (FIG. 1C). Nonetheless, the vast majority of the proteins are presented by only 2-4 peptides, which could imply that many peptides identified do not stand for the full and functional proteins, but rather for peptides presented by antigen presenting machineries. These machineries might include major histo-compatibility complexes and members of the heat shock protein families.

In a parallel analysis approach, the identified proteins were mapped to known canonical pathways. In the context of immune-related processes, integrin signaling was identified as the strongest hit (FIG. 1D). Integrin signaling in senescent cells consist of at least 10 different integrins, predominantly ITGA3 and ITGB5. The second strongest immunological hit was Fcγ-receptor mediated phagocytosis. This finding is in-line with several studies which identify macrophages and monocytes as potentially important players in immune surveillance of senescent cells [16]. Another strong immunological hit was fMLP (f-Met-Leu-Phe) signaling. N-formylated peptides are believed to derive from mitochondrial proteins upon tissue damage and known to act mainly on neutrophils [17]. fMLP is a strong chemo-attractant, but also induces adherence, degranulation and production of tissue-destructive oxygen-derived free radicals in phagocytic cells [17, 18].

Finally, potential upstream regulators were identified (FIG. 1E). Nrf2, the nuclear factor 2 transcription factor, was found to be the most activated. Although Nrf2 is constitutively expressed in all tissues, it may be further induced by cellular stressors including endogenous reactive-oxygen species and oncogene activation [19]. This single transcription factor mediates multiple avenues of cytoprotection by activating the transcription of more than 200 genes interacts with other important cell regulators such as p53 and NF-κB and through their combined interactions is the guardian of health-span, protecting against many age-related diseases including cancer and neurodegeneration [20]. Conversely, RICTOR, the Rapamycin-insensitive companion of mTOR, was identified as being the most inhibited upstream regulator. RICTOR binds directly to mTOR to stabilize TORC2 which regulates cell growth and survival in response to hormonal signals and growth factors [21].

Next, the results from the two main experiments were intersected. This approach increased exclusivity of these proteins for the senescence program with no dependence on the exact trigger and increased the confidence in specific proteins. A short but unique list of 9 proteins was found to be common between both DIS and OIS (FIG. 2A). Under these restrictions, 7 out of the 9 proteins were previously documented as being found in the plasma membrane compartment, and 3 of them were previously reported to exist apically on cell surface (according to the UniProtKB/Swiss-Prot database). A closer look at the top 3 proteins revealed that one of them is ICAM1, a cell surface glycoprotein which is typically expressed on endothelial cells and cells of the immune system (FIG. 2B). This protein is known to be up-regulated during cellular senescence, and therefore it can serve as internal control and provide independent confirmation for the results of this study [22]. Another hit is ITGA3, an integrin alpha subunit that together with integrin beta-1 composes α3β1 integrin duplex. The α3α1 complex is a receptor for variety of ECM components, known to play a role in neural migration and endothelial adhesion [23, 24]. The third hit, Grp94, also known as Endoplasmin or gp96, is the main ER-resident chaperone. Grp94 belongs to the heat-shock 90 family and encoded by the HSP90B1 gene in humans. The encoded protein is localized to the ER where it plays critical roles in folding proteins in the secretory pathway such as Toll-like receptors and integrins [25]. Unlike the first two hits, normally, this protein does not find its way to the cell-surface. Nevertheless, upon severe ER stress, Grp94 can be actively translocated to the extracellular interface, where it displays important modulatory effects on both the innate and adaptive immune response [26, 27]. Macrophages for instance, are a prominent GRP94 target, as GRP94 reported to activate several signaling pathways in both LPS-dependent and independent manner [28]. Second, Grp94 can activate dendritic cells (DCs), to enhance their immune-stimulatory capacities [29]. In parallel, Grp94 can undergo endocytosis to antigen-presenting cells (APCs), and to mediate the cross-presentation of Grp94-bound peptides on MHC class I molecules for activation of cytotoxic T cells [30, 31].

Despite its average size (92469Da), 42 different unique peptides were identified for this protein, covering almost 60% of protein sequence (FIG. 2B). Analysis of the exact location of those sequences on the protein sequence map suggests that the hits represent the full length protein and not fragments or single peptides (FIG. 2C).

In order to validate the existence of the full length Grp94 protein on cell-surface of senescent cells, an unbiased approach was implemented which consists of plasma membrane purification followed by Western Blot (WB) analysis. The results of this experiment show that Grp94 cell-surface expression is preferential or even exclusive to senescent cells, with a clear band in the size of ~96kDA (FIG. 2D). In order to quantitatively assess this elevation, immunofluorescence staining was performed on live cells under conditions which allow the staining of only the external Grp94 molecules, and the samples were analyzed by FACS (FIG. 2E). The results indicate a 3-fold increase in Grp94 levels on senescent cells (FIG. 2F). As a positive control the levels of ICAM1 were examined which showed a 2-fold increase in senescent cells (FIGS. 2G-H). Finally, IMR90 growing or DIS cells were seeded on cover-slips and stained for cell-surface Grp94/HLA-A,B,C. In agreement with the results described above, the senescent IMR90 cells display a marked increase in the levels of cell-surface Grp94 (FIG. 2I).

Stress in the ER might increase its promiscuity, enabling ER resident proteins to be found in other sites in the cell, such as cell-surface. In order to understand whether the existence of Grp94 on the surface of senescent cells is a direct consequence of the senescence program, or alternatively, a common result of stress conditions, the present inventors examined the kinetics of cell-surface Grp94 at different time-points after treating propagating IMR90 cells with Etoposide (FIG. 3A). Importantly, Grp94 levels were not elevated 3 days after etoposide treatment, indicating that the presence of Grp94 on cell surface is not a common stress response, but only after the establishment of the senescent program (FIG. 3B). In addition, the data suggest that during cellular senescence Grp94 gradually accumulates on the cell surface. The continuous recycling of escaped ER proteins such as Grp94 is mediated by retrograde transport from Golgi to ER through COPI-coated vesicles [32]. During this process, Grp94 localization is regulated through its C-terminal KDEL sequence, which is recognized by the KDEL receptor ERD2 [33]. Grp94 homodimerization potentially promote ERD2 binding [34, 35]. Consequently, ERD2-Grp94 complex returns to the ER where it dissociates, freeing ERD2 for further cycling of transport. In order to examine the validity of this pathway to Grp94 during the senescence program, GPM1, a small molecule which has been shown to promote dimerization of Grp94, thus promoting recycling of Grp94 into the ER and blocking its translocation to cell-surface (FIG. 3B) [36] was synthesized. After ensuring that GPM1 does not affect the cell's viability under different concentrations (FIG. 3C), it was found that GPM1 could reduce cell surface levels of Grp94 of senescent IMR90 cells (FIG. 3D). Thus, it may be concluded that GPM1 may be used to manipulate cell-surface levels of Grp94, and accordingly to investigate the role of Grp94 in the interaction of senescent cells with the immune system.

Grp94 is known to have multiple effects on the immune system, a property for which it has received the title "the immune system's Swiss army-knife" [27]. Studies from recent years have revealed close interactions between senescent cells and the immune system. Immune surveillance of senescent cells is mediated on many occasions by NK cells which are attracted to the site of the senescent cells where they are recognized and eliminated [7, 37]. In order to elucidate possible role for Grp94 in immune surveillance of NK cells the total levels of Gr94 in senescent IMR90 cells were down-regulated using specific siRNA for 4 days. The effect was validated the by Western blot analysis (FIG. 4A). A slight decrease in the viability of the siHSP90B1 treated cells was observed in comparison to siControl (FIG. 4B). This result is in line with the role of ER-resident Grp94 in stabilization of unfolded proteins during stress conditions. Finally, those cells were co-cultured with NK-92 cells for 2 hours. The NK cells were then gently removed and cytotoxicity was calculated as the ratio between the IRM90 cell's viability prior to and following co-culture. The results show a decreased cytotoxicity of NK-92 cells toward senescent cells that have low Grp94 expression levels (FIG. 4C), suggesting that NK cell cytotoxicity is mediated, at least in part, by cell-surface Grp94.

In order to understand the functional importance of Grp94 for phagocytosis of macrophages, DIS IMR90 cells were treated with GPM1 or DMSO. The viability of senescent cells post co-culturing with human MM6 monocytes was examined. The preliminary data show that under the effective concentration of GPM1 (100 μM) senescent cells have reduced viability following co-culturing with monocytes (FIG. 4D), suggesting Grp94 as a regulator of immune surveillance of senescent cells.

The levels of cell surface Grp94 were also examined in mouse embryonic fibroblast cells (MEFs). A significant elevation in cell surface Grp94 was detected upon treatment with etoposide (FIG. 4E). The relatively high correlation between localization of Grp94 in human and mouse cells implies that it may serve as a new marker for senescent cells.

Figure 5B:
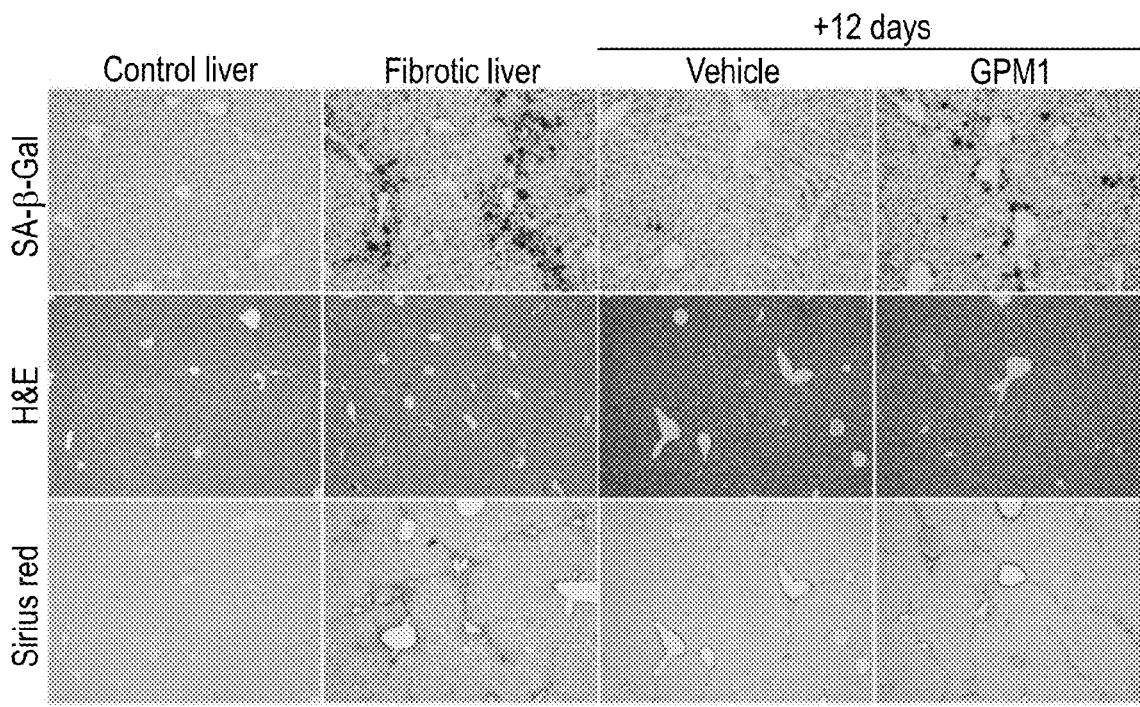
Figure 5C:
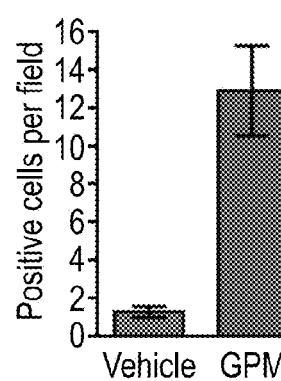
Figure 5D:
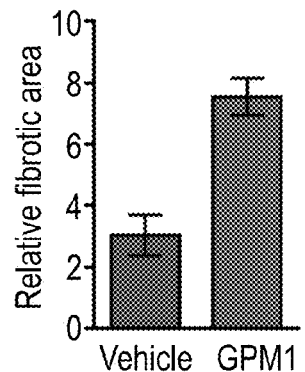

In order to shed more light on the biological significance of cell surface Grp94 in senescent cells, mice were treated with GPM1 following the establishment of chronic fibrosis in the liver. It was previously demonstrated that senescent hepatic stellate cells are gradually eliminated by immune cells until their full elimination around 10-20 days from the last CC14 injection. The administration of GPM1 dramatically increased intracellular levels of Grp94 and eliminated the positive staining at the plasma membrane regions (FIG. 5A). Histological analyses indicate that GPM1 treatment blocks the clearance of senescent cells (FIG. 5B). The increase in tissue-residing senescent cells was accompanied with increased fibrosis in the GPM1-treated animals compared to the Vehicle-treated animals (FIG. 5B). Quantitative analysis confirmed these findings (FIGS. 5C,D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Campisi, J. and F. d'Adda di Fagagna, *Cellular senescence: when bad things happen to good cells*. Nat Rev Mol Cell Biol, 2007. 8(9): p. 729-40.
2. Collado, M., M. A. Blasco, and M. Serrano, *Cellular senescence in cancer and aging*. Cell, 2007. 130(2): p. 223-33.
3. Adams, P. D., *Healing and hurting: molecular mechanisms, functions, and pathologies of cellular senescence*. Mol Cell, 2009. 36(1): p. 2-14.
4. Serrano, M., et al., *Oncogenic ras provokes premature cell senescence associated with accumulation of p53 and p16INK4a*. Cell, 1997. 88(5): p. 593-602.
5. Xue, W., et al., *Senescence and tumour clearance is triggered by p53 restoration in murine liver carcinomas*. Nature, 2007. 445(7128): p. 656-60.
6. Kang, T. W., et al., *Senescence surveillance of premalignant hepatocytes limits liver cancer development*. Nature, 2011. 479(7374): p. 547-51.
7. Krizhanovsky, V., et al., *Senescence of activated stellate cells limits liver fibrosis*. Cell, 2008. 134(4): p. 657-67.
8. Michaloglou, C., et al., *BRAFE600-associated senescence-like cell cycle arrest of human naevi*. Nature, 2005. 436(7051): p. 720-4.
9. Parrinello, S., et al., *Stromal-epithelial interactions in aging and cancer: senescent fibroblasts alter epithelial cell differentiation*. J Cell Sci, 2005. 118(Pt 3): p. 485-96.
10. Jeyapalan, J. C. and J. M. Sedivy, *Cellular senescence and organismal aging*. Mech Ageing Dev, 2008. 129(7-8): p. 467-74.
11. Collado, M. and M. Serrano, *Senescence in tumours: evidence from mice and humans*. Nat Rev Cancer, 2010. 10(1): p. 51-7.
12. Ovadya, Y. and V. Krizhanovsky, *Senescent cells: SASPected drivers of age-related pathologies*. Biogerontology, 2014. 15(6): p. 627-42.
13. Grivennikov, S. I., F. R. Greten, and M. Karin, *Immunity, inflammation, and cancer*. Cell, 2010. 140(6): p. 883-99.
14. Baker, D. J., et al., *Opposing roles for p16Ink4a and p19Arf in senescence and ageing caused by BubR1 insufficiency*. Nat Cell Biol, 2008. 10(7): p. 825-36.
15. Baker, D. J., et al., *Clearance of p16Ink4a-positive senescent cells delays ageing-associated disorders*. Nature, 2011. 479(7372): p. 232-6.
16. Lujambio, A., et al., *Non-cell-autonomous tumor suppression by p53*. Cell, 2013. 153(2): p. 449-60.
17. Carp, H., *Mitochondrial N-formylmethionyl proteins as chemoattractants for neutrophils*. The Journal of experimental medicine, 1982. 155(1): p. 264-275.
18. Selvatici, R., et al., *Signal transduction pathways triggered by selective formylpeptide analogues in human neutrophils*. Eur J Pharmacol, 2006. 534(1-3): p. 1-11.
19. DeNicola, G. M., et al., *Oncogene-induced Nrf2 transcription promotes ROS detoxification and tumorigenesis*. Nature, 2011. 475(7354): p. 106-9.
20. Lewis, K. N., et al., *Nrf2, a guardian of healthspan and gatekeeper of species longevity*. Integr Comp Biol, 2010. 50(5): p. 829-43.
21. Shiota, C., et al., *Multiallelic disruption of the rictor gene in mice reveals that mTOR complex 2 is essential for fetal growth and viability*. Dev Cell, 2006. 11(4): p. 583-9.
22. Gorgoulis, V. G., et al., *p53-dependent ICAM-1 overexpression in senescent human cells identified in atherosclerotic lesions*. Lab Invest, 2005. 85(4): p. 502-11.
23. Schmid, R. S., et al., *alpha3beta1 integrin modulates neuronal migration and placement during early stages of cerebral cortical development*. Development, 2004. 131(24): p. 6023-31.
24. Glinskii, O. V., et al., *Endothelial integrin alpha3beta1 stabilizes carbohydrate-mediated tumor/endothelial cell adhesion and induces macromolecular signaling complex formation at the endothelial cell membrane*. Oncotarget, 2014. 5(5): p. 1382-9.
25. Wu, S., et al., *The molecular chaperone gp96/GRP94 interacts with Toll-like receptors and integrins via its C-terminal hydrophobic domain*. J Biol Chem, 2012. 287(9): p. 6735-42.
26. Altmeyer, A., et al., *Tumor-specific cell surface expression of the-KDEL containing, endoplasmic reticular heat shock protein gp96*. Int J Cancer, 1996. 69(4): p. 340-9.

27. Schild, H. and H. G. Rammensee, *gp96—the immune system's Swiss army knife.* Nat Immunol, 2000. 1(2): p. 100-1.
28. Reed, R. C., et al., *GRP94/gp96 elicits ERK activation in murine macrophages. A role for endotoxin contamination in NF-kappa B activation and nitric oxide production.* J Biol Chem, 2003. 278(34): p. 31853-60.
29. Zheng, H., et al., *Cell surface targeting of heat shock protein gp96 induces dendritic cell maturation and anti-tumor immunity.* J Immunol, 2001. 167(12): p. 6731-5.
30. Dai, J., et al., *Cell surface expression of heat shock protein gp96 enhances cross-presentation of cellular antigens and the generation of tumor-specific T cell memory.* Cancer Immun, 2003. 3: p. 1.
31. Berwin, B., et al., *Scavenger receptor-A mediates gp96/GRP94 and calreticulin internalization by antigen presenting cells.* EMBO J, 2003. 22(22): p. 6127-36.
32. Yamamoto, K., et al., *The KDEL receptor mediates a retrieval mechanism that contributes to quality control at the endoplasmic reticulum.* EMBO J, 2001. 20(12): p. 3082-91.
33. Semenza, J. C., et al., *ERD2, a yeast gene required for the receptor-mediated retrieval of luminal ER proteins from the secretory pathway.* Cell, 1990. 61(7): p. 1349-57.
34. Dollins, D. E., et al., *Structures of GRP94-nucleotide complexes reveal mechanistic differences between the hsp90 chaperones.* Mol Cell, 2007. 28(1): p. 41-56.
35. Nemoto, T. and N. Sato, *Oligomeric forms of the 90-kDa heat shock protein.* Biochem J, 1998. 330 (Pt 2): p. 989-95.
36. Han, J. M., et al., *Identification of gp96 as a novel target for treatment of autoimmune disease in mice.* PLoS One, 2010. 5(3): p. e9792.
37. Sagiv, A. and V. Krizhanovsky, *Immunosurveillance of senescent cells: the bright side of the senescence program.* Biogerontology, 2013. 14(6): p. 617-28.
38. Murray, P. J. and T. A. Wynn, *Protective and pathogenic functions of macrophage subsets.* Nat Rev Immunol, 2011. 11(11): p. 723-37.
39. Binder, R. J. and P. K. Srivastava, *Essential role of CD91 in re-presentation of gp96-chaperoned peptides.* Proc Natl Acad Sci USA, 2004. 101(16): p. 6128-33.
40. Binder, R. J., D. K. Han, and P. K. Srivastava, *CD91: a receptor for heat shock protein gp96.* Nat Immunol, 2000. 1(2): p. 151-5.
41. Naylor, R. M., D. J. Baker, and J. M. van Deursen, *Senescent cells: a novel therapeutic target for aging and age-related diseases.* Clin Pharmacol Ther, 2013. 93(1): p. 105-16.
42. Mantovani, A., et al., *Macrophage plasticity and polarization in tissue repair and remodelling.* J Pathol, 2013. 229(2): p. 176-85.

---

What is claimed is:

1. A method of treating a chronic inflammatory disease associated with cellular senescence in a subject in need, said method comprising administering a pharmaceutical agent to the subject, wherein said pharmaceutical agent binds specifically to a cell surface polypeptide set forth in SEQ ID NO: 18, wherein said cell is a senescent cell and accumulation of senescent cells is observed in said disease associated with cellular senescence, and wherein said pharmaceutical agent is an antibody.

2. The method of claim 1, wherein said chronic inflammatory disease associated with cellular senescence is selected from Alzheimer's Disease, diabetes, myocardial infarction, and atherosclerosis; a fibrotic disease including idiopathic pulmonary fibrosis; a pulmonary disease including chronic obstructive pulmonary disease (COPD); liver fibrosis; a disease associated with bone degeneration; wound healing; an age-related disease; or an autoimmune disease.

3. The method of claim 1, wherein the presence of said polypeptide on the cell surface is preferentially present on the surface of senescent cells compared with normal non-senescent cells.

* * * * *

SEQUENCE LISTING

```
<160> NUMBER OF SEQ ID NOS: 46

<210> SEQ ID NO 1
<211> LENGTH: 233
<212> TYPE: PRT
<213> ORGANISM: Homo sapiens

<400> SEQUENCE: 1

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190
```

Glu Leu Tyr Gly Asn Asn Ala Ala Ala Glu Ser Arg Lys Gly Gln Glu
    195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 2
<211> LENGTH: 2575
<212> TYPE: DNA
<213> ORGANISM: Homo sapiens

<400> SEQUENCE: 2

| | |
|---|---|
| ggaggaggaa gcaagcgagg gggctggttc ctgagcttcg caattcctgt gtcgccttct | 60 |
| gggctcccag cctgccgggt cgcatgatcc ctccggccgg agctggtttt tttgccagcc | 120 |
| accgcgaggc cggctgagtt accggcatcc ccgcagccac ctcctctccc gacctgtgat | 180 |
| acaaaagatc ttccgggggc tgcacctgcc tgcctttgcc taaggcggat ttgaatctct | 240 |
| ttctctccct tcagaatctt atcttggctt tggatcttag aagagaatca ctaaccagag | 300 |
| acgagactca gtgagtgagc aggtgttttg acaatggac tggttgagcc catccctatt | 360 |
| ataaaatgt ctcagagcaa ccgggagctg gtggttgact ttctctccta caagcttttcc | 420 |
| cagaaaggat acagctggag tcagtttagt gatgtgaag agaacaggac tgaggcccca | 480 |
| gaagggactg aatcggagat ggagaccccc agtgccatca atggcaaccc atcctggcac | 540 |
| ctggcagaca gccccgcggt gaatggagcc actggccaca gcagcagttt ggatgcccgg | 600 |
| gaggtgatcc ccatggcagc agtaaagcaa gcgctgaggg aggcaggcga cgagtttgaa | 660 |
| ctgcggtacc ggcgggcatt cagtgacctg acatcccagc tccacatcac cccagggaca | 720 |
| gcatatcaga gctttgaaca ggtagtgaat gaactcttcc gggatggggt aaactggggt | 780 |
| cgcattgtgg ccttttttctc cttcggcggg gcactgtgcg tggaaagcgt agacaaggag | 840 |
| atgcaggtat tggtgagtcg gatcgcagct tggatggcca cttacctgaa tgaccaccta | 900 |
| gagccttgga tccaggagaa cggcggctgg gatactttg tggaactcta tgggaacaat | 960 |
| gcagcagccg agagccgaaa gggccaggaa cgcttcaacc gctggttcct gacgggcatg | 1020 |
| actgtggccg gcgtggttct gctgggctca ctcttcagtc ggaaatgacc agacactgac | 1080 |
| catccactct accctcccac cccttctct gctccaccac atcctccgtc agccgccat | 1140 |
| tgccaccagg agaaccacta catgcagccc atgcccacct gcccatcaca gggttgggcc | 1200 |
| cagatctggt cccttgcagc tagttttcta gaatttatca cacttctgtg agaccccac | 1260 |
| acctcagttc ccttggcctc agaattcaca aaatttccac aaaatctgtc aaaggaggc | 1320 |
| tggcaggtat ggaagggttt gtggctgggg gcaggagggc cctacctgat tggtgcaacc | 1380 |
| cttaccccctt agcctccctg aaaatgtttt tctgccaggg agcttgaaag ttttcagaac | 1440 |
| ctcttcccca gaaaggagac tagattgcct tgtttttgat gtttgtggcc tcagaattga | 1500 |
| tcattttccc cccactctcc ccacactaac ctgggttccc tttccttcca tccctacccc | 1560 |
| ctaagagcca tttaggggcc acttttgact agggattcag gctgcttggg ataaagatgc | 1620 |
| aaggaccagg actccctcct cacctctgga ctggctagag tcctcactcc cagtccaaat | 1680 |
| gtcctccaga agcctctggc tagaggccag ccccacccag gagggagggg gctatagcta | 1740 |
| caggaagcac cccatgccaa gctagggtg gcccttgcag ttcagcacca ccctagtccc | 1800 |
| ttcccctccc tggctcccat gaccatactg agggaccaac tgggcccaag acagatgccc | 1860 |

```
cagagctgtt tatggcctca gctgcctcac ttcctacaag agcagcctgt ggcatctttg   1920
ccttgggctg ctcctcatgg tgggttcagg ggactcagcc ctgaggtgaa agggagctat   1980
caggaacagc tatgggagcc ccagggtctt ccctacctca ggcaggaagg caggaagga    2040 gagcctgctg catggggtgg ggtagggctg actagaaggg ccagtcctgc ctggccaggc   2100
agatctgtgc cccatgcctg tccagcctgg gcagccaggc tgccaaggcc agagtggcct   2160
ggccaggagc tcttcaggcc tccctctctc ttctgctcca ccttggcct gtctcatccc    2220 caggggtccc agccaccccg ggctctctgc tgtacatatt tgagactagt ttttattcct   2280
tgtgaagatg atatactatt tttgttaagc gtgtctgtat ttatgtgtga ggagctgctg   2340
gcttgcagtg cgcgtgcacg tggagagctg gtgcccggag attggacggc ctgatgctcc   2400
ctcccctgcc ctggtccagg gaagctggcc gagggtcctg gctcctgagg ggcatctgcc   2460
cctcccccaa cccccacccc acacttgttc cagctctttg aaatagtctg tgtgaaggtg   2520
aaagtgcagt tcagtaataa actgtgttta ctcagtgaaa aaaaaaaaaa aaaaa        2575
```

<210> SEQ ID NO 3
<211> LENGTH: 193
<212> TYPE: PRT
<213> ORGANISM: Homo sapiens

<400> SEQUENCE: 3

```
Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys
```

<210> SEQ ID NO 4
<211> LENGTH: 3621
<212> TYPE: DNA
<213> ORGANISM: Homo sapiens

<400> SEQUENCE: 4

-continued

```
atcacccggc gccgggccct ccctctgccc ccccctttct cctccctcct tccttccctc     60
ccttcctccc tctctccctc cctcccagct cctgcaccag gaaacggccc ggatcccggc    120
agcggcctga cccggctcca cgctggccag gaggatgaaa ggccccagct gggggctcct    180
tgccaccagt gctgtgtctt aagagctgcc atcccggctg gccgcccgga tggcgacccc    240
agcctcggcc ccagacacac gggctctggt ggcagacttt gtaggttata agctgaggca    300
gaagggttat gtctgtggag ctggccccgg ggagggccca gcagctgacc cgctgcacca    360
agccatgcgg gcagctggag atgagttcga gacccgcttc cggcgcacct tctctgatct    420
ggcggctcag ctgcatgtga ccccaggctc agcccaacaa cgcttcaccc aggtctccga    480
tgaacttttt caaggggggcc ccaactgggg ccgccttgta gccttctttg tctttggggc    540
tgcactgtgt gctgagagtg tcaacaagga gatggaacca ctggtgggac aagtgcagga    600
gtggatggtg gcctacctgg agacgcggct ggctgactgg atccacagca gtggggctg     660
ggcggagttc acagctctat acggggacgg ggccctggag gaggcgcggc gtctgcggga    720
ggggaactgg gcatcagtga ggacagtgct gacgggggcc gtggcactgg gggccctggt    780
aactgtaggg gcctttttg ctagcaagtg aaagtccagg gccaggtggg gctaggtgtg    840
gctggggcc aggagagcag gaacagaaca gagaaatgcc cttggaagaa gtggagttgg    900
tggatgggtg ggcatggaac aggatgggca gagaaagggt agtgtgtgag ggagctgagt    960
aggccaggta ggcgattgga agagtgagca ggacacagag gggagggaa tgttttggca   1020
agtttagggg cacaggagat gtagtcgttc cagggctggg ggaggtggga gggatcacgc   1080
ctataggtgt gggcacatga aacgacctgg aacttgcttc acagccctga ggaaggtgga   1140
cttacataag cagctgtatt ccattagatg agtgggattt agggaacgca gaaggcacat   1200
ccctttggaa tggaagctta gggttctca ggtgataggg agaggtggct gttaacagtg   1260
ggctgcttgg acacgcgtgt gcatgtgcac gcatgctggt gtgcatgctg ggctgcctgg   1320
caaatctggt ggtgatggga ttcctcaagg agaaaacatt ccctcttgca atggcaagaa   1380
ctagggcag ttctctgtcc ctcctcccaa cccctccttt cccctgccct tgtcctgatg   1440
cctcaaggct tagagagaaa cattgtatcc agaccgaggg ctctgctgct tctttccaga   1500
aagtgattgg caaggctttg gagagaagag cagttctgca gctggccttg ttccttcatc   1560
atccccttc cttgtgcatt atgcacttgc tgctgcctcc tgggctctga tagaagggca   1620
gggctgttga gcctggatgg gtggaggctt aggtagccgg acctgcctgc caccctcctc   1680
tcccactcag gcacaatggt gcctaaagtg tttccaatct ctgggacctc tgtacccaaa   1740
ctgaaactct aaattggggc cctaactaat tttccttttg aggttgtggg cataagtgct   1800
gatctagaat acagtctggg tcccacactg tgtctcagtg agactgttga tgccttgaga   1860
tgaccatttc agatctgaat cccatgggtg tgagggtgat gggtactcca ggactggcct   1920
atgctgtgtt gtgggctttg gttcggcttt atcaggggcc aggcatatgg gttctagagt   1980
acctaccatg acctagaagc atttatgatt tatttgaagc cacactgttt gcatgggtgt   2040
tacttgtctg tacctcagag tctgaggatg ttaactttgg aactcgcagt cctctagaac   2100
agcttcagat tatggctttt tcttttgagg aagaaattat tcactccaga tgcatgccct   2160
gagccagacc tcactgctgc actttccaag gtgctaagat tgctgctctc caatgctaac   2220
tttctgacac agtgctctag aaccctgcct gtggtcctga gcactgatca ccttagctag   2280
accatggttg actcttcttg gagattttca cttggtccta gaatgtgcca acgtagttgt   2340
gctcgccaga acgtgggacc aaattggcct caggtgttga gtccagactt ctgcttttga   2400
```

```
gagagggctg cacttttca tggtatttct aggggaggtg gtaggctgca tgtgccactt    2460
ggtcttgttg tgagtatgct gacaccagaa actcagagcc agcttgtggc aagcagttgg    2520 ggtgggggt ctctgacttg ctcaggacaa actaggccag tggttttcaa actgcttggc     2580
agagccctga agtttcctag ggggttgcctc aggagtcctt ggggagatga aggggtggg    2640 gagctgagca ggctgggcaa tttgccctca aacagaacag ctccccttgt agctgtctta    2700
catattgggt tcagggtaa gattttattt gcattaaggg gtttgctgct gaaaaaaagt     2760
tggaaaacca ctgactagac catcggctcc aaattggagt ctgtgcttcc ttccccaggt    2820
atggagcaca ctcttcaccc taccctctac cacaggacaa atatccctgt tagcattccc    2880
cgggaccttt agccaagagg agctgcaggg accatggcca ggttaccaaa atgccctgct    2940
ctgaagcctt gacacctggg tgaaagaga ggctgttttc tgaaagggta aagggcttgg     3000
tctggattcc cagaagcata gcttagatgg gaccacagtg ggcaattttg acctgtcctg    3060
cccttcttag cttgaaggga aaccccagag actcttctgt cagggaaaac tagggactct    3120
cttctagagc catatagttc cttgggatta gctcttggcc aagaaggctg agtatggttc    3180
ccaattttta aatccattc attttttaaa aaataaggga aataaatgta attgccattt     3240
ttcaaagatt aagtaggagg agaggggttt cttgctctcc agagcccaaa gggacaaata    3300
gggactttgt ttaggccaag gaaggagcgg aagtagggca actcggtcct gcgattatta   3360
atcccactcc ccacttattc tagggcacac aaacactatt ttacttttt aaaatcataa    3420 aacggcagaa cagatttggt tagtttagaa gaaagaaag ctctataat ataaatctat     3480 attcctgtat ttttatttaa taatttataa ataccaagtt catttgactt ttattttgt    3540 gtaatatgta atgatcgtat taaaaacaat aaataaagcc cagaagttta atgagaagga    3600
ctgaaaaaaa aaaaaaaaaa a                                               3621
```

<210> SEQ ID NO 5
<211> LENGTH: 164
<212> TYPE: PRT
<213> ORGANISM: Homo sapiens

<400> SEQUENCE: 5

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
                20                  25                  30

Asp Cys Asp Ala Leu Met Ala Gly Cys Ile Gln Glu Ala Arg Glu Arg
            35                  40                  45

Trp Asn Phe Asp Phe Val Thr Glu Thr Pro Leu Glu Gly Asp Phe Ala
        50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95

Thr Ser Pro Ala Leu Leu Gln Gly Thr Ala Glu Glu His Val Asp
                100                 105                 110

Leu Ser Leu Ser Cys Thr Leu Val Pro Arg Ser Gly Glu Gln Ala Glu
            115                 120                 125

Gly Ser Pro Gly Gly Pro Gly Asp Ser Gln Gly Arg Lys Arg Arg Gln
        130                 135                 140

Thr Ser Met Thr Asp Phe Tyr His Ser Lys Arg Arg Leu Ile Phe Ser
```

```
145                 150                 155                 160
Lys Arg Lys Pro

<210> SEQ ID NO 6
<211> LENGTH: 2175
<212> TYPE: DNA
<213> ORGANISM: Homo sapiens

<400> SEQUENCE: 6
gttgtatatc agggccgcgc tgagctgcgc cagctgaggt gtgagcagct gccgaagtca      60
gttccttgtg gagccggagc tgggcgcgga ttcgccgagg caccgaggca ctcagaggag     120
gcgccatgtc agaaccggct ggggatgtcc gtcagaaccc atgcggcagc aaggcctgcc     180
gccgcctctt cggcccagtg gacagcgagc agctgagccg cgactgtgat gcgctaatgg     240
cgggctgcat ccaggaggcc cgtgagcgat ggaacttcga ctttgtcacc gagacaccac     300
tggagggtga cttcgcctgg gagcgtgtgc ggggccttgg cctgcccaag ctctaccttc     360
ccacggggcc ccggcgaggc cgggatgagt tgggaggagg caggcggcct ggcacctcac     420
ctgctctgct gcagggggaca gcagaggaag accatgtgga cctgtcactg tcttgtaccc     480
ttgtgcctcg ctcaggggag caggctgaag gtccccagg tggacctgga gactctcagg     540
gtcgaaaacg gcggcagacc agcatgacag atttctacca ctccaaacgc cggctgatct     600
tctccaagag gaagccctaa tccgcccaca ggaagcctgc agtcctggaa gcgcgagggc     660
ctcaaaggcc cgctctacat cttctgcctt agtctcagtt tgtgtgtctt aattattatt     720
tgtgttttaa tttaaacacc tcctcatgta catacccctgg ccgcccctg ccccccagcc     780 tctggcatta gaattattta acaaaaaact aggcggttga atgagaggtt cctaagagtg     840 ctgggcatt ttatttatg aaatactatt taaagcctcc tcatcccgtg ttctcctttt     900
cctctctccc ggaggttggg tgggccggct tcatgccagc tacttcctcc tccccacttg     960
tccgctgggt ggtaccctct ggaggggtgt ggctccttcc catcgctgtc acaggcggtt    1020
atgaaattca ccccctttcc tggacactca gacctgaatt cttttcatt tgagaagtaa    1080 acagatggca ctttgaaggg gcctcaccga gtgggggcat catcaaaaac tttggagtcc    1140
cctcacctcc tctaaggttg gcagggtga ccctgaagtg agcacagcct agggctgagc    1200
tggggacctg gtaccctcct ggctcttgat accccctct gtcttgtgaa ggcaggggga    1260
aggtggggtc ctggagcaga ccaccccgcc tgccctcatg gccctctga cctgcactgg    1320 ggagcccgtc tcagtgttga gccttttccc tctttggctc cctgtacct tttgaggagc    1380 cccagctacc cttcttctcc agctgggctc tgcaattccc ctctgctgct gtccctcccc    1440
cttgtccttt cccttcagta ccctctcagc tccaggtggc tctgaggtgc ctgtcccacc    1500
cccaccccca gctcaatgga ctggaagggg aagggacaca caagaagaag ggcaccctag    1560
ttctacctca ggcagctcaa gcagcgaccg ccccctcctc tagctgtggg ggtgagggtc    1620
ccatgtggtg gcacaggccc ccttgagtgg ggttatctct gtgttagggg tatatgatgg    1680
gggagtagat ctttctagga gggagacact ggcccctcaa atcgtccagc gaccttcctc    1740
atccacccca tccctcccca gttcattgca ctttgattag cagcggaaca aggagtcaga    1800
cattttaaga tggtggcagt agaggctatg gacagggcat gccacgtggg ctcatatggg    1860
gctgggagta gttgtctttc ctggcactaa cgttgagccc ctggaggcac tgaagtgctt    1920
agtgtacttg gagtattggg gtctgacccc aaacaccttc cagctcctgt aacatactgg    1980
cctggactgt tttctctcgg ctccccatgt gtcctggttc ccgtttctcc acctagactg    2040
```

```
taaacctctc gagggcaggg accacaccct gtactgttct gtgtctttca cagctcctcc    2100
cacaatgctg aatatacagc aggtgctcaa taaatgattc ttagtgactt tacttgtaaa    2160
aaaaaaaaaa aaaaa                                                     2175
```

<210> SEQ ID NO 7
<211> LENGTH: 9
<212> TYPE: RNA
<213> ORGANISM: Artificial sequence
<220> FEATURE:
<223> OTHER INFORMATION: Example of a sequences that can be used to form
      the shRNA loop

<400> SEQUENCE: 7 uucaagaga                                                            9

<210> SEQ ID NO 8
<211> LENGTH: 9
<212> TYPE: RNA
<213> ORGANISM: Artificial sequence
<220> FEATURE:
<223> OTHER INFORMATION: Example of a sequences that can be used to form
      the shRNA loop

<400> SEQUENCE: 8 uuuguguag                                                            9

<210> SEQ ID NO 9
<211> LENGTH: 19
<212> TYPE: DNA
<213> ORGANISM: Artificial sequence
<220> FEATURE:
<223> OTHER INFORMATION: Bcl-xl siRNA target sequence

<400> SEQUENCE: 9
cagggacagc atatcagag                                                 19

<210> SEQ ID NO 10
<211> LENGTH: 19
<212> TYPE: DNA
<213> ORGANISM: Artificial sequence
<220> FEATURE:
<223> OTHER INFORMATION: Bcl-xl siRNA target sequence

<400> SEQUENCE: 10
ggagactaga ttgcctttg                                                 19

<210> SEQ ID NO 11
<211> LENGTH: 21
<212> TYPE: DNA
<213> ORGANISM: Artificial sequence
<220> FEATURE:
<223> OTHER INFORMATION: Bcl-xl siRNA target sequence

<400> SEQUENCE: 11
ggcaggcgac gagtttgaac t                                              21

<210> SEQ ID NO 12
<211> LENGTH: 21
<212> TYPE: DNA
<213> ORGANISM: Artificial sequence
<220> FEATURE:
<223> OTHER INFORMATION: Bcl-w siRNA target sequence

<400> SEQUENCE: 12

```
ctcggtcctg cgattattaa t                                              21
```

<210> SEQ ID NO 13
<211> LENGTH: 20
<212> TYPE: DNA
<213> ORGANISM: Artificial sequence
<220> FEATURE:
<223> OTHER INFORMATION: Bcl-w siRNA target sequence

<400> SEQUENCE: 13

```
aagtgcagga gtggatggtg                                                20
```

<210> SEQ ID NO 14
<211> LENGTH: 21
<212> TYPE: DNA
<213> ORGANISM: Artificial sequence
<220> FEATURE:
<223> OTHER INFORMATION: Bcl-w siRNA target sequence

<400> SEQUENCE: 14

```
aagggttatg tctgtggagc t                                              21
```

<210> SEQ ID NO 15
<211> LENGTH: 20
<212> TYPE: DNA
<213> ORGANISM: Artificial sequence
<220> FEATURE:
<223> OTHER INFORMATION: CDKN1A - cyclin-dependent kinase inhibitor 1A
      (p21, Cip1) siRNA target sequence

<400> SEQUENCE: 15

```
cttcgacttt gtcaccgaga                                                20
```

<210> SEQ ID NO 16
<211> LENGTH: 21
<212> TYPE: DNA
<213> ORGANISM: Artificial sequence
<220> FEATURE:
<223> OTHER INFORMATION: CDKN1A - cyclin-dependent kinase inhibitor 1A
      (p21, Cip1) siRNA target sequence

<400> SEQUENCE: 16

```
cagtttgtgt gtcttaatta t                                              21
```

<210> SEQ ID NO 17
<211> LENGTH: 21
<212> TYPE: DNA
<213> ORGANISM: Artificial sequence
<220> FEATURE:
<223> OTHER INFORMATION: CDKN1A - cyclin-dependent kinase inhibitor 1A
      (p21, Cip1) siRNA target sequence

<400> SEQUENCE: 17

```
ctggcattag aattatttaa a                                              21
```

<210> SEQ ID NO 18
<211> LENGTH: 803
<212> TYPE: PRT
<213> ORGANISM: Homo sapiens

<400> SEQUENCE: 18

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

-continued

Glu Asp Leu Gly Lys Ser Arg Glu Gly Ser Arg Thr Asp Glu Val
            35                  40                  45

Val Gln Arg Glu Glu Ala Ile Gln Leu Asp Gly Leu Asn Ala Ser
 50                  55                  60

Gln Ile Arg Glu Leu Arg Glu Lys Ser Glu Lys Phe Ala Phe Gln Ala
 65                  70                  75                  80

Glu Val Asn Arg Met Met Lys Leu Ile Ile Asn Ser Leu Tyr Lys Asn
                     85                  90                  95

Lys Glu Ile Phe Leu Arg Glu Leu Ile Ser Asn Ala Ser Asp Ala Leu
                100                 105                 110

Asp Lys Ile Arg Leu Ile Ser Leu Thr Asp Glu Asn Ala Leu Ser Gly
            115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
                180                 185                 190

Gly Gln Phe Gly Val Gly Phe Tyr Ser Ala Phe Leu Val Ala Asp Lys
            195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
            275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
                355                 360                 365

Pro Met Ala Tyr Ile His Phe Thr Ala Glu Gly Glu Val Thr Phe Lys
370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
            435                 440                 445

Glu Thr Leu Gln Gln His Lys Leu Leu Lys Val Ile Arg Lys Lys Leu

```
                450             455             460
Val Arg Lys Thr Leu Asp Met Ile Lys Ile Ala Asp Asp Lys Tyr
465                 470                 475                 480

Asn Asp Thr Phe Trp Lys Glu Phe Gly Thr Asn Ile Lys Leu Gly Val
                    485                 490                 495

Ile Glu Asp His Ser Asn Arg Thr Arg Leu Ala Lys Leu Leu Arg Phe
                500                 505                 510

Gln Ser Ser His His Pro Thr Asp Ile Thr Ser Leu Asp Gln Tyr Val
            515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
                580                 585                 590

Lys Glu Gly Val Lys Phe Asp Glu Ser Glu Lys Thr Lys Glu Ser Arg
            595                 600                 605

Glu Ala Val Glu Lys Glu Phe Glu Pro Leu Leu Asn Trp Met Lys Asp
        610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
            675                 680                 685

Pro Arg His Pro Leu Ile Arg Asp Met Leu Arg Arg Ile Lys Glu Asp
        690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
                740                 745                 750

Ala Lys Val Glu Glu Glu Pro Glu Glu Glu Pro Glu Glu Thr Ala Glu
            755                 760                 765

Asp Thr Thr Glu Asp Thr Glu Gln Asp Glu Asp Glu Glu Met Asp Val
        770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 19
<211> LENGTH: 337
<212> TYPE: PRT
<213> ORGANISM: Homo sapiens

<400> SEQUENCE: 19

Met Gly Lys Asp Tyr Tyr Cys Ile Leu Gly Ile Glu Lys Gly Ala Ser
1                   5                   10                  15

Asp Glu Asp Ile Lys Lys Ala Tyr Arg Lys Gln Ala Leu Lys Phe His
```

```
                20                  25                  30
Pro Asp Lys Asn Lys Ser Pro Gln Ala Glu Glu Lys Phe Lys Glu Val
            35                  40                  45
Ala Glu Ala Tyr Glu Val Leu Ser Asp Pro Lys Arg Glu Ile Tyr
    50                  55                  60
Asp Gln Phe Gly Glu Gly Leu Lys Gly Ala Gly Gly Thr Asp
65                  70                  75                  80
Gly Gln Gly Gly Thr Phe Arg Tyr Thr Phe His Gly Asp Pro His Ala
                85                  90                  95
Thr Phe Ala Ala Phe Phe Gly Gly Ser Asn Pro Phe Glu Ile Phe Phe
            100                 105                 110
Gly Arg Arg Met Gly Gly Arg Asp Ser Glu Glu Met Glu Ile Asp
        115                 120                 125
Gly Asp Pro Phe Ser Ala Phe Gly Phe Ser Met Asn Gly Tyr Pro Arg
        130                 135                 140
Asp Arg Asn Ser Val Gly Pro Ser Arg Leu Lys Gln Asp Pro Pro Val
145                 150                 155                 160
Ile His Glu Leu Arg Val Ser Leu Glu Glu Ile Tyr Ser Gly Cys Thr
                165                 170                 175
Lys Arg Met Lys Ile Ser Arg Lys Arg Leu Asn Ala Asp Gly Arg Ser
            180                 185                 190
Tyr Arg Ser Glu Asp Lys Ile Leu Thr Ile Glu Ile Lys Lys Gly Trp
        195                 200                 205
Lys Glu Gly Thr Lys Ile Thr Phe Pro Arg Glu Gly Asp Glu Thr Pro
    210                 215                 220
Asn Ser Ile Pro Ala Asp Ile Val Phe Ile Ile Lys Asp Lys Asp His
225                 230                 235                 240
Pro Lys Phe Lys Arg Asp Gly Ser Asn Ile Ile Tyr Thr Ala Lys Ile
                245                 250                 255
Ser Leu Arg Glu Ala Leu Cys Gly Cys Ser Ile Asn Val Pro Thr Leu
            260                 265                 270
Asp Gly Arg Asn Ile Pro Met Ser Val Asn Asp Ile Val Lys Pro Gly
        275                 280                 285
Met Arg Arg Arg Ile Ile Gly Tyr Gly Leu Pro Phe Pro Lys Asn Pro
        290                 295                 300
Asp Gln Arg Gly Asp Leu Leu Ile Glu Phe Glu Val Ser Phe Pro Asp
305                 310                 315                 320
Thr Ile Ser Ser Ser Lys Glu Val Leu Arg Lys His Leu Pro Ala
                325                 330                 335
Ser

<210> SEQ ID NO 20
<211> LENGTH: 479
<212> TYPE: PRT
<213> ORGANISM: Homo sapiens

<400> SEQUENCE: 20

Met Asp Glu Thr Ser Pro Leu Val Ser Pro Glu Arg Ala Gln Pro Pro
1               5                   10                  15
Asp Tyr Thr Phe Pro Ser Gly Ser Gly Ala His Phe Pro Gln Val Pro
            20                  25                  30
Gly Gly Ala Val Arg Val Ala Ala Ala Gly Ser Gly Pro Ser Pro
        35                  40                  45
Pro Gly Ser Pro Gly His Asp Arg Glu Arg Gln Pro Leu Leu Asp Arg
```

```
                      50                  55                  60
Ala Arg Gly Ala Ala Ala Gln Gly Gln Thr Gln Thr Val Ala Ala Gln
 65                      70                  75                  80

Ala Gln Ala Leu Ala Ala Gln Ala Ala Ala Ala His Ala Ala Gln
                     85                  90                  95

Ala His Arg Glu Arg Asn Glu Phe Pro Glu Asp Pro Glu Phe Glu Ala
                    100                 105                 110

Val Val Arg Gln Ala Glu Leu Ala Ile Glu Arg Cys Ile Phe Pro Glu
                    115                 120                 125

Arg Ile Tyr Gln Gly Ser Ser Gly Ser Tyr Phe Val Lys Asp Pro Gln
                    130                 135                 140

Gly Arg Ile Ile Ala Val Phe Lys Pro Lys Asn Glu Glu Pro Tyr Gly
145                     150                 155                 160

His Leu Asn Pro Lys Trp Thr Lys Trp Leu Gln Lys Leu Cys Cys Pro
                    165                 170                 175

Cys Cys Phe Gly Arg Asp Cys Leu Val Leu Asn Gln Gly Tyr Leu Ser
                    180                 185                 190

Glu Ala Gly Ala Ser Leu Val Asp Gln Lys Leu Glu Leu Asn Ile Val
                    195                 200                 205

Pro Arg Thr Lys Val Val Tyr Leu Ala Ser Glu Thr Phe Asn Tyr Ser
                    210                 215                 220

Ala Ile Asp Arg Val Lys Ser Arg Gly Lys Arg Leu Ala Leu Glu Lys
225                     230                 235                 240

Val Pro Lys Val Gly Gln Arg Phe Asn Arg Ile Gly Leu Pro Pro Lys
                    245                 250                 255

Val Gly Ser Phe Gln Leu Phe Val Glu Gly Tyr Lys Asp Ala Asp Tyr
                    260                 265                 270

Trp Leu Arg Arg Phe Glu Ala Glu Pro Leu Pro Glu Asn Thr Asn Arg
                    275                 280                 285

Gln Leu Leu Leu Gln Phe Glu Arg Leu Val Val Leu Asp Tyr Ile Ile
                    290                 295                 300

Arg Asn Thr Asp Arg Gly Asn Asp Asn Trp Leu Ile Lys Tyr Asp Cys
305                     310                 315                 320

Pro Met Asp Ser Ser Ser Arg Asp Thr Asp Trp Val Val Lys
                    325                 330                 335

Glu Pro Val Ile Lys Val Ala Ala Ile Asp Asn Gly Leu Ala Phe Pro
                    340                 345                 350

Leu Lys His Pro Asp Ser Trp Arg Ala Tyr Pro Phe Tyr Trp Ala Trp
                    355                 360                 365

Leu Pro Gln Ala Lys Val Pro Phe Ser Gln Glu Ile Lys Asp Leu Ile
                    370                 375                 380

Leu Pro Lys Ile Ser Asp Pro Asn Phe Val Lys Asp Leu Glu Glu Asp
385                     390                 395                 400

Leu Tyr Glu Leu Phe Lys Lys Asp Pro Gly Phe Asp Arg Gly Gln Phe
                    405                 410                 415

His Lys Gln Ile Ala Val Met Arg Gly Gln Ile Leu Asn Leu Thr Gln
                    420                 425                 430

Ala Leu Lys Asp Asn Lys Ser Pro Leu His Leu Val Gln Met Pro Pro
                    435                 440                 445

Val Ile Val Glu Thr Ala Arg Ser His Gln Arg Ser Ser Glu Ser
                    450                 455                 460

Tyr Thr Gln Ser Phe Gln Ser Arg Lys Pro Phe Phe Ser Trp Trp
465                     470                 475
```

<210> SEQ ID NO 21
<211> LENGTH: 651
<212> TYPE: PRT
<213> ORGANISM: Homo sapiens

<400> SEQUENCE: 21

```
Met Ala Gly His Pro Trp His Gly Thr Ala Ala Leu Ala Ser Ser Gln
1               5                   10                  15

Ala Trp Arg Asp Gly Arg Glu Arg Gln Ala Leu Val Ser Cys Arg Ala
            20                  25                  30

Leu Tyr Thr Tyr Glu Asp Gly Ser Asp Asp Leu Lys Leu Ala Ala Ser
        35                  40                  45

Gly Glu Gly Gly Leu Gln Glu Leu Ser Gly His Phe Glu Asn Gln Lys
    50                  55                  60

Val Met Tyr Gly Phe Cys Ser Val Lys Asp Ser Gln Ala Ala Leu Pro
65                  70                  75                  80

Lys Tyr Val Leu Ile Asn Trp Val Gly Glu Asp Val Pro Asp Ala Arg
                85                  90                  95

Lys Cys Ala Cys Ala Ser His Val Ala Lys Val Ala Glu Phe Phe Gln
            100                 105                 110

Gly Val Asp Val Ile Val Asn Ala Ser Ser Val Glu Asp Ile Asp Ala
        115                 120                 125

Gly Ala Ile Gly Gln Arg Leu Ser Asn Gly Leu Ala Arg Leu Ser Ser
    130                 135                 140

Pro Val Leu His Arg Leu Arg Leu Arg Glu Asp Glu Asn Ala Glu Pro
145                 150                 155                 160

Val Gly Thr Thr Tyr Gln Lys Thr Asp Ala Ala Val Glu Met Lys Arg
                165                 170                 175

Ile Asn Arg Glu Gln Phe Trp Glu Gln Ala Lys Lys Glu Glu Glu Leu
            180                 185                 190

Arg Lys Glu Glu Arg Lys Lys Ala Leu Asp Glu Arg Leu Arg Phe
        195                 200                 205

Glu Gln Glu Arg Met Glu Gln Glu Arg Gln Glu Gln Glu Glu Arg Glu
    210                 215                 220

Arg Arg Tyr Arg Glu Arg Glu Gln Gln Ile Glu Glu His Arg Arg Lys
225                 230                 235                 240

Gln Gln Thr Leu Glu Ala Glu Ala Lys Arg Arg Leu Lys Glu Gln
                245                 250                 255

Ser Ile Phe Gly Asp His Arg Asp Glu Glu Glu Thr His Met Lys
            260                 265                 270

Lys Ser Glu Ser Glu Val Glu Glu Ala Ala Ile Ile Ala Gln Arg
        275                 280                 285

Pro Asp Asn Pro Arg Glu Phe Phe Lys Gln Gln Glu Arg Val Ala Ser
    290                 295                 300

Ala Ser Ala Gly Ser Cys Asp Val Pro Ser Pro Phe Asn His Arg Pro
305                 310                 315                 320

Gly Ser His Leu Asp Ser His Arg Arg Met Ala Pro Thr Pro Ile Pro
                325                 330                 335

Thr Arg Ser Pro Ser Asp Ser Ser Thr Ala Ser Thr Pro Val Ala Glu
            340                 345                 350

Gln Ile Glu Arg Ala Leu Asp Glu Val Thr Ser Ser Gln Pro Pro Pro
        355                 360                 365

Leu Pro Pro Pro Pro Pro Pro Ala Gln Glu Thr Gln Glu Pro Ser Pro
```

```
                 370               375               380
Ile Leu Asp Ser Glu Glu Thr Arg Ala Ala Pro Gln Ala Trp Ala
385                 390               395               400

Gly Pro Met Glu Glu Pro Gln Ala Gln Ala Pro Pro Arg Gly Pro
                405               410               415

Gly Ser Pro Ala Glu Asp Leu Met Phe Met Glu Ser Ala Glu Gln Ala
                420               425               430

Val Leu Ala Ala Pro Val Glu Pro Ala Thr Ala Asp Thr Glu Ile
        435               440               445

His Asp Ala Ala Asp Thr Ile Glu Thr Asp Thr Ala Thr Ala Asp Thr
        450               455               460

Thr Val Ala Asn Asn Val Pro Pro Ala Ala Thr Ser Leu Ile Asp Leu
465               470               475               480

Trp Pro Gly Asn Gly Glu Gly Ala Ser Thr Leu Gln Gly Glu Pro Arg
                485               490               495

Ala Pro Thr Pro Pro Ser Gly Thr Glu Val Thr Leu Ala Glu Val Pro
                500               505               510

Leu Leu Asp Glu Val Ala Pro Glu Pro Leu Leu Pro Ala Gly Glu Gly
        515               520               525

Cys Ala Thr Leu Leu Asn Phe Asp Glu Leu Pro Glu Pro Pro Ala Thr
        530               535               540

Phe Cys Asp Pro Glu Glu Val Glu Gly Glu Ser Leu Ala Ala Pro Gln
545               550               555               560

Thr Pro Thr Leu Pro Ser Ala Leu Glu Glu Leu Glu Gln Glu Gln Glu
                565               570               575

Pro Glu Pro His Leu Leu Thr Asn Gly Glu Thr Thr Gln Lys Glu Gly
                580               585               590

Thr Gln Ala Ser Glu Gly Tyr Phe Ser Gln Ser Gln Glu Glu Phe
        595               600               605

Ala Gln Ser Glu Glu Leu Cys Ala Lys Ala Pro Pro Val Phe Tyr
        610               615               620

Asn Lys Pro Pro Glu Ile Asp Ile Thr Cys Trp Asp Ala Asp Pro Val
625               630               635               640

Pro Glu Glu Glu Glu Gly Phe Glu Gly Gly Asp
                645               650
```

<210> SEQ ID NO 22
<211> LENGTH: 525
<212> TYPE: PRT
<213> ORGANISM: Homo sapiens

<400> SEQUENCE: 22

```
Met Leu Leu Pro Leu Leu Leu Leu Pro Met Cys Trp Ala Val Glu
1               5                  10                  15

Val Lys Arg Pro Arg Gly Val Ser Leu Thr Asn His His Phe Tyr Asp
                20                  25                  30

Glu Ser Lys Pro Phe Thr Cys Leu Asp Gly Ser Ala Thr Ile Pro Phe
        35                  40                  45

Asp Gln Val Asn Asp Asp Tyr Cys Asp Cys Lys Asp Gly Ser Asp Glu
        50                  55                  60

Pro Gly Thr Ala Ala Cys Pro Asn Gly Ser Phe His Cys Thr Asn Thr
65                  70                  75                  80

Gly Tyr Lys Pro Leu Tyr Ile Pro Ser Asn Arg Val Asn Asp Gly Val
                85                  90                  95
```

-continued

```
Cys Asp Cys Cys Asp Gly Thr Asp Glu Tyr Asn Ser Gly Val Ile Cys
            100                 105                 110
Glu Asn Thr Cys Lys Glu Lys Gly Arg Lys Glu Arg Glu Ser Leu Gln
        115                 120                 125
Gln Met Ala Glu Val Thr Arg Glu Gly Phe Arg Leu Lys Lys Ile Leu
    130                 135                 140
Ile Glu Asp Trp Lys Lys Ala Arg Glu Glu Lys Gln Lys Lys Leu Ile
145                 150                 155                 160
Glu Leu Gln Ala Gly Lys Lys Ser Leu Glu Asp Gln Val Glu Met Leu
                165                 170                 175
Arg Thr Val Lys Glu Glu Ala Glu Lys Pro Glu Arg Glu Ala Lys Glu
            180                 185                 190
Gln His Gln Lys Leu Trp Glu Glu Gln Leu Ala Ala Ala Lys Ala Gln
        195                 200                 205
Gln Glu Gln Glu Leu Ala Ala Asp Ala Phe Lys Glu Leu Asp Asp Asp
    210                 215                 220
Met Asp Gly Thr Val Ser Val Thr Glu Leu Gln Thr His Pro Glu Leu
225                 230                 235                 240
Asp Thr Asp Gly Asp Gly Ala Leu Ser Glu Ala Glu Ala Gln Ala Leu
                245                 250                 255
Leu Ser Gly Asp Thr Gln Thr Asp Ala Thr Ser Phe Tyr Asp Arg Val
            260                 265                 270
Trp Ala Ala Ile Arg Asp Lys Tyr Arg Ser Glu Ala Leu Pro Thr Asp
        275                 280                 285
Leu Pro Ala Pro Ser Ala Pro Asp Leu Thr Glu Pro Lys Glu Glu Gln
    290                 295                 300
Pro Pro Val Pro Ser Ser Pro Thr Glu Glu Glu Glu Glu Glu Glu Glu
305                 310                 315                 320
Glu Glu Glu Glu Glu Ala Glu Glu Glu Glu Glu Glu Glu Asp Ser Glu
                325                 330                 335
Val Gln Gly Glu Gln Pro Lys Pro Ala Ser Pro Ala Glu Glu Asp Lys
            340                 345                 350
Met Pro Pro Tyr Asp Glu Gln Thr Gln Ala Phe Ile Asp Ala Ala Gln
        355                 360                 365
Glu Ala Arg Asn Lys Phe Glu Glu Ala Glu Arg Ser Leu Lys Asp Met
    370                 375                 380
Glu Glu Ser Ile Arg Asn Leu Glu Gln Glu Ile Ser Phe Asp Phe Gly
385                 390                 395                 400
Pro Asn Gly Glu Phe Ala Tyr Leu Tyr Ser Gln Cys Tyr Glu Leu Thr
                405                 410                 415
Thr Asn Glu Tyr Val Tyr Arg Leu Cys Pro Phe Lys Leu Val Ser Gln
            420                 425                 430
Lys Pro Lys Leu Gly Gly Ser Pro Thr Ser Leu Gly Thr Trp Gly Ser
        435                 440                 445
Trp Ile Gly Pro Asp His Asp Lys Phe Ser Ala Met Lys Tyr Glu Gln
    450                 455                 460
Gly Thr Gly Cys Trp Gln Gly Pro Asn Arg Ser Thr Thr Val Arg Leu
465                 470                 475                 480
Leu Cys Gly Lys Glu Thr Met Val Thr Ser Thr Thr Glu Pro Ser Arg
                485                 490                 495
Cys Glu Tyr Leu Met Glu Leu Met Thr Pro Ala Ala Cys Pro Glu Pro
            500                 505                 510
Pro Pro Glu Ala Pro Thr Glu Asp Asp His Asp Glu Leu
```

<210> SEQ ID NO 23
<211> LENGTH: 2167
<212> TYPE: PRT
<213> ORGANISM: Homo sapiens

<400> SEQUENCE: 23

```
Met Thr Thr Thr Val Ala Thr Asp Tyr Asp Asn Ile Glu Ile Gln Gln
1               5                   10                  15

Gln Tyr Ser Asp Val Asn Asn Arg Trp Asp Val Asp Asp Trp Asp Asn
            20                  25                  30

Glu Asn Ser Ser Ala Arg Leu Phe Glu Arg Ser Arg Ile Lys Ala Leu
        35                  40                  45

Ala Asp Glu Arg Glu Ala Val Gln Lys Lys Thr Phe Thr Lys Trp Val
    50                  55                  60

Asn Ser His Leu Ala Arg Val Ser Cys Arg Ile Thr Asp Leu Tyr Thr
65                  70                  75                  80

Asp Leu Arg Asp Gly Arg Met Leu Ile Lys Leu Leu Glu Val Leu Ser
                85                  90                  95

Gly Glu Arg Leu Pro Lys Pro Thr Lys Gly Arg Met Arg Ile His Cys
            100                 105                 110

Leu Glu Asn Val Asp Lys Ala Leu Gln Phe Leu Lys Glu Gln Arg Val
        115                 120                 125

His Leu Glu Asn Met Gly Ser His Asp Ile Val Asp Gly Asn His Arg
    130                 135                 140

Leu Thr Leu Gly Leu Ile Trp Thr Ile Ile Leu Arg Phe Gln Ile Gln
145                 150                 155                 160

Asp Ile Ser Val Glu Thr Glu Asp Asn Lys Glu Lys Lys Ser Ala Lys
                165                 170                 175

Asp Ala Leu Leu Leu Trp Cys Gln Met Lys Thr Ala Gly Tyr Pro Asn
            180                 185                 190

Val Asn Ile His Asn Phe Thr Thr Ser Trp Arg Asp Gly Met Ala Phe
        195                 200                 205

Asn Ala Leu Ile His Lys His Arg Pro Asp Leu Ile Asp Phe Asp Lys
    210                 215                 220

Leu Lys Lys Ser Asn Ala His Tyr Asn Leu Gln Asn Ala Phe Asn Leu
225                 230                 235                 240

Ala Glu Gln His Leu Gly Leu Thr Lys Leu Leu Asp Pro Glu Asp Ile
                245                 250                 255

Ser Val Asp His Pro Asp Glu Lys Ser Ile Ile Thr Tyr Val Val Thr
            260                 265                 270

Tyr Tyr His Tyr Phe Ser Lys Met Lys Ala Leu Ala Val Glu Gly Lys
        275                 280                 285

Arg Ile Gly Lys Val Leu Asp Asn Ala Ile Glu Thr Glu Lys Met Ile
    290                 295                 300

Glu Lys Tyr Glu Ser Leu Ala Ser Asp Leu Leu Glu Trp Ile Glu Gln
305                 310                 315                 320

Thr Ile Ile Ile Leu Asn Asn Arg Lys Phe Ala Asn Ser Leu Val Gly
                325                 330                 335

Val Gln Gln Gln Leu Gln Ala Phe Asn Thr Tyr Arg Thr Val Glu Lys
            340                 345                 350

Pro Pro Lys Phe Thr Glu Lys Gly Asn Leu Glu Val Leu Leu Phe Thr
        355                 360                 365
```

-continued

```
Ile Gln Ser Lys Met Arg Ala Asn Asn Gln Lys Val Tyr Met Pro Arg
370                 375                 380
Glu Gly Lys Leu Ile Ser Asp Ile Asn Lys Ala Trp Glu Arg Leu Glu
385                 390                 395                 400
Lys Ala Glu His Glu Arg Glu Leu Ala Leu Arg Asn Glu Leu Ile Arg
                405                 410                 415
Gln Glu Lys Leu Glu Gln Leu Ala Arg Arg Phe Asp Arg Lys Ala Ala
            420                 425                 430
Met Arg Glu Thr Trp Leu Ser Glu Asn Gln Arg Leu Val Ser Gln Asp
        435                 440                 445
Asn Phe Gly Phe Asp Leu Pro Ala Val Glu Ala Thr Lys Lys His
450                 455                 460
Glu Ala Ile Glu Thr Asp Ile Ala Ala Tyr Glu Glu Arg Val Gln Ala
465                 470                 475                 480
Val Val Ala Val Ala Arg Glu Leu Glu Ala Glu Asn Tyr His Asp Ile
                485                 490                 495
Lys Arg Ile Thr Ala Arg Lys Asp Asn Val Ile Arg Leu Trp Glu Tyr
                500                 505                 510
Leu Leu Glu Leu Leu Arg Ala Arg Arg Gln Arg Leu Glu Met Asn Leu
            515                 520                 525
Gly Leu Gln Lys Ile Phe Gln Glu Met Leu Tyr Ile Met Asp Trp Met
        530                 535                 540
Asp Glu Met Lys Val Leu Val Leu Ser Gln Asp Tyr Gly Lys His Leu
545                 550                 555                 560
Leu Gly Val Glu Asp Leu Leu Gln Lys His Thr Leu Val Glu Ala Asp
                565                 570                 575
Ile Gly Ile Gln Ala Glu Arg Val Arg Gly Val Asn Ala Ser Ala Gln
                580                 585                 590
Lys Phe Ala Thr Asp Gly Glu Gly Tyr Lys Pro Cys Asp Pro Gln Val
            595                 600                 605
Ile Arg Asp Arg Val Ala His Met Glu Phe Cys Tyr Gln Glu Leu Cys
        610                 615                 620
Gln Leu Ala Ala Glu Arg Arg Ala Arg Leu Glu Glu Ser Arg Arg Leu
625                 630                 635                 640
Trp Lys Phe Phe Trp Glu Met Ala Glu Glu Gly Trp Ile Arg Glu
                645                 650                 655
Lys Glu Lys Ile Leu Ser Ser Asp Tyr Gly Lys Asp Leu Thr Ser
                660                 665                 670
Val Met Arg Leu Leu Ser Lys His Arg Ala Phe Glu Asp Glu Met Ser
            675                 680                 685
Gly Arg Ser Gly His Phe Glu Gln Ala Ile Lys Glu Gly Glu Asp Met
        690                 695                 700
Ile Ala Glu Glu His Phe Gly Ser Glu Lys Ile Arg Glu Arg Ile Ile
705                 710                 715                 720
Tyr Ile Arg Glu Gln Trp Ala Asn Leu Glu Gln Leu Ser Ala Ile Arg
                725                 730                 735
Lys Lys Arg Leu Glu Glu Ala Ser Leu Leu His Gln Phe Gln Ala Asp
            740                 745                 750
Ala Asp Asp Ile Asp Ala Trp Met Leu Asp Ile Leu Lys Ile Val Ser
        755                 760                 765
Ser Ser Asp Val Gly His Asp Glu Tyr Ser Thr Gln Ser Leu Val Lys
770                 775                 780
Lys His Lys Asp Val Ala Glu Glu Ile Ala Asn Tyr Arg Pro Thr Leu
```

-continued

```
            785                 790                 795                 800
Asp Thr Leu His Glu Gln Ala Ser Ala Leu Pro Gln Glu His Ala Glu
                        805                 810                 815

Ser Pro Asp Val Arg Gly Arg Leu Ser Gly Ile Glu Glu Arg Tyr Lys
                        820                 825                 830

Glu Val Ala Glu Leu Thr Arg Leu Arg Lys Gln Ala Leu Gln Asp Thr
                        835                 840                 845

Leu Ala Leu Tyr Lys Met Phe Ser Glu Ala Asp Ala Cys Glu Leu Trp
            850                 855                 860

Ile Asp Glu Lys Glu Gln Trp Leu Asn Asn Met Gln Ile Pro Glu Lys
865                 870                 875                 880

Leu Glu Asp Leu Glu Val Ile Gln His Arg Phe Glu Ser Leu Glu Pro
                        885                 890                 895

Glu Met Asn Asn Gln Ala Ser Arg Val Ala Val Val Asn Gln Ile Ala
                        900                 905                 910

Arg Gln Leu Met His Ser Gly His Pro Ser Glu Lys Glu Ile Lys Ala
                        915                 920                 925

Gln Gln Asp Lys Leu Asn Thr Arg Trp Ser Gln Phe Arg Glu Leu Val
            930                 935                 940

Asp Arg Lys Lys Asp Ala Leu Leu Ser Ala Leu Ser Ile Gln Asn Tyr
945                 950                 955                 960

His Leu Glu Cys Asn Glu Thr Lys Ser Trp Ile Arg Glu Lys Thr Lys
                        965                 970                 975

Val Ile Glu Ser Thr Gln Asp Leu Gly Asn Asp Leu Ala Gly Val Met
                        980                 985                 990

Ala Leu Gln Arg Lys Leu Thr Gly Met Glu Arg Asp Leu Val Ala Ile
            995                 1000                1005

Glu Ala Lys Leu Ser Asp Leu Gln Lys Glu Ala Glu Lys Leu Glu
            1010                1015                1020

Ser Glu His Pro Asp Gln Ala Gln Ala Ile Leu Ser Arg Leu Ala
            1025                1030                1035

Glu Ile Ser Asp Val Trp Glu Glu Met Lys Thr Thr Leu Lys Asn
            1040                1045                1050

Arg Glu Ala Ser Leu Gly Glu Ala Ser Lys Leu Gln Gln Phe Leu
            1055                1060                1065

Arg Asp Leu Asp Asp Phe Gln Ser Trp Leu Ser Arg Thr Gln Thr
            1070                1075                1080

Ala Ile Ala Ser Glu Asp Met Pro Asn Thr Leu Thr Glu Ala Glu
            1085                1090                1095

Lys Leu Leu Thr Gln His Glu Asn Ile Lys Asn Glu Ile Asp Asn
            1100                1105                1110

Tyr Glu Glu Asp Tyr Gln Lys Met Arg Asp Met Gly Glu Met Val
            1115                1120                1125

Thr Gln Gly Gln Thr Asp Ala Gln Tyr Met Phe Leu Arg Gln Arg
            1130                1135                1140

Leu Gln Ala Leu Asp Thr Gly Trp Asn Glu Leu His Lys Met Trp
            1145                1150                1155

Glu Asn Arg Gln Asn Leu Leu Ser Gln Ser His Ala Tyr Gln Gln
            1160                1165                1170

Phe Leu Arg Asp Thr Lys Gln Ala Glu Ala Phe Leu Asn Asn Gln
            1175                1180                1185

Glu Tyr Val Leu Ala His Thr Glu Met Pro Thr Thr Leu Glu Gly
            1190                1195                1200
```

-continued

Ala Glu Ala Ala Ile Lys Lys Gln Glu Asp Phe Met Thr Thr Met
1205             1210                 1215

Asp Ala Asn Glu Glu Lys Ile Asn Ala Val Val Glu Thr Gly Arg
1220             1225                 1230

Arg Leu Val Ser Asp Gly Asn Ile Asn Ser Asp Arg Ile Gln Glu
1235             1240                 1245

Lys Val Asp Ser Ile Asp Asp Arg His Arg Lys Asn Arg Glu Thr
1250             1255                 1260

Ala Ser Glu Leu Leu Met Arg Leu Lys Asp Asn Arg Asp Leu Gln
1265             1270                 1275

Lys Phe Leu Gln Asp Cys Gln Glu Leu Ser Leu Trp Ile Asn Glu
1280             1285                 1290

Lys Met Leu Thr Ala Gln Asp Met Ser Tyr Asp Glu Ala Arg Asn
1295             1300                 1305

Leu His Ser Lys Trp Leu Lys His Gln Ala Phe Met Ala Glu Leu
1310             1315                 1320

Ala Ser Asn Lys Glu Trp Leu Asp Lys Ile Glu Lys Glu Gly Met
1325             1330                 1335

Gln Leu Ile Ser Glu Lys Pro Glu Thr Glu Ala Val Val Lys Glu
1340             1345                 1350

Lys Leu Thr Gly Leu His Lys Met Trp Glu Val Leu Glu Ser Thr
1355             1360                 1365

Thr Gln Thr Lys Ala Gln Arg Leu Phe Asp Ala Asn Lys Ala Glu
1370             1375                 1380

Leu Phe Thr Gln Ser Cys Ala Asp Leu Asp Lys Trp Leu His Gly
1385             1390                 1395

Leu Glu Ser Gln Ile Gln Ser Asp Asp Tyr Gly Lys Asp Leu Thr
1400             1405                 1410

Ser Val Asn Ile Leu Leu Lys Lys Gln Gln Met Leu Glu Asn Gln
1415             1420                 1425

Met Glu Val Arg Lys Lys Glu Ile Glu Glu Leu Gln Ser Gln Ala
1430             1435                 1440

Gln Ala Leu Ser Gln Glu Gly Lys Ser Thr Asp Glu Val Asp Ser
1445             1450                 1455

Lys Arg Leu Thr Val Gln Thr Lys Phe Met Glu Leu Leu Glu Pro
1460             1465                 1470

Leu Asn Glu Arg Lys His Asn Leu Leu Ala Ser Lys Glu Ile His
1475             1480                 1485

Gln Phe Asn Arg Asp Val Glu Asp Glu Ile Leu Trp Val Gly Glu
1490             1495                 1500

Arg Met Pro Leu Ala Thr Ser Thr Asp His Gly His Asn Leu Gln
1505             1510                 1515

Thr Val Gln Leu Leu Ile Lys Lys Asn Gln Thr Leu Gln Lys Glu
1520             1525                 1530

Ile Gln Gly His Gln Pro Arg Ile Asp Asp Ile Phe Glu Arg Ser
1535             1540                 1545

Gln Asn Ile Val Thr Asp Ser Ser Ser Leu Ser Ala Glu Ala Ile
1550             1555                 1560

Arg Gln Arg Leu Ala Asp Leu Lys Gln Leu Trp Gly Leu Leu Ile
1565             1570                 1575

Glu Glu Thr Glu Lys Arg His Arg Arg Leu Glu Glu Ala His Arg
1580             1585                 1590

Ala Gln Gln Tyr Tyr Phe Asp Ala Ala Glu Ala Glu Ala Trp Met
1595                1600                1605

Ser Glu Gln Glu Leu Tyr Met Met Ser Glu Glu Lys Ala Lys Asp
1610                1615                1620

Glu Gln Ser Ala Val Ser Met Leu Lys Lys His Gln Ile Leu Glu
1625                1630                1635

Gln Ala Val Glu Asp Tyr Ala Glu Thr Val His Gln Leu Ser Lys
1640                1645                1650

Thr Ser Arg Ala Leu Val Ala Asp Ser His Pro Glu Ser Glu Arg
1655                1660                1665

Ile Ser Met Arg Gln Ser Lys Val Asp Lys Leu Tyr Ala Gly Leu
1670                1675                1680

Lys Asp Leu Ala Glu Glu Arg Arg Gly Lys Leu Asp Glu Arg His
1685                1690                1695

Arg Leu Phe Gln Leu Asn Arg Glu Val Asp Asp Leu Glu Gln Trp
1700                1705                1710

Ile Ala Glu Arg Glu Val Val Ala Gly Ser His Glu Leu Gly Gln
1715                1720                1725

Asp Tyr Glu His Val Thr Met Leu Gln Glu Arg Phe Arg Glu Phe
1730                1735                1740

Ala Arg Asp Thr Gly Asn Ile Gly Gln Glu Arg Val Asp Thr Val
1745                1750                1755

Asn His Leu Ala Asp Glu Leu Ile Asn Ser Gly His Ser Asp Ala
1760                1765                1770

Ala Thr Ile Ala Glu Trp Lys Asp Gly Leu Asn Glu Ala Trp Ala
1775                1780                1785

Asp Leu Leu Glu Leu Ile Asp Thr Arg Thr Gln Ile Leu Ala Ala
1790                1795                1800

Ser Tyr Glu Leu His Lys Phe Tyr His Asp Ala Lys Glu Ile Phe
1805                1810                1815

Gly Arg Ile Gln Asp Lys His Lys Lys Leu Pro Glu Glu Leu Gly
1820                1825                1830

Arg Asp Gln Asn Thr Val Glu Thr Leu Gln Arg Met His Thr Thr
1835                1840                1845

Phe Glu His Asp Ile Gln Ala Leu Gly Thr Gln Arg Gln Leu Gln
1850                1855                1860

Glu Asp Ala Ala Arg Leu Gln Ala Ala Tyr Ala Gly Asp Lys Ala
1865                1870                1875

Asp Asp Ile Gln Lys Arg Glu Asn Glu Val Leu Glu Ala Trp Lys
1880                1885                1890

Ser Leu Leu Asp Ala Cys Glu Ser Arg Arg Val Arg Leu Val Asp
1895                1900                1905

Thr Gly Asp Lys Phe Arg Phe Phe Ser Met Val Arg Asp Leu Met
1910                1915                1920

Leu Trp Met Glu Asp Val Ile Arg Gln Ile Glu Ala Gln Glu Lys
1925                1930                1935

Pro Arg Asp Val Ser Ser Val Glu Leu Leu Met Asn Asn His Gln
1940                1945                1950

Gly Ile Lys Ala Glu Ile Asp Ala Arg Asn Asp Ser Phe Thr Thr
1955                1960                1965

Cys Ile Glu Leu Gly Lys Ser Leu Leu Ala Arg Lys His Tyr Ala
1970                1975                1980

Ser Glu Glu Ile Lys Glu Lys Leu Leu Gln Leu Thr Glu Lys Arg

```
                1985                1990                1995
Lys  Glu  Met  Ile  Asp  Lys  Trp  Glu  Asp  Arg  Trp  Glu  Trp  Leu  Arg
                2000                2005                2010

Leu  Ile  Leu  Glu  Val  His  Gln  Phe  Ser  Arg  Asp  Ala  Ser  Val  Ala
                2015                2020                2025

Glu  Ala  Trp  Leu  Leu  Gly  Gln  Glu  Pro  Tyr  Leu  Ser  Ser  Arg  Glu
                2030                2035                2040

Ile  Gly  Gln  Ser  Val  Asp  Val  Glu  Lys  Leu  Ile  Lys  Arg  His
                2045                2050                2055

Glu  Ala  Phe  Glu  Lys  Ser  Ala  Ala  Thr  Trp  Asp  Glu  Arg  Phe  Ser
                2060                2065                2070

Ala  Leu  Glu  Arg  Leu  Thr  Thr  Leu  Glu  Leu  Leu  Glu  Val  Arg  Arg
                2075                2080                2085

Gln  Gln  Glu  Glu  Glu  Glu  Arg  Lys  Arg  Arg  Pro  Pro  Ser  Pro  Glu
                2090                2095                2100

Pro  Ser  Thr  Lys  Val  Ser  Glu  Ala  Glu  Ser  Gln  Gln  Gln  Trp
                2105                2110                2115

Asp  Thr  Ser  Lys  Gly  Glu  Gln  Val  Ser  Gln  Asn  Gly  Leu  Pro  Ala
                2120                2125                2130

Glu  Gln  Gly  Ser  Pro  Arg  Val  Ser  Tyr  Arg  Ser  Gln  Thr  Tyr  Gln
                2135                2140                2145

Asn  Tyr  Lys  Asn  Phe  Asn  Ser  Arg  Arg  Thr  Ala  Ser  Asp  Gln  Pro
                2150                2155                2160

Trp  Ser  Gly  Leu
                2165

<210> SEQ ID NO 24
<211> LENGTH: 259
<212> TYPE: PRT
<213> ORGANISM: Homo sapiens

<400> SEQUENCE: 24

Met  Glu  Asp  Ser  Met  Asp  Met  Ser  Pro  Leu  Arg  Pro  Gln  Asn
 1                 5                  10                  15

Tyr  Leu  Phe  Gly  Cys  Glu  Leu  Lys  Ala  Asp  Lys  Asp  Tyr  His  Phe  Lys
                20                  25                  30

Val  Asp  Asn  Asp  Glu  Asn  Glu  His  Gln  Leu  Ser  Leu  Arg  Thr  Val  Ser
                35                  40                  45

Leu  Gly  Ala  Gly  Ala  Lys  Asp  Glu  Leu  His  Ile  Val  Glu  Ala  Glu  Ala
        50                  55                  60

Met  Asn  Tyr  Glu  Gly  Ser  Pro  Ile  Lys  Val  Thr  Leu  Ala  Thr  Leu  Lys
 65                 70                  75                  80

Met  Ser  Val  Gln  Pro  Thr  Val  Ser  Leu  Gly  Gly  Phe  Glu  Ile  Thr  Pro
                85                  90                  95

Pro  Val  Val  Leu  Arg  Leu  Lys  Cys  Gly  Ser  Gly  Pro  Val  His  Ile  Ser
                100                 105                 110

Gly  Gln  His  Leu  Val  Ala  Val  Glu  Glu  Asp  Ala  Glu  Ser  Glu  Asp  Glu
                115                 120                 125

Glu  Glu  Glu  Asp  Val  Lys  Leu  Leu  Ser  Ile  Ser  Gly  Lys  Arg  Ser  Ala
        130                 135                 140

Pro  Gly  Gly  Gly  Ser  Lys  Val  Pro  Gln  Lys  Lys  Val  Lys  Leu  Ala  Ala
145                 150                 155                 160

Asp  Glu  Asp  Asp  Asp  Asp  Asp  Glu  Glu  Asp  Asp  Asp  Glu  Asp  Asp
                165                 170                 175
```

-continued

```
Asp Asp Asp Asp Phe Asp Glu Glu Ala Glu Lys Ala Pro Val
            180             185             190

Lys Lys Ser Ile Arg Asp Thr Pro Ala Lys Asn Ala Gln Lys Ser Asn
        195                 200                 205

Gln Asn Gly Lys Asp Ser Lys Pro Ser Ser Thr Pro Arg Ser Lys Gly
        210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Ala His

<210> SEQ ID NO 25
<211> LENGTH: 1051
<212> TYPE: PRT
<213> ORGANISM: Homo sapiens

<400> SEQUENCE: 25

Met Gly Pro Gly Pro Ser Arg Ala Pro Arg Ala Pro Arg Leu Met Leu
1               5                   10                  15

Cys Ala Leu Ala Leu Met Val Ala Ala Gly Cys Val Val Ser Ala
            20                  25                  30

Phe Asn Leu Asp Thr Arg Phe Leu Val Val Lys Glu Ala Gly Asn Pro
        35                  40                  45

Gly Ser Leu Phe Gly Tyr Ser Val Ala Leu His Arg Gln Thr Glu Arg
    50                  55                  60

Gln Gln Arg Tyr Leu Leu Leu Ala Gly Ala Pro Arg Glu Leu Ala Val
65                  70                  75                  80

Pro Asp Gly Tyr Thr Asn Arg Thr Gly Ala Val Tyr Leu Cys Pro Leu
                85                  90                  95

Thr Ala His Lys Asp Asp Cys Glu Arg Met Asn Ile Thr Val Lys Asn
            100                 105                 110

Asp Pro Gly His His Ile Ile Glu Asp Met Trp Leu Gly Val Thr Val
        115                 120                 125

Ala Ser Gln Gly Pro Ala Gly Arg Val Leu Val Cys Ala His Arg Tyr
    130                 135                 140

Thr Gln Val Leu Trp Ser Gly Ser Glu Asp Gln Arg Arg Met Val Gly
145                 150                 155                 160

Lys Cys Tyr Val Arg Gly Asn Asp Leu Glu Leu Asp Ser Ser Asp Asp
                165                 170                 175

Trp Gln Thr Tyr His Asn Glu Met Cys Asn Ser Asn Thr Asp Tyr Leu
            180                 185                 190

Glu Thr Gly Met Cys Gln Leu Gly Thr Ser Gly Gly Phe Thr Gln Asn
        195                 200                 205

Thr Val Tyr Phe Gly Ala Pro Gly Ala Tyr Asn Trp Lys Gly Asn Ser
    210                 215                 220

Tyr Met Ile Gln Arg Lys Glu Trp Asp Leu Ser Glu Tyr Ser Tyr Lys
225                 230                 235                 240

Asp Pro Glu Asp Gln Gly Asn Leu Tyr Ile Gly Tyr Thr Met Gln Val
                245                 250                 255

Gly Ser Phe Ile Leu His Pro Lys Asn Ile Thr Ile Val Thr Gly Ala
            260                 265                 270

Pro Arg His Arg His Met Gly Ala Val Phe Leu Leu Ser Gln Glu Ala
        275                 280                 285
```

```
Gly Gly Asp Leu Arg Arg Arg Gln Val Leu Glu Gly Ser Gln Val Gly
    290                 295                 300
Ala Tyr Phe Gly Ser Ala Ile Ala Leu Ala Asp Leu Asn Asn Asp Gly
305                 310                 315                 320
Trp Gln Asp Leu Leu Val Gly Ala Pro Tyr Tyr Phe Glu Arg Lys Glu
                325                 330                 335
Glu Val Gly Gly Ala Ile Tyr Val Phe Met Asn Gln Ala Gly Thr Ser
            340                 345                 350
Phe Pro Ala His Pro Ser Leu Leu His Gly Pro Ser Gly Ser Ala
                355                 360                 365
Phe Gly Leu Ser Val Ala Ser Ile Gly Asp Ile Asn Gln Asp Gly Phe
370                 375                 380
Gln Asp Ile Ala Val Gly Ala Pro Phe Glu Gly Leu Gly Lys Val Tyr
385                 390                 395                 400
Ile Tyr His Ser Ser Lys Gly Leu Leu Arg Gln Pro Gln Gln Val
                405                 410                 415
Ile His Gly Glu Lys Leu Gly Leu Pro Gly Leu Ala Thr Phe Gly Tyr
            420                 425                 430
Ser Leu Ser Gly Gln Met Asp Val Asp Glu Asn Phe Tyr Pro Asp Leu
        435                 440                 445
Leu Val Gly Ser Leu Ser Asp His Ile Val Leu Arg Ala Arg Pro
450                 455                 460
Val Ile Asn Ile Val His Lys Thr Leu Val Pro Arg Pro Ala Val Leu
465                 470                 475                 480
Asp Pro Ala Leu Cys Thr Ala Thr Ser Cys Val Gln Val Glu Leu Cys
                485                 490                 495
Phe Ala Tyr Asn Gln Ser Ala Gly Asn Pro Asn Tyr Arg Arg Asn Ile
            500                 505                 510
Thr Leu Ala Tyr Thr Leu Glu Ala Asp Arg Asp Arg Pro Pro Arg
        515                 520                 525
Leu Arg Phe Ala Gly Ser Glu Ser Ala Val Phe His Gly Phe Phe Ser
530                 535                 540
Met Pro Glu Met Arg Cys Gln Lys Leu Glu Leu Leu Met Asp Asn
545                 550                 555                 560
Leu Arg Asp Lys Leu Arg Pro Ile Ile Ser Met Asn Tyr Ser Leu
                565                 570                 575
Pro Leu Arg Met Pro Asp Arg Pro Arg Leu Gly Leu Arg Ser Leu Asp
            580                 585                 590
Ala Tyr Pro Ile Leu Asn Gln Ala Gln Ala Leu Glu Asn His Thr Glu
        595                 600                 605
Val Gln Phe Gln Lys Glu Cys Gly Pro Asp Asn Lys Cys Glu Ser Asn
610                 615                 620
Leu Gln Met Arg Ala Ala Phe Val Ser Glu Gln Gln Lys Leu Ser
625                 630                 635                 640
Arg Leu Gln Tyr Ser Arg Asp Val Arg Lys Leu Leu Leu Ser Ile Asn
                645                 650                 655
Val Thr Asn Thr Arg Thr Ser Glu Arg Ser Gly Glu Asp Ala His Glu
            660                 665                 670
Ala Leu Leu Thr Leu Val Val Pro Ala Leu Leu Leu Ser Ser Val
        675                 680                 685
Arg Pro Pro Gly Ala Cys Gln Ala Asn Glu Thr Ile Phe Cys Glu Leu
690                 695                 700
Gly Asn Pro Phe Lys Arg Asn Gln Arg Met Glu Leu Leu Ile Ala Phe
```

```
                705                 710                 715                 720
        Glu Val Ile Gly Val Thr Leu His Thr Arg Asp Leu Gln Val Gln Leu
                        725                 730                 735

Gln Leu Ser Thr Ser Ser His Gln Asp Asn Leu Trp Pro Met Ile Leu
                        740                 745                 750

Thr Leu Leu Val Asp Tyr Thr Leu Gln Thr Ser Leu Ser Met Val Asn
                        755                 760                 765

His Arg Leu Gln Ser Phe Phe Gly Gly Thr Val Met Gly Glu Ser Gly
                        770                 775                 780

Met Lys Thr Val Glu Asp Val Gly Ser Pro Leu Lys Tyr Glu Phe Gln
        785                 790                 795                 800

Val Gly Pro Met Gly Glu Gly Leu Val Gly Leu Gly Thr Leu Val Leu
                        805                 810                 815

Gly Leu Glu Trp Pro Tyr Glu Val Ser Asn Gly Lys Trp Leu Leu Tyr
                        820                 825                 830

Pro Thr Glu Ile Thr Val His Gly Asn Gly Ser Trp Pro Cys Arg Pro
                        835                 840                 845

Pro Gly Asp Leu Ile Asn Pro Leu Asn Leu Thr Leu Ser Asp Pro Gly
                        850                 855                 860

Asp Arg Pro Ser Ser Pro Gln Arg Arg Arg Arg Gln Leu Asp Pro Gly
        865                 870                 875                 880

Gly Gly Gln Gly Pro Pro Val Thr Leu Ala Ala Ala Lys Lys Ala
                        885                 890                 895

Lys Ser Glu Thr Val Leu Thr Cys Ala Thr Gly Arg Ala His Cys Val
                        900                 905                 910

Trp Leu Glu Cys Pro Ile Pro Asp Ala Pro Val Val Thr Asn Val Thr
                        915                 920                 925

Val Lys Ala Arg Val Trp Asn Ser Thr Phe Ile Glu Asp Tyr Arg Asp
                        930                 935                 940

Phe Asp Arg Val Arg Val Asn Gly Trp Ala Thr Leu Phe Leu Arg Thr
        945                 950                 955                 960

Ser Ile Pro Thr Ile Asn Met Glu Asn Lys Thr Thr Trp Phe Ser Val
                        965                 970                 975

Asp Ile Asp Ser Glu Leu Val Glu Glu Leu Pro Ala Glu Ile Glu Leu
                        980                 985                 990

Trp Leu Val Leu Val Ala Val Gly Ala Gly Leu Leu Leu Leu Gly Leu
                        995                 1000                1005

Ile Ile Leu Leu Leu Trp Lys Cys Gly Phe Phe Lys Arg Ala Arg
                        1010                1015                1020

Thr Arg Ala Leu Tyr Glu Ala Lys Arg Gln Lys Ala Glu Met Lys
                        1025                1030                1035

Ser Gln Pro Ser Glu Thr Glu Arg Leu Thr Asp Asp Tyr
                        1040                1045                1050

<210> SEQ ID NO 26
<211> LENGTH: 375
<212> TYPE: PRT
<213> ORGANISM: homo sapiens

<400> SEQUENCE: 26

Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30
```

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
 50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
             85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
            115                 120                 125

Thr Pro Ala Met Tyr Val Ala Ile Gln Ala Val Leu Ser Leu Tyr Ala
            130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
            195                 200                 205

Val Arg Asp Ile Lys Glu Lys Leu Cys Tyr Val Ala Leu Asp Phe Glu
            210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
            245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
            275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
            355                 360                 365

Ile Val His Arg Lys Cys Phe
            370                 375

<210> SEQ ID NO 27
<211> LENGTH: 967
<212> TYPE: PRT
<213> ORGANISM: homo sapiens

<400> SEQUENCE: 27

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

-continued

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
            115                 120                 125

Tyr Thr Leu Ser Gln Gly His Arg Val Val Leu Arg Gly Val Gly Gly
            130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
            195                 200                 205

Thr Thr Gln Met Gln Ala Ala Asp Ala Arg Lys Ser Phe Pro Cys Phe
            210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
            275                 280                 285

Tyr Val Glu Lys Gln Ala Ser Asn Gly Val Leu Ile Arg Ile Trp Ala
            290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
            355                 360                 365

Phe Asp Pro Leu Ser Ser Ser Ser Asn Lys Glu Arg Val Val Thr
370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
            435                 440                 445

```
Leu Ala Ser Ser His Pro Leu Ser Thr Pro Ala Ser Glu Ile Asn Thr
450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
            485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
                580                 585                 590

Asp Gly Arg Gln Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
        610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
850                 855                 860

Ser Ile Thr Asn Asn Val Ile Gly Gln Gly Leu Val Trp Asp Phe Val
```

```
                865                 870                 875                 880
Gln Ser Asn Trp Lys Lys Leu Phe Asn Asp Tyr Gly Gly Gly Ser Phe
                    885                 890                 895

Ser Phe Ser Asn Leu Ile Gln Ala Val Thr Arg Arg Phe Ser Thr Glu
                900                 905                 910

Tyr Glu Leu Gln Gln Leu Glu Gln Phe Lys Lys Asp Asn Glu Glu Thr
                915                 920                 925

Gly Phe Gly Ser Gly Thr Arg Ala Leu Glu Gln Ala Leu Glu Lys Thr
            930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 28
<211> LENGTH: 181
<212> TYPE: PRT
<213> ORGANISM: homo sapiens

<400> SEQUENCE: 28

Met Gly Gly Phe Phe Ser Ser Ile Phe Ser Ser Leu Phe Gly Thr Arg
1               5                   10                  15

Glu Met Arg Ile Leu Ile Leu Gly Leu Asp Gly Ala Gly Lys Thr Thr
                20                  25                  30

Ile Leu Tyr Arg Leu Gln Val Gly Glu Val Val Thr Thr Ile Pro Thr
            35                  40                  45

Ile Gly Phe Asn Val Glu Thr Val Thr Tyr Lys Asn Leu Lys Phe Gln
        50                  55                  60

Val Trp Asp Leu Gly Gly Gln Thr Ser Ile Arg Pro Tyr Trp Arg Cys
65                  70                  75                  80

Tyr Tyr Ser Asn Thr Asp Ala Val Ile Tyr Val Val Asp Ser Cys Asp
                85                  90                  95

Arg Asp Arg Ile Gly Ile Ser Lys Ser Glu Leu Val Ala Met Leu Glu
                100                 105                 110

Glu Glu Glu Leu Arg Lys Ala Ile Leu Val Val Phe Ala Asn Lys Gln
            115                 120                 125

Asp Met Glu Gln Ala Met Thr Ser Ser Glu Met Ala Asn Ser Leu Gly
        130                 135                 140

Leu Pro Ala Leu Lys Asp Arg Lys Trp Gln Ile Phe Lys Thr Ser Ala
145                 150                 155                 160

Thr Lys Gly Thr Gly Leu Asp Glu Ala Met Glu Trp Leu Val Glu Thr
                165                 170                 175

Leu Lys Ser Arg Gln
            180

<210> SEQ ID NO 29
<211> LENGTH: 511
<212> TYPE: PRT
<213> ORGANISM: homo sapiens

<400> SEQUENCE: 29

Met Ala Leu Arg Ala Met Arg Gly Ile Val Asn Gly Ala Ala Pro Glu
1               5                   10                  15

Leu Pro Val Pro Thr Gly Gly Pro Ala Val Gly Ala Arg Glu Gln Ala
                20                  25                  30

Leu Ala Val Ser Arg Asn Tyr Leu Ser Gln Pro Arg Leu Thr Tyr Lys
```

```
                35                  40                  45
Thr Val Ser Gly Val Asn Gly Pro Leu Val Ile Leu Asp His Val Lys
 50                  55                  60

Phe Pro Arg Tyr Ala Glu Ile Val His Leu Thr Leu Pro Asp Gly Thr
 65                  70                  75                  80

Lys Arg Ser Gly Gln Val Leu Glu Val Ser Gly Ser Lys Ala Val Val
                 85                  90                  95

Gln Val Phe Glu Gly Thr Ser Gly Ile Asp Ala Lys Lys Thr Ser Cys
                100                 105                 110

Glu Phe Thr Gly Asp Ile Leu Arg Thr Pro Val Ser Glu Asp Met Leu
                115                 120                 125

Gly Arg Val Phe Asn Gly Ser Gly Lys Pro Ile Asp Arg Gly Pro Val
                130                 135                 140

Val Leu Ala Glu Asp Phe Leu Asp Ile Met Gly Gln Pro Ile Asn Pro
145                 150                 155                 160

Gln Cys Arg Ile Tyr Pro Glu Glu Met Ile Gln Thr Gly Ile Ser Ala
                165                 170                 175

Ile Asp Gly Met Asn Ser Ile Ala Arg Gly Gln Lys Ile Pro Ile Phe
                180                 185                 190

Ser Ala Ala Gly Leu Pro His Asn Glu Ile Ala Ala Gln Ile Cys Arg
                195                 200                 205

Gln Ala Gly Leu Val Lys Lys Ser Lys Asp Val Val Asp Tyr Ser Glu
                210                 215                 220

Glu Asn Phe Ala Ile Val Phe Ala Ala Met Gly Val Asn Met Glu Thr
225                 230                 235                 240

Ala Arg Phe Phe Lys Ser Asp Phe Glu Glu Asn Gly Ser Met Asp Asn
                245                 250                 255

Val Cys Leu Phe Leu Asn Leu Ala Asn Asp Pro Thr Ile Glu Arg Ile
                260                 265                 270

Ile Thr Pro Arg Leu Ala Leu Thr Thr Ala Glu Phe Leu Ala Tyr Gln
                275                 280                 285

Cys Glu Lys His Val Leu Val Ile Leu Thr Asp Met Ser Ser Tyr Ala
                290                 295                 300

Glu Ala Leu Arg Glu Val Ser Ala Ala Arg Glu Glu Val Pro Gly Arg
305                 310                 315                 320

Arg Gly Phe Pro Gly Tyr Met Tyr Thr Asp Leu Ala Thr Ile Tyr Glu
                325                 330                 335

Arg Ala Gly Arg Val Glu Gly Arg Asn Gly Ser Ile Thr Gln Ile Pro
                340                 345                 350

Ile Leu Thr Met Pro Asn Asp Asp Ile Thr His Pro Ile Pro Asp Leu
                355                 360                 365

Thr Gly Tyr Ile Thr Glu Gly Gln Ile Tyr Val Asp Arg Gln Leu His
                370                 375                 380

Asn Arg Gln Ile Tyr Pro Pro Ile Asn Val Leu Pro Ser Leu Ser Arg
385                 390                 395                 400

Leu Met Lys Ser Ala Ile Gly Glu Gly Met Thr Arg Lys Asp His Ala
                405                 410                 415

Asp Val Ser Asn Gln Leu Tyr Ala Cys Tyr Ala Ile Gly Lys Asp Val
                420                 425                 430

Gln Ala Met Lys Ala Val Val Gly Glu Glu Ala Leu Thr Ser Asp Asp
                435                 440                 445

Leu Leu Tyr Leu Glu Phe Leu Gln Lys Phe Glu Arg Asn Phe Ile Ala
450                 455                 460
```

```
Gln Gly Pro Tyr Glu Asn Arg Thr Val Phe Glu Thr Leu Asp Ile Gly
465                 470                 475                 480

Trp Gln Leu Leu Arg Ile Phe Pro Lys Glu Met Leu Lys Arg Ile Pro
                485                 490                 495

Gln Ser Thr Leu Ser Glu Phe Tyr Pro Arg Asp Ser Ala Lys His
                500                 505                 510

<210> SEQ ID NO 30
<211> LENGTH: 1675
<212> TYPE: PRT
<213> ORGANISM: homo sapiens

<400> SEQUENCE: 30

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
                20                  25                  30

Glu Ser Asp Lys Phe Ile Cys Ile Arg Glu Lys Val Gly Glu Gln Ala
            35                  40                  45

Gln Val Val Ile Ile Asp Met Asn Asp Pro Ser Asn Pro Ile Arg Arg
50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
```

-continued

```
                325                 330                 335
Tyr Ile Thr Asn Val Leu Gln Asn Pro Asp Leu Ala Leu Arg Met Ala
            340                 345                 350
Val Arg Asn Asn Leu Ala Gly Ala Glu Glu Leu Phe Ala Arg Lys Phe
            355                 360                 365
Asn Ala Leu Phe Ala Gln Gly Asn Tyr Ser Glu Ala Ala Lys Val Ala
            370                 375                 380
Ala Asn Ala Pro Lys Gly Ile Leu Arg Thr Pro Asp Thr Ile Arg Arg
385                 390                 395                 400
Phe Gln Ser Val Pro Ala Gln Pro Gly Gln Thr Ser Pro Leu Leu Gln
                405                 410                 415
Tyr Phe Gly Ile Leu Leu Asp Gln Gly Gln Leu Asn Lys Tyr Glu Ser
                420                 425                 430
Leu Glu Leu Cys Arg Pro Val Leu Gln Gln Gly Arg Lys Gln Leu Leu
                435                 440                 445
Glu Lys Trp Leu Lys Glu Asp Lys Leu Glu Cys Ser Glu Glu Leu Gly
                450                 455                 460
Asp Leu Val Lys Ser Val Asp Pro Thr Leu Ala Leu Ser Val Tyr Leu
465                 470                 475                 480
Arg Ala Asn Val Pro Asn Lys Val Ile Gln Cys Phe Ala Glu Thr Gly
                485                 490                 495
Gln Val Gln Lys Ile Val Leu Tyr Ala Lys Lys Val Gly Tyr Thr Pro
                500                 505                 510
Asp Trp Ile Phe Leu Leu Arg Asn Val Met Arg Ile Ser Pro Asp Gln
                515                 520                 525
Gly Gln Gln Phe Ala Gln Met Leu Val Gln Asp Glu Glu Pro Leu Ala
                530                 535                 540
Asp Ile Thr Gln Ile Val Asp Val Phe Met Glu Tyr Asn Leu Ile Gln
545                 550                 555                 560
Gln Cys Thr Ala Phe Leu Leu Asp Ala Leu Lys Asn Asn Arg Pro Ser
                565                 570                 575
Glu Gly Pro Leu Gln Thr Arg Leu Leu Glu Met Asn Leu Met His Ala
                580                 585                 590
Pro Gln Val Ala Asp Ala Ile Leu Gly Asn Gln Met Phe Thr His Tyr
                595                 600                 605
Asp Arg Ala His Ile Ala Gln Leu Cys Glu Lys Ala Gly Leu Leu Gln
                610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
                645                 650                 655
Ser Leu Ser Val Glu Asp Ser Leu Glu Cys Leu Arg Ala Met Leu Ser
                660                 665                 670
Ala Asn Ile Arg Gln Asn Leu Gln Ile Cys Val Gln Val Ala Ser Lys
                675                 680                 685
Tyr His Glu Gln Leu Ser Thr Gln Ser Leu Ile Glu Leu Phe Glu Ser
                690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
                725                 730                 735
Lys Thr Gly Gln Ile Lys Glu Val Glu Arg Ile Cys Arg Glu Ser Asn
                740                 745                 750
```

-continued

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
                820                 825                 830

Ile Leu Val Val Arg Gly Gln Phe Ser Thr Asp Glu Leu Val Ala Glu
                835                 840                 845

Val Glu Lys Arg Asn Arg Leu Lys Leu Leu Pro Trp Leu Glu Ala
850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Pro Glu Arg Phe Leu Arg Glu
                885                 890                 895

Asn Pro Tyr Tyr Asp Ser Arg Val Val Gly Lys Tyr Cys Glu Lys Arg
                900                 905                 910

Asp Pro His Leu Ala Cys Val Ala Tyr Glu Arg Gly Gln Cys Asp Leu
                915                 920                 925

Glu Leu Ile Asn Val Cys Asn Glu Asn Ser Leu Phe Lys Ser Leu Ser
        930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
                980                 985                 990

Lys Ala Phe Met Thr Ala Asp Leu Pro Asn Glu Leu Ile Glu Leu Leu
        995                 1000                1005

Glu Lys Ile Val Leu Asp Asn Ser Val Phe Ser Glu His Arg Asn
        1010                1015                1020

Leu Gln Asn Leu Leu Ile Leu Thr Ala Ile Lys Ala Asp Arg Thr
        1025                1030                1035

Arg Val Met Glu Tyr Ile Asn Arg Leu Asp Asn Tyr Asp Ala Pro
        1040                1045                1050

Asp Ile Ala Asn Ile Ala Ile Ser Asn Glu Leu Phe Glu Glu Ala
        1055                1060                1065

Phe Ala Ile Phe Arg Lys Phe Asp Val Asn Thr Ser Ala Val Gln
        1070                1075                1080

Val Leu Ile Glu His Ile Gly Asn Leu Asp Arg Ala Tyr Glu Phe
        1085                1090                1095

Ala Glu Arg Cys Asn Glu Pro Ala Val Trp Ser Gln Leu Ala Lys
        1100                1105                1110

Ala Gln Leu Gln Lys Gly Met Val Lys Glu Ala Ile Asp Ser Tyr
        1115                1120                1125

Ile Lys Ala Asp Asp Pro Ser Ser Tyr Met Glu Val Val Gln Ala
        1130                1135                1140

Ala Asn Thr Ser Gly Asn Trp Glu Glu Leu Val Lys Tyr Leu Gln
        1145                1150                1155

```
Met Ala Arg Lys Lys Ala Arg Glu Ser Tyr Val Glu Thr Glu Leu
    1160            1165                1170
Ile Phe Ala Leu Ala Lys Thr Asn Arg Leu Ala Glu Leu Glu Glu
    1175            1180                1185
Phe Ile Asn Gly Pro Asn Asn Ala His Ile Gln Gln Val Gly Asp
    1190            1195                1200
Arg Cys Tyr Asp Glu Lys Met Tyr Asp Ala Ala Lys Leu Leu Tyr
    1205            1210                1215
Asn Asn Val Ser Asn Phe Gly Arg Leu Ala Ser Thr Leu Val His
    1220            1225                1230
Leu Gly Glu Tyr Gln Ala Ala Val Asp Gly Ala Arg Lys Ala Asn
    1235            1240                1245
Ser Thr Arg Thr Trp Lys Glu Val Cys Phe Ala Cys Val Asp Gly
    1250            1255                1260
Lys Glu Phe Arg Leu Ala Gln Met Cys Gly Leu His Ile Val Val
    1265            1270                1275
His Ala Asp Glu Leu Glu Glu Leu Ile Asn Tyr Tyr Gln Asp Arg
    1280            1285                1290
Gly Tyr Phe Glu Glu Leu Ile Thr Met Leu Glu Ala Ala Leu Gly
    1295            1300                1305
Leu Glu Arg Ala His Met Gly Met Phe Thr Glu Leu Ala Ile Leu
    1310            1315                1320
Tyr Ser Lys Phe Lys Pro Gln Lys Met Arg Glu His Leu Glu Leu
    1325            1330                1335
Phe Trp Ser Arg Val Asn Ile Pro Lys Val Leu Arg Ala Ala Glu
    1340            1345                1350
Gln Ala His Leu Trp Ala Glu Leu Val Phe Leu Tyr Asp Lys Tyr
    1355            1360                1365
Glu Glu Tyr Asp Asn Ala Ile Ile Thr Met Met Asn His Pro Thr
    1370            1375                1380
Asp Ala Trp Lys Glu Gly Gln Phe Lys Asp Ile Ile Thr Lys Val
    1385            1390                1395
Ala Asn Val Glu Leu Tyr Tyr Arg Ala Ile Gln Phe Tyr Leu Glu
    1400            1405                1410
Phe Lys Pro Leu Leu Leu Asn Asp Leu Leu Met Val Leu Ser Pro
    1415            1420                1425
Arg Leu Asp His Thr Arg Ala Val Asn Tyr Phe Ser Lys Val Lys
    1430            1435                1440
Gln Leu Pro Leu Val Lys Pro Tyr Leu Arg Ser Val Gln Asn His
    1445            1450                1455
Asn Asn Lys Ser Val Asn Glu Ser Leu Asn Asn Leu Phe Ile Thr
    1460            1465                1470
Glu Glu Asp Tyr Gln Ala Leu Arg Thr Ser Ile Asp Ala Tyr Asp
    1475            1480                1485
Asn Phe Asp Asn Ile Ser Leu Ala Gln Arg Leu Glu Lys His Glu
    1490            1495                1500
Leu Ile Glu Phe Arg Arg Ile Ala Ala Tyr Leu Phe Lys Gly Asn
    1505            1510                1515
Asn Arg Trp Lys Gln Ser Val Glu Leu Cys Lys Lys Asp Ser Leu
    1520            1525                1530
Tyr Lys Asp Ala Met Gln Tyr Ala Ser Glu Ser Lys Asp Thr Glu
    1535            1540                1545
Leu Ala Glu Glu Leu Leu Gln Trp Phe Leu Gln Glu Glu Lys Arg
```

```
                    1550                1555                1560

Glu Cys Phe Gly Ala Cys Leu Phe Thr Cys Tyr Asp Leu Leu Arg
        1565                1570                1575

Pro Asp Val Val Leu Glu Thr Ala Trp Arg His Asn Ile Met Asp
        1580                1585                1590

Phe Ala Met Pro Tyr Phe Ile Gln Val Met Lys Glu Tyr Leu Thr
        1595                1600                1605

Lys Val Asp Lys Leu Asp Ala Ser Glu Ser Leu Arg Lys Glu Glu
        1610                1615                1620

Glu Gln Ala Thr Glu Thr Gln Pro Ile Val Tyr Gly Gln Pro Gln
        1625                1630                1635

Leu Met Leu Thr Ala Gly Pro Ser Val Ala Val Pro Pro Gln Ala
        1640                1645                1650

Pro Phe Gly Tyr Gly Tyr Thr Ala Pro Pro Tyr Gly Gln Pro Gln
        1655                1660                1665

Pro Gly Phe Gly Tyr Ser Met
        1670                1675

<210> SEQ ID NO 31
<211> LENGTH: 315
<212> TYPE: PRT
<213> ORGANISM: homo sapiens

<400> SEQUENCE: 31

Met Pro Gly Leu Ser Cys Arg Phe Tyr Gln His Lys Phe Pro Glu Val
1               5                   10                  15

Glu Asp Val Val Met Val Asn Val Arg Ser Ile Ala Glu Met Gly Ala
            20                  25                  30

Tyr Val Ser Leu Leu Glu Tyr Asn Asn Ile Glu Gly Met Ile Leu Leu
        35                  40                  45

Ser Glu Leu Ser Arg Arg Arg Ile Arg Ser Ile Asn Lys Leu Ile Arg
    50                  55                  60

Ile Gly Arg Asn Glu Cys Val Val Val Ile Arg Val Asp Lys Glu Lys
65                  70                  75                  80

Gly Tyr Ile Asp Leu Ser Lys Arg Arg Val Ser Pro Glu Glu Ala Ile
                85                  90                  95

Lys Cys Glu Asp Lys Phe Thr Lys Ser Lys Thr Val Tyr Ser Ile Leu
            100                 105                 110

Arg His Val Ala Glu Val Leu Glu Tyr Thr Lys Asp Glu Gln Leu Glu
        115                 120                 125

Ser Leu Phe Gln Arg Thr Ala Trp Val Phe Asp Asp Lys Tyr Lys Arg
    130                 135                 140

Pro Gly Tyr Gly Ala Tyr Asp Ala Phe Lys His Ala Val Ser Asp Pro
145                 150                 155                 160

Ser Ile Leu Asp Ser Leu Asp Leu Asn Glu Asp Glu Arg Glu Val Leu
                165                 170                 175

Ile Asn Asn Ile Asn Arg Arg Leu Thr Pro Gln Ala Val Lys Ile Arg
            180                 185                 190

Ala Asp Ile Glu Val Ala Cys Tyr Gly Tyr Glu Gly Ile Asp Ala Val
        195                 200                 205

Lys Glu Ala Leu Arg Ala Gly Leu Asn Cys Ser Thr Glu Asn Met Pro
    210                 215                 220

Ile Lys Ile Asn Leu Ile Ala Pro Pro Arg Tyr Val Met Thr Thr Thr
225                 230                 235                 240
```

```
Thr Leu Glu Arg Thr Glu Gly Leu Ser Val Leu Ser Gln Ala Met Ala
                245                 250                 255

Val Ile Lys Glu Lys Ile Glu Glu Lys Arg Gly Val Phe Asn Val Gln
            260                 265                 270

Met Glu Pro Lys Val Val Thr Asp Thr Asp Glu Thr Glu Leu Ala Arg
        275                 280                 285

Gln Met Glu Arg Leu Glu Arg Glu Asn Ala Glu Val Asp Gly Asp Asp
    290                 295                 300

Asp Ala Glu Glu Met Glu Ala Lys Ala Glu Asp
305                 310                 315

<210> SEQ ID NO 32
<211> LENGTH: 681
<212> TYPE: PRT
<213> ORGANISM: homo sapiens

<400> SEQUENCE: 32

Met Cys Gly Ile Phe Ala Tyr Leu Asn Tyr His Val Pro Arg Thr Arg
1               5                   10                  15

Arg Glu Ile Leu Glu Thr Leu Ile Lys Gly Leu Gln Arg Leu Glu Tyr
            20                  25                  30

Arg Gly Tyr Asp Ser Ala Gly Val Gly Phe Asp Gly Gly Asn Asp Lys
        35                  40                  45

Asp Trp Glu Ala Asn Ala Cys Lys Ile Gln Leu Ile Lys Lys Lys Gly
    50                  55                  60

Lys Val Lys Ala Leu Asp Glu Glu Val His Lys Gln Gln Asp Met Asp
65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser
            100                 105                 110

Asp Lys Asn Asn Glu Phe Ile Val Ile His Asn Gly Ile Ile Thr Asn
        115                 120                 125

Tyr Lys Asp Leu Lys Lys Phe Leu Glu Ser Lys Gly Tyr Asp Phe Glu
    130                 135                 140

Ser Glu Thr Asp Thr Glu Thr Ile Ala Lys Leu Val Lys Tyr Met Tyr
145                 150                 155                 160

Asp Asn Arg Glu Ser Gln Asp Thr Ser Phe Thr Thr Leu Val Glu Arg
                165                 170                 175

Val Ile Gln Gln Leu Glu Gly Ala Phe Ala Leu Val Phe Lys Ser Val
            180                 185                 190

His Phe Pro Gly Gln Ala Val Gly Thr Arg Arg Gly Ser Pro Leu Leu
        195                 200                 205

Ile Gly Val Arg Ser Glu His Lys Leu Ser Thr Asp His Ile Pro Ile
    210                 215                 220

Leu Tyr Arg Thr Gly Lys Asp Lys Lys Gly Ser Cys Asn Leu Ser Arg
225                 230                 235                 240

Val Asp Ser Thr Thr Cys Leu Phe Pro Val Glu Glu Lys Ala Val Glu
                245                 250                 255

Tyr Tyr Phe Ala Ser Asp Ala Ser Ala Val Ile Glu His Thr Asn Arg
            260                 265                 270

Val Ile Phe Leu Glu Asp Asp Val Ala Ala Val Val Asp Gly Arg
        275                 280                 285

Leu Ser Ile His Arg Ile Lys Arg Thr Ala Gly Asp His Pro Gly Arg
    290                 295                 300
```

-continued

```
Ala Val Gln Thr Leu Gln Met Glu Leu Gln Gln Ile Met Lys Gly Asn
305                 310                 315                 320

Phe Ser Ser Phe Met Gln Lys Glu Ile Phe Glu Gln Pro Glu Ser Val
            325                 330                 335

Val Asn Thr Met Arg Gly Arg Val Asn Phe Asp Asp Tyr Thr Val Asn
            340                 345                 350

Leu Gly Gly Leu Lys Asp His Ile Lys Glu Ile Gln Arg Cys Arg Arg
        355                 360                 365

Leu Ile Leu Ile Ala Cys Gly Thr Ser Tyr His Ala Gly Val Ala Thr
370                 375                 380

Arg Gln Val Leu Glu Glu Leu Thr Glu Leu Pro Val Met Val Glu Leu
385                 390                 395                 400

Ala Ser Asp Phe Leu Asp Arg Asn Thr Pro Val Phe Arg Asp Asp Val
                405                 410                 415

Cys Phe Phe Leu Ser Gln Ser Gly Glu Thr Ala Asp Thr Leu Met Gly
            420                 425                 430

Leu Arg Tyr Cys Lys Glu Arg Gly Ala Leu Thr Val Gly Ile Thr Asn
        435                 440                 445

Thr Val Gly Ser Ser Ile Ser Arg Glu Thr Asp Cys Gly Val His Ile
450                 455                 460

Asn Ala Gly Pro Glu Ile Gly Val Ala Ser Thr Lys Ala Tyr Thr Ser
465                 470                 475                 480

Gln Phe Val Ser Leu Val Met Phe Ala Leu Met Met Cys Asp Asp Arg
                485                 490                 495

Ile Ser Met Gln Glu Arg Arg Lys Glu Ile Met Leu Gly Leu Lys Arg
            500                 505                 510

Leu Pro Asp Leu Ile Lys Glu Val Leu Ser Met Asp Asp Glu Ile Gln
        515                 520                 525

Lys Leu Ala Thr Glu Leu Tyr His Gln Lys Ser Val Leu Ile Met Gly
530                 535                 540

Arg Gly Tyr His Tyr Ala Thr Cys Leu Glu Gly Ala Leu Lys Ile Lys
545                 550                 555                 560

Glu Ile Thr Tyr Met His Ser Glu Gly Ile Leu Ala Gly Glu Leu Lys
                565                 570                 575

His Gly Pro Leu Ala Leu Val Asp Lys Leu Met Pro Val Ile Met Ile
            580                 585                 590

Ile Met Arg Asp His Thr Tyr Ala Lys Cys Gln Asn Ala Leu Gln Gln
        595                 600                 605

Val Val Ala Arg Gln Gly Arg Pro Val Val Ile Cys Asp Lys Glu Asp
610                 615                 620

Thr Glu Thr Ile Lys Asn Thr Lys Arg Thr Ile Lys Val Pro His Ser
625                 630                 635                 640

Val Asp Cys Leu Gln Gly Ile Leu Ser Val Ile Pro Leu Gln Leu Leu
                645                 650                 655

Ala Phe His Leu Ala Val Leu Arg Gly Tyr Asp Val Asp Phe Pro Arg
            660                 665                 670

Asn Leu Ala Lys Ser Val Thr Val Glu
        675                 680

<210> SEQ ID NO 33
<211> LENGTH: 590
<212> TYPE: PRT
<213> ORGANISM: homo sapiens
```

<400> SEQUENCE: 33

Met Ser Arg Gln Ser Ser Val Ser Phe Arg Ser Gly Gly Ser Arg Ser
1               5                   10                  15

Phe Ser Thr Ala Ser Ala Ile Thr Pro Ser Val Ser Arg Thr Ser Phe
            20                  25                  30

Thr Ser Val Ser Arg Ser Gly Gly Gly Gly Gly Phe Gly Arg
        35                  40                  45

Val Ser Leu Ala Gly Ala Cys Gly Val Gly Gly Tyr Gly Ser Arg Ser
    50                  55                  60

Leu Tyr Asn Leu Gly Gly Ser Lys Arg Ile Ser Ile Ser Thr Ser Gly
65              70                  75                  80

Gly Ser Phe Arg Asn Arg Phe Gly Ala Gly Ala Gly Gly Tyr Gly
                85                  90                  95

Phe Gly Gly Gly Ala Gly Ser Gly Phe Gly Phe Gly Gly Ala Gly
                100                 105                 110

Gly Gly Phe Gly Leu Gly Gly Ala Gly Phe Gly Gly Phe Gly
            115                 120                 125

Gly Pro Gly Phe Pro Val Cys Pro Pro Gly Gly Ile Gln Glu Val Thr
    130                 135                 140

Val Asn Gln Ser Leu Leu Thr Pro Leu Asn Leu Gln Ile Asp Pro Ser
145                 150                 155                 160

Ile Gln Arg Val Arg Thr Glu Arg Glu Gln Ile Lys Thr Leu Asn
                165                 170                 175

Asn Lys Phe Ala Ser Phe Ile Asp Lys Val Arg Phe Leu Glu Gln Gln
                180                 185                 190

Asn Lys Val Leu Asp Thr Lys Trp Thr Leu Leu Gln Glu Gln Gly Thr
            195                 200                 205

Lys Thr Val Arg Gln Asn Leu Glu Pro Leu Phe Glu Gln Tyr Ile Asn
    210                 215                 220

Asn Leu Arg Arg Gln Leu Asp Ser Ile Val Gly Glu Arg Gly Arg Leu
225                 230                 235                 240

Asp Ser Glu Leu Arg Asn Met Gln Asp Leu Val Glu Asp Phe Lys Asn
                245                 250                 255

Lys Tyr Glu Asp Glu Ile Asn Lys Arg Thr Thr Ala Glu Asn Glu Phe
                260                 265                 270

Val Met Leu Lys Lys Asp Val Asp Ala Ala Tyr Met Asn Lys Val Glu
            275                 280                 285

Leu Glu Ala Lys Val Asp Ala Leu Met Asp Glu Ile Asn Phe Met Lys
    290                 295                 300

Met Phe Phe Asp Ala Glu Leu Ser Gln Met Gln Thr His Val Ser Asp
305                 310                 315                 320

Thr Ser Val Val Leu Ser Met Asp Asn Asn Arg Asn Leu Asp Leu Asp
                325                 330                 335

Ser Ile Ile Ala Glu Val Lys Ala Gln Tyr Glu Glu Ile Ala Asn Arg
            340                 345                 350

Ser Arg Thr Glu Ala Glu Ser Trp Tyr Gln Thr Lys Tyr Glu Glu Leu
    355                 360                 365

Gln Gln Thr Ala Gly Arg His Gly Asp Asp Leu Arg Asn Thr Lys His
370                 375                 380

Glu Ile Ser Glu Met Asn Arg Met Ile Gln Arg Leu Arg Ala Glu Ile
385                 390                 395                 400

Asp Asn Val Lys Lys Gln Cys Ala Asn Leu Gln Asn Ala Ile Ala Asp
                405                 410                 415

Ala Glu Gln Arg Gly Glu Leu Ala Leu Lys Asp Ala Arg Asn Lys Leu
                420                 425                 430

Ala Glu Leu Glu Glu Ala Leu Gln Lys Ala Lys Gln Asp Met Ala Arg
            435                 440                 445

Leu Leu Arg Glu Tyr Gln Glu Leu Met Asn Thr Lys Leu Ala Leu Asp
    450                 455                 460

Val Glu Ile Ala Thr Tyr Arg Lys Leu Leu Glu Gly Glu Glu Cys Arg
465                 470                 475                 480

Leu Ser Gly Glu Gly Val Gly Pro Val Asn Ile Ser Val Val Thr Ser
                485                 490                 495

Ser Val Ser Ser Gly Tyr Gly Ser Gly Ser Gly Tyr Gly Gly Gly Leu
                500                 505                 510

Gly Gly Gly Leu Gly Gly Gly Leu Gly Gly Gly Leu Ala Gly Gly Ser
            515                 520                 525

Ser Gly Ser Tyr Tyr Ser Ser Ser Ser Gly Gly Val Gly Leu Gly Gly
    530                 535                 540

Gly Leu Ser Val Gly Gly Ser Gly Phe Ser Ala Ser Ser Gly Arg Gly
545                 550                 555                 560

Leu Gly Val Gly Phe Gly Ser Gly Gly Gly Ser Ser Ser Ser Val Lys
                565                 570                 575

Phe Val Ser Thr Thr Ser Ser Ser Arg Lys Ser Phe Lys Ser
                580                 585                 590

<210> SEQ ID NO 34
<211> LENGTH: 511
<212> TYPE: PRT
<213> ORGANISM: homo sapiens

<400> SEQUENCE: 34

Met Asn Gly Val Ser Trp Ser Gln Asp Leu Gln Glu Gly Ile Ser Ala
1               5                   10                  15

Trp Phe Gly Pro Pro Ala Ser Thr Pro Ala Ser Thr Met Ser Ile Arg
                20                  25                  30

Val Thr Gln Lys Ser Tyr Lys Val Ser Thr Ser Gly Pro Arg Ala Phe
            35                  40                  45

Ser Ser Arg Ser Tyr Thr Ser Gly Pro Gly Ser Arg Ile Ser Ser Ser
    50                  55                  60

Ser Phe Ser Arg Val Gly Ser Ser Asn Phe Arg Gly Gly Leu Gly Gly
65                  70                  75                  80

Gly Tyr Gly Gly Ala Ser Gly Met Gly Gly Ile Thr Ala Val Thr Val
                85                  90                  95

Asn Gln Ser Leu Leu Ser Pro Leu Val Leu Glu Val Asp Pro Asn Ile
                100                 105                 110

Gln Ala Val Arg Thr Gln Glu Lys Glu Gln Ile Lys Thr Leu Asn Asn
            115                 120                 125

Lys Phe Ala Ser Phe Ile Asp Lys Val Arg Phe Leu Glu Gln Gln Asn
    130                 135                 140

Lys Met Leu Glu Thr Lys Trp Ser Leu Leu Gln Gln Gln Lys Thr Ala
145                 150                 155                 160

Arg Ser Asn Met Asp Asn Met Phe Glu Ser Tyr Ile Asn Asn Leu Arg
                165                 170                 175

Arg Gln Leu Glu Thr Leu Gly Gln Glu Lys Leu Lys Leu Glu Ala Glu
            180                 185                 190

Leu Gly Asn Met Gln Gly Leu Val Glu Asp Phe Lys Asn Lys Tyr Glu

```
                    195                 200                 205
Asp Glu Ile Asn Lys Arg Thr Glu Met Glu Asn Glu Phe Val Leu Ile
210                 215                 220

Lys Lys Asp Val Asp Glu Ala Tyr Met Asn Lys Val Glu Leu Glu Ser
225                 230                 235                 240

Arg Leu Glu Gly Leu Thr Asp Glu Ile Asn Phe Leu Arg Gln Leu Tyr
                245                 250                 255

Glu Glu Glu Ile Arg Glu Leu Gln Ser Gln Ile Ser Asp Thr Ser Val
                260                 265                 270

Val Leu Ser Met Asp Asn Ser Arg Ser Leu Asp Met Asp Ser Ile Ile
                275                 280                 285

Ala Glu Val Lys Ala Gln Tyr Glu Asp Ile Ala Asn Arg Ser Arg Ala
290                 295                 300

Glu Ala Glu Ser Met Tyr Gln Ile Lys Tyr Glu Glu Leu Gln Ser Leu
305                 310                 315                 320

Ala Gly Lys His Gly Asp Asp Leu Arg Arg Thr Lys Thr Glu Ile Ser
                325                 330                 335

Glu Met Asn Arg Asn Ile Ser Arg Leu Gln Ala Glu Ile Glu Gly Leu
                340                 345                 350

Lys Gly Gln Arg Ala Ser Leu Glu Ala Ala Ile Ala Asp Ala Glu Gln
                355                 360                 365

Arg Gly Glu Leu Ala Ile Lys Asp Ala Asn Ala Lys Leu Ser Glu Leu
                370                 375                 380

Glu Ala Ala Leu Gln Arg Ala Lys Gln Asp Met Ala Arg Gln Leu Arg
385                 390                 395                 400

Glu Tyr Gln Glu Leu Met Asn Val Lys Leu Ala Leu Asp Ile Glu Ile
                405                 410                 415

Ala Thr Tyr Arg Lys Leu Leu Glu Gly Glu Ser Arg Leu Glu Ser
                420                 425                 430

Gly Met Gln Asn Met Ser Ile His Thr Lys Thr Thr Ser Gly Tyr Ala
                435                 440                 445

Gly Gly Leu Ser Ser Ala Tyr Gly Gly Leu Thr Ser Pro Gly Leu Ser
                450                 455                 460

Tyr Ser Leu Gly Ser Ser Phe Gly Ser Gly Ala Gly Ser Ser Ser Phe
465                 470                 475                 480

Ser Arg Thr Ser Ser Arg Ala Val Val Val Lys Lys Ile Glu Thr
                485                 490                 495

Arg Asp Gly Lys Leu Val Ser Glu Ser Ser Asp Val Leu Pro Lys
                500                 505                 510

<210> SEQ ID NO 35
<211> LENGTH: 525
<212> TYPE: PRT
<213> ORGANISM: homo sapiens

<400> SEQUENCE: 35

Met Trp Ala Val Leu Arg Leu Ala Leu Arg Pro Cys Ala Arg Ala Ser
1               5                   10                  15

Pro Ala Gly Pro Arg Ala Tyr His Gly Asp Ser Val Ala Ser Leu Gly
                20                  25                  30

Thr Gln Pro Asp Leu Gly Ser Ala Leu Tyr Gln Glu Asn Tyr Lys Gln
                35                  40                  45

Met Lys Ala Leu Val Asn Gln Leu His Glu Arg Val Glu His Ile Lys
50                  55                  60
```

```
Leu Gly Gly Gly Glu Lys Ala Arg Ala Leu His Ile Ser Arg Gly Lys
 65                  70                  75                  80

Leu Leu Pro Arg Glu Arg Ile Asp Asn Leu Ile Asp Pro Gly Ser Pro
                 85                  90                  95

Phe Leu Glu Leu Ser Gln Phe Ala Gly Tyr Gln Leu Tyr Asp Asn Glu
            100                 105                 110

Glu Val Pro Gly Gly Gly Ile Ile Thr Gly Ile Gly Arg Val Ser Gly
        115                 120                 125

Val Glu Cys Met Ile Ile Ala Asn Asp Ala Thr Val Lys Gly Gly Ala
130                 135                 140

Tyr Tyr Pro Val Thr Val Lys Lys Gln Leu Arg Ala Gln Glu Ile Ala
145                 150                 155                 160

Met Gln Asn Arg Leu Pro Cys Ile Tyr Leu Val Asp Ser Gly Gly Ala
                165                 170                 175

Tyr Leu Pro Arg Gln Ala Asp Val Phe Pro Asp Arg Asp His Phe Gly
            180                 185                 190

Arg Thr Phe Tyr Asn Gln Ala Ile Met Ser Ser Lys Asn Ile Ala Gln
        195                 200                 205

Val Lys Ala Ala Thr Gly Glu Glu Val Ser Ala Glu Asp Leu Gly Gly
210                 215                 220

Ala Asp Leu His Cys Arg Lys Ser Gly Val Ser Asp His Trp Ala Leu
225                 230                 235                 240

Asp Asp His His Ala Leu His Leu Thr Arg Lys Val Val Arg Asn Leu
                245                 250                 255

Asn Tyr Gln Lys Lys Leu Asp Val Thr Ile Glu Pro Ser Glu Glu Pro
            260                 265                 270

Leu Phe Pro Ala Asp Glu Leu Tyr Gly Ile Val Gly Ala Asn Leu Lys
        275                 280                 285

Arg Ser Phe Asp Val Arg Glu Val Ile Ala Arg Ile Val Asp Gly Ser
290                 295                 300

Arg Phe Thr Glu Phe Lys Ala Phe Tyr Gly Asp Thr Leu Val Thr Gly
305                 310                 315                 320

Phe Ala Arg Ile Phe Gly Tyr Pro Val Gly Ile Val Gly Asn Asn Gly
                325                 330                 335

Val Leu Phe Ser Glu Ser Ala Lys Lys Gly Thr His Phe Val Gln Leu
            340                 345                 350

Cys Cys Gln Arg Asn Ile Pro Leu Leu Phe Leu Gln Asn Ile Thr Gly
        355                 360                 365

Phe Met Val Gly Arg Glu Tyr Glu Ala Glu Gly Ile Ala Lys Asp Gly
370                 375                 380

Ala Lys Met Val Ala Ala Val Ala Cys Ala Gln Val Pro Lys Ile Thr
385                 390                 395                 400

Leu Ile Ile Gly Gly Ser Tyr Gly Ala Gly Asn Tyr Gly Met Cys Gly
                405                 410                 415

Arg Ala Tyr Ser Pro Arg Phe Leu Tyr Ile Trp Pro Asn Ala Arg Ile
            420                 425                 430

Ser Val Met Gly Gly Glu Gln Ala Ala Asn Val Leu Ala Thr Ile Thr
        435                 440                 445

Lys Asp Gln Arg Ala Arg Glu Gly Lys Gln Phe Ser Ser Ala Asp Glu
450                 455                 460

Ala Ala Leu Lys Glu Pro Ile Ile Lys Lys Phe Glu Glu Glu Gly Asn
465                 470                 475                 480

Pro Tyr Tyr Ser Ser Ala Arg Val Trp Asp Asp Gly Ile Ile Asp Pro
```

```
                    485              490              495
Ala Asp Thr Arg Leu Val Leu Gly Leu Ser Phe Ser Ala Ala Leu Asn
                500              505              510
Ala Pro Ile Glu Lys Thr Asp Phe Gly Ile Phe Arg Met
                515              520              525

<210> SEQ ID NO 36
<211> LENGTH: 335
<212> TYPE: PRT
<213> ORGANISM: homo sapiens

<400> SEQUENCE: 36

Met Pro Arg Pro Arg Leu Leu Ala Ala Leu Cys Gly Ala Leu Leu Cys
1               5                   10                  15
Ala Pro Ser Leu Leu Val Ala Leu Asp Ile Cys Ser Lys Asn Pro Cys
                20                  25                  30
His Asn Gly Gly Leu Cys Glu Glu Ile Ser Gln Glu Val Arg Gly Asp
            35                  40                  45
Val Phe Pro Ser Tyr Thr Cys Thr Cys Leu Lys Gly Tyr Ala Gly Asn
        50                  55                  60
His Cys Glu Thr Lys Cys Val Glu Pro Leu Gly Leu Glu Asn Gly Asn
65                  70                  75                  80
Ile Ala Asn Ser Gln Ile Ala Ala Ser Ser Val Arg Val Thr Phe Leu
                85                  90                  95
Gly Leu Gln His Trp Val Pro Glu Leu Ala Arg Leu Asn Arg Ala Gly
                100                 105                 110
Met Val Asn Ala Trp Thr Pro Ser Ser Asn Asp Asp Asn Pro Trp Ile
            115                 120                 125
Gln Val Asn Leu Leu Arg Arg Met Trp Val Thr Gly Val Val Thr Gln
        130                 135                 140
Gly Ala Ser Arg Leu Ala Ser His Glu Tyr Leu Lys Ala Phe Lys Val
145                 150                 155                 160
Ala Tyr Ser Leu Asn Gly His Glu Phe Asp Phe Ile His Asp Val Asn
                165                 170                 175
Lys Lys His Lys Glu Phe Val Gly Asn Trp Asn Lys Asn Ala Val His
            180                 185                 190
Val Asn Leu Phe Glu Thr Pro Val Glu Ala Gln Tyr Val Arg Leu Tyr
        195                 200                 205
Pro Thr Ser Cys His Thr Ala Cys Thr Leu Arg Phe Glu Leu Leu Gly
        210                 215                 220
Cys Glu Leu Asn Gly Cys Ala Asn Pro Leu Gly Leu Lys Asn Asn Ser
225                 230                 235                 240
Ile Pro Asp Lys Gln Ile Thr Ala Ser Ser Tyr Lys Thr Trp Gly
                245                 250                 255
Leu His Leu Phe Ser Trp Asn Pro Ser Tyr Ala Arg Leu Asp Lys Gln
                260                 265                 270
Gly Asn Phe Asn Ala Trp Val Ala Gly Ser Tyr Gly Asn Asp Gln Trp
            275                 280                 285
Leu Gln Ile Phe Pro Gly Asn Trp Asp Asn His Ser His Lys Lys Asn
        290                 295                 300
Leu Phe Glu Thr Pro Ile Leu Ala Arg Tyr Val Arg Ile Leu Pro Val
305                 310                 315                 320
Ala Trp His Asn Arg Ile Ala Leu Arg Leu Glu Leu Leu Gly Cys
                325                 330                 335
```

<210> SEQ ID NO 37
<211> LENGTH: 644
<212> TYPE: PRT
<213> ORGANISM: homo sapiens

<400> SEQUENCE: 37

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380
```

```
Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
        420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
            485                 490                 495

Gly Ile Ile Ile Gln Gly Gly Lys His Arg Glu Asn Lys Val Phe Met
        500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
            565                 570                 575

Arg Met Glu Leu Leu Gly Cys Glu Val Glu Ala Pro Thr Ala Gly Pro
        580                 585                 590

Thr Thr Pro Asn Gly Asn Leu Val Asp Glu Cys Asp Asp Asp Gln Ala
            595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Gly Ile Lys

<210> SEQ ID NO 38
<211> LENGTH: 4515
<212> TYPE: PRT
<213> ORGANISM: homo sapiens

<400> SEQUENCE: 38

Met Lys Ile Val Pro Asp Glu Arg Asp Arg Val Gln Lys Lys Thr Phe
1               5                   10                  15

Thr Lys Trp Val Asn Lys His Leu Ile Lys Ala Gln Arg His Ile Ser
            20                  25                  30

Asp Leu Tyr Glu Asp Leu Arg Asp Gly His Asn Leu Ile Ser Leu Leu
        35                  40                  45

Glu Val Leu Ser Gly Asp Ser Leu Pro Arg Glu Lys Gly Arg Met Arg
50                  55                  60

Phe His Lys Leu Gln Asn Val Gln Ile Ala Leu Asp Tyr Leu Arg His
65                  70                  75                  80

Arg Gln Val Lys Leu Val Asn Ile Arg Asn Asp Asp Ile Ala Asp Gly
            85                  90                  95

Asn Pro Lys Leu Thr Leu Gly Leu Ile Trp Thr Ile Ile Leu His Phe
        100                 105                 110
```

```
Gln Ile Ser Asp Ile Gln Val Ser Gly Gln Ser Glu Asp Met Thr Ala
            115                 120                 125
Lys Glu Lys Leu Leu Trp Ser Gln Arg Met Val Glu Gly Tyr Gln
130                 135                 140
Gly Leu Arg Cys Asp Asn Phe Thr Ser Ser Trp Arg Asp Gly Arg Leu
145                 150                 155                 160
Phe Asn Ala Ile Ile His Arg His Lys Pro Leu Leu Ile Asp Met Asn
                165                 170                 175
Lys Val Tyr Arg Gln Thr Asn Leu Glu Asn Leu Asp Gln Ala Phe Ser
                180                 185                 190
Val Ala Glu Arg Asp Leu Gly Val Thr Arg Leu Leu Asp Pro Glu Asp
                195                 200                 205
Val Asp Val Pro Gln Pro Asp Glu Lys Ser Ile Ile Thr Tyr Val Ser
210                 215                 220
Ser Leu Tyr Asp Ala Met Pro Arg Val Pro Asp Val Gln Asp Gly Val
225                 230                 235                 240
Arg Ala Asn Glu Leu Gln Leu Arg Trp Gln Glu Tyr Arg Glu Leu Val
                245                 250                 255
Leu Leu Leu Leu Gln Trp Met Arg His His Thr Ala Ala Phe Glu Glu
                260                 265                 270
Arg Arg Phe Pro Ser Ser Phe Glu Glu Ile Glu Ile Leu Trp Ser Gln
            275                 280                 285
Phe Leu Lys Phe Lys Glu Met Glu Leu Pro Ala Lys Glu Ala Asp Lys
            290                 295                 300
Asn Arg Ser Lys Gly Ile Tyr Gln Ser Leu Glu Gly Ala Val Gln Ala
305                 310                 315                 320
Gly Gln Leu Lys Val Pro Pro Gly Tyr His Pro Leu Asp Val Glu Lys
                325                 330                 335
Glu Trp Gly Lys Leu His Val Ala Ile Leu Glu Arg Glu Lys Gln Leu
                340                 345                 350
Arg Ser Glu Phe Glu Arg Leu Glu Cys Leu Gln Arg Ile Val Thr Lys
            355                 360                 365
Leu Gln Met Glu Ala Gly Leu Cys Glu Glu Gln Leu Asn Gln Ala Asp
            370                 375                 380
Ala Leu Leu Gln Ser Asp Val Arg Leu Leu Ala Ala Gly Lys Val Pro
385                 390                 395                 400
Gln Arg Ala Gly Glu Val Glu Arg Asp Leu Asp Lys Ala Asp Ser Met
                405                 410                 415
Ile Arg Leu Leu Phe Asn Asp Val Gln Thr Leu Lys Asp Gly Arg His
                420                 425                 430
Pro Gln Gly Glu Gln Met Tyr Arg Arg Val Tyr Arg Leu His Glu Arg
            435                 440                 445
Leu Val Ala Ile Arg Thr Glu Tyr Asn Leu Arg Leu Lys Ala Gly Val
            450                 455                 460
Ala Ala Pro Ala Thr Gln Val Ala Gln Val Thr Leu Gln Ser Val Gln
465                 470                 475                 480
Arg Arg Pro Glu Leu Glu Asp Ser Thr Leu Arg Tyr Leu Gln Asp Leu
                485                 490                 495
Leu Ala Trp Val Glu Glu Asn Gln His Arg Val Asp Gly Ala Glu Trp
                500                 505                 510
Gly Val Asp Leu Pro Ser Val Glu Ala Gln Leu Gly Ser His Arg Gly
            515                 520                 525
```

```
Leu His Gln Ser Ile Glu Glu Phe Arg Ala Lys Ile Glu Arg Ala Arg
    530                 535                 540

Ser Asp Glu Gly Gln Leu Ser Pro Ala Thr Arg Gly Ala Tyr Arg Asp
545                 550                 555                 560

Cys Leu Gly Arg Leu Asp Leu Gln Tyr Ala Lys Leu Leu Asn Ser Ser
                565                 570                 575

Lys Ala Arg Leu Arg Ser Leu Glu Ser Leu His Ser Phe Val Ala Ala
            580                 585                 590

Ala Thr Lys Glu Leu Met Trp Leu Asn Glu Lys Glu Glu Glu Val
        595                 600                 605

Gly Phe Asp Trp Ser Asp Arg Asn Thr Asn Met Thr Ala Lys Lys Glu
    610                 615                 620

Ser Tyr Ser Ala Leu Met Arg Glu Leu Glu Leu Lys Glu Lys Lys Ile
625                 630                 635                 640

Lys Glu Leu Gln Asn Ala Gly Asp Arg Leu Leu Arg Glu Asp His Pro
                645                 650                 655

Ala Arg Pro Thr Val Glu Ser Phe Gln Ala Ala Leu Gln Thr Gln Trp
            660                 665                 670

Ser Trp Met Leu Gln Leu Cys Cys Cys Ile Glu Ala His Leu Lys Glu
    675                 680                 685

Asn Ala Ala Tyr Phe Gln Phe Phe Ser Asp Val Arg Glu Ala Glu Gly
    690                 695                 700

Gln Leu Gln Lys Leu Gln Glu Ala Leu Arg Arg Lys Tyr Ser Cys Asp
705                 710                 715                 720

Arg Ser Ala Thr Val Thr Arg Leu Glu Asp Leu Leu Gln Asp Ala Gln
                725                 730                 735

Asp Glu Lys Glu Gln Leu Asn Glu Tyr Lys Gly His Leu Ser Gly Leu
            740                 745                 750

Ala Lys Arg Ala Lys Ala Val Val Gln Leu Lys Pro Arg His Pro Ala
    755                 760                 765

His Pro Met Arg Gly Arg Leu Pro Leu Leu Ala Val Cys Asp Tyr Lys
    770                 775                 780

Gln Val Glu Val Thr Val His Lys Gly Asp Glu Cys Gln Leu Val Gly
785                 790                 795                 800

Pro Ala Gln Pro Ser His Trp Lys Val Leu Ser Ser Gly Ser Glu
                805                 810                 815

Ala Ala Val Pro Ser Val Cys Phe Leu Val Pro Pro Asn Gln Glu
            820                 825                 830

Ala Gln Glu Ala Val Thr Arg Leu Glu Ala Gln His Gln Ala Leu Val
    835                 840                 845

Thr Leu Trp His Gln Leu His Val Asp Met Lys Ser Leu Leu Ala Trp
    850                 855                 860

Gln Ser Leu Arg Arg Asp Val Gln Leu Ile Arg Ser Trp Ser Leu Ala
865                 870                 875                 880

Thr Phe Arg Thr Leu Lys Pro Glu Glu Gln Arg Gln Ala Leu His Ser
                885                 890                 895

Leu Glu Leu His Tyr Gln Ala Phe Leu Arg Asp Ser Gln Asp Ala Gly
            900                 905                 910

Gly Phe Gly Pro Glu Asp Arg Leu Met Ala Glu Arg Tyr Gly Ser
    915                 920                 925

Cys Ser His His Tyr Gln Gln Leu Leu Gln Ser Leu Glu Gln Gly Ala
    930                 935                 940

Gln Glu Glu Ser Arg Cys Gln Arg Cys Ile Ser Glu Leu Lys Asp Ile
```

```
                 945                 950                 955                 960
           Arg Leu Gln Leu Glu Ala Cys Glu Thr Arg Thr Val His Arg Leu Arg
                           965                 970                 975
           Leu Pro Leu Asp Lys Glu Pro Ala Arg Glu Cys Ala Gln Arg Ile Ala
                           980                 985                 990
           Glu Gln Gln Lys Ala Gln Ala Glu Val Glu Gly Leu Gly Lys Gly Val
                           995                 1000                1005
           Ala Arg Leu Ser Ala Glu Ala Glu Lys Val Leu Ala Leu Pro Glu
                   1010                1015                1020
           Pro Ser Pro Ala Ala Pro Thr Leu Arg Ser Glu Leu Glu Leu Thr
                   1025                1030                1035
           Leu Gly Lys Leu Glu Gln Val Arg Ser Leu Ser Ala Ile Tyr Leu
                   1040                1045                1050
           Glu Lys Leu Lys Thr Ile Ser Leu Val Ile Arg Gly Thr Gln Gly
                   1055                1060                1065
           Ala Glu Glu Val Leu Arg Ala His Glu Glu Gln Leu Lys Glu Ala
                   1070                1075                1080
           Gln Ala Val Pro Ala Thr Leu Pro Glu Leu Glu Ala Thr Lys Ala
                   1085                1090                1095
           Ser Leu Lys Lys Leu Arg Ala Gln Ala Glu Ala Gln Gln Pro Thr
                   1100                1105                1110
           Phe Asp Ala Leu Arg Asp Glu Leu Arg Gly Ala Gln Glu Val Gly
                   1115                1120                1125
           Glu Arg Leu Gln Gln Arg His Gly Glu Arg Asp Val Glu Val Glu
                   1130                1135                1140
           Arg Trp Arg Glu Arg Val Ala Gln Leu Leu Glu Arg Trp Gln Ala
                   1145                1150                1155
           Val Leu Ala Gln Thr Asp Val Arg Gln Arg Glu Leu Glu Gln Leu
                   1160                1165                1170
           Gly Arg Gln Leu Arg Tyr Tyr Arg Glu Ser Ala Asp Pro Leu Gly
                   1175                1180                1185
           Ala Trp Leu Gln Asp Ala Arg Arg Arg Gln Glu Gln Ile Gln Ala
                   1190                1195                1200
           Met Pro Leu Ala Asp Ser Gln Ala Val Arg Glu Gln Leu Arg Gln
                   1205                1210                1215
           Glu Gln Ala Leu Leu Glu Glu Ile Glu Arg His Gly Glu Lys Val
                   1220                1225                1230
           Glu Glu Cys Gln Arg Phe Ala Lys Gln Tyr Ile Asn Ala Ile Lys
                   1235                1240                1245
           Asp Tyr Glu Leu Gln Leu Val Thr Tyr Lys Ala Gln Leu Glu Pro
                   1250                1255                1260
           Val Ala Ser Pro Ala Lys Lys Pro Lys Val Gln Ser Gly Ser Glu
                   1265                1270                1275
           Ser Val Ile Gln Glu Tyr Val Asp Leu Arg Thr His Tyr Ser Glu
                   1280                1285                1290
           Leu Thr Thr Leu Thr Ser Gln Tyr Ile Lys Phe Ile Ser Glu Thr
                   1295                1300                1305
           Leu Arg Arg Met Glu Glu Glu Arg Leu Ala Glu Gln Gln Arg
                   1310                1315                1320
           Ala Glu Glu Arg Glu Arg Leu Ala Glu Val Glu Ala Ala Leu Glu
                   1325                1330                1335
           Lys Gln Arg Gln Leu Ala Glu Ala His Ala Gln Ala Lys Ala Gln
                   1340                1345                1350
```

-continued

Ala Glu Arg Glu Ala Lys Glu Leu Gln Gln Arg Met Gln Glu Glu
1355                1360                1365

Val Val Arg Arg Glu Glu Ala Ala Val Asp Ala Gln Gln Gln Lys
1370                1375                1380

Arg Ser Ile Gln Glu Glu Leu Gln Gln Leu Arg Gln Ser Ser Glu
1385                1390                1395

Ala Glu Ile Gln Ala Lys Ala Arg Gln Ala Glu Ala Ala Glu Arg
1400                1405                1410

Ser Arg Leu Arg Ile Glu Glu Glu Ile Arg Val Val Arg Leu Gln
1415                1420                1425

Leu Glu Ala Thr Glu Arg Arg Gly Gly Ala Glu Gly Glu Leu
1430                1435                1440

Gln Ala Leu Arg Ala Arg Ala Glu Glu Ala Glu Ala Gln Lys Arg
1445                1450                1455

Gln Ala Gln Glu Glu Ala Glu Arg Leu Arg Arg Gln Val Gln Asp
1460                1465                1470

Glu Ser Gln Arg Lys Arg Gln Ala Glu Val Glu Leu Ala Ser Arg
1475                1480                1485

Val Lys Ala Glu Ala Glu Ala Ala Arg Glu Lys Gln Arg Ala Leu
1490                1495                1500

Gln Ala Leu Glu Glu Leu Arg Leu Gln Ala Glu Glu Ala Glu Arg
1505                1510                1515

Arg Leu Arg Gln Ala Glu Val Glu Arg Ala Arg Gln Val Gln Val
1520                1525                1530

Ala Leu Glu Thr Ala Gln Arg Ser Ala Glu Ala Glu Leu Gln Ser
1535                1540                1545

Lys Arg Ala Ser Phe Ala Glu Lys Thr Ala Gln Leu Glu Arg Ser
1550                1555                1560

Leu Gln Glu Glu His Val Ala Val Ala Gln Leu Arg Glu Glu Ala
1565                1570                1575

Glu Arg Arg Ala Gln Gln Gln Ala Glu Ala Glu Arg Ala Arg Glu
1580                1585                1590

Glu Ala Glu Arg Glu Leu Glu Arg Trp Gln Leu Lys Ala Asn Glu
1595                1600                1605

Ala Leu Arg Leu Arg Leu Gln Ala Glu Glu Val Ala Gln Gln Lys
1610                1615                1620

Ser Leu Ala Gln Ala Glu Ala Glu Lys Gln Lys Glu Glu Ala Glu
1625                1630                1635

Arg Glu Ala Arg Arg Arg Gly Lys Ala Glu Glu Gln Ala Val Arg
1640                1645                1650

Gln Arg Glu Leu Ala Glu Gln Glu Leu Glu Lys Gln Arg Gln Leu
1655                1660                1665

Ala Glu Gly Thr Ala Gln Gln Arg Leu Ala Ala Glu Gln Glu Leu
1670                1675                1680

Ile Arg Leu Arg Ala Glu Thr Glu Gln Gly Glu Gln Gln Arg Gln
1685                1690                1695

Leu Leu Glu Glu Glu Leu Ala Arg Leu Gln Arg Glu Ala Ala Ala
1700                1705                1710

Ala Thr Gln Lys Arg Gln Glu Leu Glu Ala Glu Leu Ala Lys Val
1715                1720                1725

Arg Ala Glu Met Glu Val Leu Leu Ala Ser Lys Ala Arg Ala Glu
1730                1735                1740

-continued

```
Glu Glu Ser Arg Ser Thr Ser Glu Lys Ser Lys Gln Arg Leu Glu
1745                1750                1755

Ala Glu Ala Gly Arg Phe Arg Glu Leu Ala Glu Glu Ala Ala Arg
1760                1765                1770

Leu Arg Ala Leu Ala Glu Glu Ala Lys Arg Gln Arg Gln Leu Ala
    1775                1780                1785

Glu Glu Asp Ala Ala Arg Gln Arg Ala Glu Ala Glu Arg Val Leu
1790                1795                1800

Ala Glu Lys Leu Ala Ala Ile Gly Glu Ala Thr Arg Leu Lys Thr
1805                1810                1815

Glu Ala Glu Ile Ala Leu Lys Glu Lys Glu Ala Glu Asn Glu Arg
1820                1825                1830

Leu Arg Arg Leu Ala Glu Asp Glu Ala Phe Gln Arg Arg Arg Leu
    1835                1840                1845

Glu Glu Gln Ala Ala Gln His Lys Ala Asp Ile Glu Glu Arg Leu
1850                1855                1860

Ala Gln Leu Arg Lys Ala Ser Asp Ser Glu Leu Glu Arg Gln Lys
1865                1870                1875

Gly Leu Val Glu Asp Thr Leu Arg Gln Arg Arg Gln Val Glu Glu
1880                1885                1890

Glu Ile Leu Ala Leu Lys Ala Ser Phe Glu Lys Ala Ala Ala Gly
1895                1900                1905

Lys Ala Glu Leu Glu Leu Glu Leu Gly Arg Ile Arg Ser Asn Ala
1910                1915                1920

Glu Asp Thr Leu Arg Ser Lys Glu Gln Ala Glu Leu Glu Ala Ala
1925                1930                1935

Arg Gln Arg Gln Leu Ala Ala Glu Glu Glu Arg Arg Arg Arg Glu
    1940                1945                1950

Ala Glu Glu Arg Val Gln Lys Ser Leu Ala Ala Glu Glu Glu Ala
1955                1960                1965

Ala Arg Gln Arg Lys Ala Ala Leu Glu Glu Val Glu Arg Leu Lys
1970                1975                1980

Ala Lys Val Glu Glu Ala Arg Arg Leu Arg Glu Arg Ala Glu Gln
1985                1990                1995

Glu Ser Ala Arg Gln Leu Gln Leu Ala Gln Glu Ala Ala Gln Lys
2000                2005                2010

Arg Leu Gln Ala Glu Glu Lys Ala His Ala Phe Ala Val Gln Gln
    2015                2020                2025

Lys Glu Gln Glu Leu Gln Gln Thr Leu Gln Gln Glu Gln Ser Val
2030                2035                2040

Leu Asp Gln Leu Arg Gly Glu Ala Glu Ala Ala Arg Arg Ala Ala
2045                2050                2055

Glu Glu Ala Glu Glu Ala Arg Val Gln Ala Glu Arg Glu Ala Ala
2060                2065                2070

Gln Ser Arg Arg Gln Val Glu Glu Ala Glu Arg Leu Lys Gln Ser
2075                2080                2085

Ala Glu Glu Gln Ala Gln Ala Arg Ala Gln Ala Gln Ala Ala Ala
2090                2095                2100

Glu Lys Leu Arg Lys Glu Ala Glu Gln Glu Ala Ala Arg Arg Ala
2105                2110                2115

Gln Ala Glu Gln Ala Ala Leu Arg Gln Lys Gln Ala Ala Asp Ala
2120                2125                2130

Glu Met Glu Lys His Lys Lys Phe Ala Glu Gln Thr Leu Arg Gln
```

```
            2135                2140                2145
Lys Ala Gln Val Glu Gln Glu Leu Thr Thr Leu Arg Leu Gln Leu
        2150                2155                2160
Glu Glu Thr Asp His Gln Lys Asn Leu Leu Asp Glu Glu Leu Gln
        2165                2170                2175
Arg Leu Lys Ala Glu Ala Thr Glu Ala Ala Arg Gln Arg Ser Gln
        2180                2185                2190
Val Glu Glu Glu Leu Phe Ser Val Arg Val Gln Met Glu Glu Leu
        2195                2200                2205
Ser Lys Leu Lys Ala Arg Ile Glu Ala Glu Asn Arg Ala Leu Ile
        2210                2215                2220
Leu Arg Asp Lys Asp Asn Thr Gln Arg Phe Leu Gln Glu Glu Ala
        2225                2230                2235
Glu Lys Met Lys Gln Val Ala Glu Glu Ala Ala Arg Leu Ser Val
        2240                2245                2250
Ala Ala Gln Glu Ala Ala Arg Leu Arg Gln Leu Ala Glu Glu Asp
        2255                2260                2265
Leu Ala Gln Gln Arg Ala Leu Ala Glu Lys Met Leu Lys Glu Lys
        2270                2275                2280
Met Gln Ala Val Gln Glu Ala Thr Arg Leu Lys Ala Glu Ala Glu
        2285                2290                2295
Leu Leu Gln Gln Gln Lys Glu Leu Ala Gln Glu Gln Ala Arg Arg
        2300                2305                2310
Leu Gln Glu Asp Lys Glu Gln Met Ala Gln Gln Leu Ala Glu Glu
        2315                2320                2325
Thr Gln Gly Phe Gln Arg Thr Leu Glu Ala Glu Arg Gln Arg Gln
        2330                2335                2340
Leu Glu Met Ser Ala Glu Ala Glu Arg Leu Lys Leu Arg Val Ala
        2345                2350                2355
Glu Met Ser Arg Ala Gln Ala Arg Ala Glu Glu Asp Ala Gln Arg
        2360                2365                2370
Phe Arg Lys Gln Ala Glu Glu Ile Gly Glu Lys Leu His Arg Thr
        2375                2380                2385
Glu Leu Ala Thr Gln Glu Lys Val Thr Leu Val Gln Thr Leu Glu
        2390                2395                2400
Ile Gln Arg Gln Gln Ser Asp His Asp Ala Glu Arg Leu Arg Glu
        2405                2410                2415
Ala Ile Ala Glu Leu Glu Arg Glu Lys Glu Lys Leu Gln Gln Glu
        2420                2425                2430
Ala Lys Leu Leu Gln Leu Lys Ser Glu Glu Met Gln Thr Val Gln
        2435                2440                2445
Gln Glu Gln Leu Leu Gln Glu Thr Gln Ala Leu Gln Gln Ser Phe
        2450                2455                2460
Leu Ser Glu Lys Asp Ser Leu Leu Gln Arg Glu Arg Phe Ile Glu
        2465                2470                2475
Gln Glu Lys Ala Lys Leu Glu Gln Leu Phe Gln Asp Glu Val Ala
        2480                2485                2490
Lys Ala Gln Gln Leu Arg Glu Glu Gln Gln Arg Gln Gln Gln Gln
        2495                2500                2505
Met Glu Gln Glu Arg Gln Arg Leu Val Ala Ser Met Glu Glu Ala
        2510                2515                2520
Arg Arg Arg Gln His Glu Ala Glu Glu Gly Val Arg Arg Lys Gln
        2525                2530                2535
```

```
Glu Glu Leu Gln Gln Leu Glu Gln Gln Arg Arg Gln Gln Glu Glu
    2540                2545                2550

Leu Leu Ala Glu Glu Asn Gln Arg Leu Arg Glu Gln Leu Gln Leu
    2555                2560                2565

Leu Glu Glu Gln His Arg Ala Ala Leu Ala His Ser Glu Glu Val
    2570                2575                2580

Thr Ala Ser Gln Val Ala Ala Thr Lys Thr Leu Pro Asn Gly Arg
    2585                2590                2595

Asp Ala Leu Asp Gly Pro Ala Ala Glu Ala Glu Pro Glu His Ser
    2600                2605                2610

Phe Asp Gly Leu Arg Arg Lys Val Ser Ala Gln Arg Leu Gln Glu
    2615                2620                2625

Ala Gly Ile Leu Ser Ala Glu Glu Leu Gln Arg Leu Ala Gln Gly
    2630                2635                2640

His Thr Thr Val Asp Glu Leu Ala Arg Arg Glu Asp Val Arg His
    2645                2650                2655

Tyr Leu Gln Gly Arg Ser Ser Ile Ala Gly Leu Leu Leu Lys Ala
    2660                2665                2670

Thr Asn Glu Lys Leu Ser Val Tyr Ala Ala Leu Gln Arg Gln Leu
    2675                2680                2685

Leu Ser Pro Gly Thr Ala Leu Ile Leu Leu Glu Ala Gln Ala Ala
    2690                2695                2700

Ser Gly Phe Leu Leu Asp Pro Val Arg Asn Arg Arg Leu Thr Val
    2705                2710                2715

Asn Glu Ala Val Lys Glu Gly Val Val Gly Pro Glu Leu His His
    2720                2725                2730

Lys Leu Leu Ser Ala Glu Arg Ala Val Thr Gly Tyr Lys Asp Pro
    2735                2740                2745

Tyr Thr Gly Gln Gln Ile Ser Leu Phe Gln Ala Met Gln Lys Gly
    2750                2755                2760

Leu Ile Val Arg Glu His Gly Ile Arg Leu Leu Glu Ala Gln Ile
    2765                2770                2775

Ala Thr Gly Gly Val Ile Asp Pro Val His Ser His Arg Val Pro
    2780                2785                2790

Val Asp Val Ala Tyr Arg Arg Gly Tyr Phe Asp Glu Glu Met Asn
    2795                2800                2805

Arg Val Leu Ala Asp Pro Ser Asp Asp Thr Lys Gly Phe Phe Asp
    2810                2815                2820

Pro Asn Thr His Glu Asn Leu Thr Tyr Leu Gln Leu Leu Glu Arg
    2825                2830                2835

Cys Val Glu Asp Pro Glu Thr Gly Leu Cys Leu Leu Pro Leu Thr
    2840                2845                2850

Asp Lys Ala Ala Lys Gly Gly Glu Leu Val Tyr Thr Asp Ser Glu
    2855                2860                2865

Ala Arg Asp Val Phe Glu Lys Ala Thr Val Ser Ala Pro Phe Gly
    2870                2875                2880

Lys Phe Gln Gly Lys Thr Val Thr Ile Trp Glu Ile Ile Asn Ser
    2885                2890                2895

Glu Tyr Phe Thr Ala Glu Gln Arg Arg Asp Leu Leu Arg Gln Phe
    2900                2905                2910

Arg Thr Gly Arg Ile Thr Val Glu Lys Ile Ile Lys Ile Ile Ile
    2915                2920                2925
```

```
Thr Val Val Glu Glu Gln Glu Gln Lys Gly Arg Leu Cys Phe Glu
2930            2935                2940

Gly Leu Arg Ser Leu Val Pro Ala Ala Glu Leu Leu Glu Ser Arg
2945            2950                2955

Val Ile Asp Arg Glu Leu Tyr Gln Gln Leu Gln Arg Gly Glu Arg
2960            2965                2970

Ser Val Arg Asp Val Ala Glu Val Asp Thr Val Arg Arg Ala Leu
2975            2980                2985

Arg Gly Ala Asn Val Ile Ala Gly Val Trp Leu Glu Glu Ala Gly
2990            2995                3000

Gln Lys Leu Ser Ile Tyr Asn Ala Leu Lys Lys Asp Leu Leu Pro
3005            3010                3015

Ser Asp Met Ala Val Ala Leu Leu Glu Ala Gln Ala Gly Thr Gly
3020            3025                3030

His Ile Ile Asp Pro Ala Thr Ser Ala Arg Leu Thr Val Asp Glu
3035            3040                3045

Ala Val Arg Ala Gly Leu Val Gly Pro Glu Phe His Glu Lys Leu
3050            3055                3060

Leu Ser Ala Glu Lys Ala Val Thr Gly Tyr Arg Asp Pro Tyr Thr
3065            3070                3075

Gly Gln Ser Val Ser Leu Phe Gln Ala Leu Lys Lys Gly Leu Ile
3080            3085                3090

Pro Arg Glu Gln Gly Leu Arg Leu Leu Asp Ala Gln Leu Ser Thr
3095            3100                3105

Gly Gly Ile Val Asp Pro Ser Lys Ser His Arg Val Pro Leu Asp
3110            3115                3120

Val Ala Cys Ala Arg Gly Cys Leu Asp Glu Glu Thr Ser Arg Ala
3125            3130                3135

Leu Ser Ala Pro Arg Ala Asp Ala Lys Ala Tyr Ser Asp Pro Ser
3140            3145                3150

Thr Gly Glu Pro Ala Thr Tyr Gly Glu Leu Gln Gln Arg Cys Arg
3155            3160                3165

Pro Asp Gln Leu Thr Gly Leu Ser Leu Leu Pro Leu Ser Glu Lys
3170            3175                3180

Ala Ala Arg Ala Arg Gln Glu Glu Leu Tyr Ser Glu Leu Gln Ala
3185            3190                3195

Arg Glu Thr Phe Glu Lys Thr Pro Val Glu Val Pro Val Gly Gly
3200            3205                3210

Phe Lys Gly Arg Thr Val Thr Val Trp Glu Leu Ile Ser Ser Glu
3215            3220                3225

Tyr Phe Thr Ala Glu Gln Arg Gln Glu Leu Leu Arg Gln Phe Arg
3230            3235                3240

Thr Gly Lys Val Thr Val Glu Lys Val Ile Lys Ile Leu Ile Thr
3245            3250                3255

Ile Val Glu Glu Val Glu Thr Leu Arg Gln Glu Arg Leu Ser Phe
3260            3265                3270

Ser Gly Leu Arg Ala Pro Val Pro Ala Ser Glu Leu Leu Ala Ser
3275            3280                3285

Gly Val Leu Ser Arg Ala Gln Phe Glu Gln Leu Lys Asp Gly Lys
3290            3295                3300

Thr Thr Val Lys Asp Leu Ser Glu Leu Gly Ser Val Arg Thr Leu
3305            3310                3315

Leu Gln Gly Ser Gly Cys Leu Ala Gly Ile Tyr Leu Glu Asp Thr
```

-continued

```
            3320                  3325                  3330
Lys Glu Lys Val Ser Ile Tyr Glu Ala Met Arg Arg Gly Leu Leu
            3335                  3340                  3345
Arg Ala Thr Thr Ala Ala Leu Leu Leu Glu Ala Gln Ala Ala Thr
            3350                  3355                  3360
Gly Phe Leu Val Asp Pro Val Arg Asn Gln Arg Leu Tyr Val His
            3365                  3370                  3375
Glu Ala Val Lys Ala Gly Val Val Gly Pro Glu Leu His Glu Gln
            3380                  3385                  3390
Leu Leu Ser Ala Glu Lys Ala Val Thr Gly Tyr Arg Asp Pro Tyr
            3395                  3400                  3405
Ser Gly Ser Thr Ile Ser Leu Phe Gln Ala Met Gln Lys Gly Leu
            3410                  3415                  3420
Val Leu Arg Gln His Gly Ile Arg Leu Leu Glu Ala Gln Ile Ala
            3425                  3430                  3435
Thr Gly Gly Ile Ile Asp Pro Val His Ser His Arg Val Pro Val
            3440                  3445                  3450
Asp Val Ala Tyr Gln Arg Gly Tyr Phe Ser Glu Glu Met Asn Arg
            3455                  3460                  3465
Val Leu Ala Asp Pro Ser Asp Asp Thr Lys Gly Phe Phe Asp Pro
            3470                  3475                  3480
Asn Thr His Glu Asn Leu Thr Tyr Arg Gln Leu Leu Glu Arg Cys
            3485                  3490                  3495
Val Glu Asp Pro Glu Thr Gly Leu Arg Leu Leu Pro Leu Lys Gly
            3500                  3505                  3510
Ala Glu Lys Ala Glu Val Val Glu Thr Thr Gln Val Tyr Thr Glu
            3515                  3520                  3525
Glu Glu Thr Arg Arg Ala Phe Glu Glu Thr Gln Ile Asp Ile Pro
            3530                  3535                  3540
Gly Gly Gly Ser His Gly Gly Ser Thr Met Ser Leu Trp Glu Val
            3545                  3550                  3555
Met Gln Ser Asp Leu Ile Pro Glu Glu Gln Arg Ala Gln Leu Met
            3560                  3565                  3570
Ala Asp Phe Gln Ala Gly Arg Val Thr Lys Glu Arg Met Ile Ile
            3575                  3580                  3585
Ile Ile Ile Glu Ile Ile Glu Lys Thr Glu Ile Ile Arg Gln Gln
            3590                  3595                  3600
Gly Leu Ala Ser Tyr Asp Tyr Val Arg Arg Leu Thr Ala Glu
            3605                  3610                  3615
Asp Leu Phe Glu Ala Arg Ile Ile Ser Leu Glu Thr Tyr Asn Leu
            3620                  3625                  3630
Leu Arg Glu Gly Thr Arg Ser Leu Arg Glu Ala Leu Glu Ala Glu
            3635                  3640                  3645
Ser Ala Trp Cys Tyr Leu Tyr Gly Thr Gly Ser Val Ala Gly Val
            3650                  3655                  3660
Tyr Leu Pro Gly Ser Arg Gln Thr Leu Ser Ile Tyr Gln Ala Leu
            3665                  3670                  3675
Lys Lys Gly Leu Leu Ser Ala Glu Val Ala Arg Leu Leu Leu Glu
            3680                  3685                  3690
Ala Gln Ala Ala Thr Gly Phe Leu Leu Asp Pro Val Lys Gly Glu
            3695                  3700                  3705
Arg Leu Thr Val Asp Glu Ala Val Arg Lys Gly Leu Val Gly Pro
            3710                  3715                  3720
```

-continued

Glu Leu His Asp Arg Leu Leu Ser Ala Glu Arg Ala Val Thr Gly
3725                3730                3735

Tyr Arg Asp Pro Tyr Thr Glu Gln Thr Ile Ser Leu Phe Gln Ala
3740                3745                3750

Met Lys Lys Glu Leu Ile Pro Thr Glu Glu Ala Leu Arg Leu Leu
3755                3760                3765

Asp Ala Gln Leu Ala Thr Gly Gly Ile Val Asp Pro Arg Leu Gly
3770                3775                3780

Phe His Leu Pro Leu Glu Val Ala Tyr Gln Arg Gly Tyr Leu Asn
3785                3790                3795

Lys Asp Thr His Asp Gln Leu Ser Glu Pro Ser Glu Val Arg Ser
3800                3805                3810

Tyr Val Asp Pro Ser Thr Asp Glu Arg Leu Ser Tyr Thr Gln Leu
3815                3820                3825

Leu Arg Arg Cys Arg Arg Asp Asp Gly Thr Gly Gln Leu Leu Leu
3830                3835                3840

Pro Leu Ser Asp Ala Arg Lys Leu Thr Phe Arg Gly Leu Arg Lys
3845                3850                3855

Gln Ile Thr Met Glu Glu Leu Val Arg Ser Gln Val Met Asp Glu
3860                3865                3870

Ala Thr Ala Leu Gln Leu Arg Glu Gly Leu Thr Ser Ile Glu Glu
3875                3880                3885

Val Thr Lys Asn Leu Gln Lys Phe Leu Glu Gly Thr Ser Cys Ile
3890                3895                3900

Ala Gly Val Phe Val Asp Ala Thr Lys Glu Arg Leu Ser Val Tyr
3905                3910                3915

Gln Ala Met Lys Lys Gly Ile Ile Arg Pro Gly Thr Ala Phe Glu
3920                3925                3930

Leu Leu Glu Ala Gln Ala Ala Thr Gly Tyr Val Ile Asp Pro Ile
3935                3940                3945

Lys Gly Leu Lys Leu Thr Val Glu Glu Ala Val Arg Met Gly Ile
3950                3955                3960

Val Gly Pro Glu Phe Lys Asp Lys Leu Leu Ser Ala Glu Arg Ala
3965                3970                3975

Val Thr Gly Tyr Lys Asp Pro Tyr Ser Gly Lys Leu Ile Ser Leu
3980                3985                3990

Phe Gln Ala Met Lys Lys Gly Leu Ile Leu Lys Asp His Gly Ile
3995                4000                4005

Arg Leu Leu Glu Ala Gln Ile Ala Thr Gly Gly Ile Ile Asp Pro
4010                4015                4020

Glu Glu Ser His Arg Leu Pro Val Glu Val Ala Tyr Lys Arg Gly
4025                4030                4035

Leu Phe Asp Glu Glu Met Asn Glu Ile Leu Thr Asp Pro Ser Asp
4040                4045                4050

Asp Thr Lys Gly Phe Phe Asp Pro Asn Thr Glu Glu Asn Leu Thr
4055                4060                4065

Tyr Leu Gln Leu Met Glu Arg Cys Ile Thr Asp Pro Gln Thr Gly
4070                4075                4080

Leu Cys Leu Leu Pro Leu Lys Glu Lys Lys Arg Glu Arg Lys Thr
4085                4090                4095

Ser Ser Lys Ser Ser Val Arg Lys Arg Arg Val Val Ile Val Asp
4100                4105                4110

```
Pro Glu Thr Gly Lys Glu Met Ser Val Tyr Glu Ala Tyr Arg Lys
4115                4120                4125

Gly Leu Ile Asp His Gln Thr Tyr Leu Glu Leu Ser Glu Gln Glu
4130                4135                4140

Cys Glu Trp Glu Glu Ile Thr Ile Ser Ser Ser Asp Gly Val Val
4145                4150                4155

Lys Ser Met Ile Ile Asp Arg Arg Ser Gly Arg Gln Tyr Asp Ile
4160                4165                4170

Asp Asp Ala Ile Ala Lys Asn Leu Ile Asp Arg Ser Ala Leu Asp
4175                4180                4185

Gln Tyr Arg Ala Gly Thr Leu Ser Ile Thr Glu Phe Ala Asp Met
4190                4195                4200

Leu Ser Gly Asn Ala Gly Gly Phe Arg Ser Arg Ser Ser Ser Val
4205                4210                4215

Gly Ser Ser Ser Ser Tyr Pro Ile Ser Pro Ala Val Ser Arg Thr
4220                4225                4230

Gln Leu Ala Ser Trp Ser Asp Pro Thr Glu Glu Thr Gly Pro Val
4235                4240                4245

Ala Gly Ile Leu Asp Thr Glu Thr Leu Glu Lys Val Ser Ile Thr
4250                4255                4260

Glu Ala Met His Arg Asn Leu Val Asp Asn Ile Thr Gly Gln Arg
4265                4270                4275

Leu Leu Glu Ala Gln Ala Cys Thr Gly Gly Ile Ile Asp Pro Ser
4280                4285                4290

Thr Gly Glu Arg Phe Pro Val Thr Asp Ala Val Asn Lys Gly Leu
4295                4300                4305

Val Asp Lys Ile Met Val Asp Arg Ile Asn Leu Ala Gln Lys Ala
4310                4315                4320

Phe Cys Gly Phe Glu Asp Pro Arg Thr Lys Thr Lys Met Ser Ala
4325                4330                4335

Ala Gln Ala Leu Lys Lys Gly Trp Leu Tyr Tyr Glu Ala Gly Gln
4340                4345                4350

Arg Phe Leu Glu Val Gln Tyr Leu Thr Gly Gly Leu Ile Glu Pro
4355                4360                4365

Asp Thr Pro Gly Arg Val Pro Leu Asp Glu Ala Leu Gln Arg Gly
4370                4375                4380

Thr Val Asp Ala Arg Thr Ala Gln Lys Leu Arg Asp Val Gly Ala
4385                4390                4395

Tyr Ser Lys Tyr Leu Thr Cys Pro Lys Thr Lys Leu Lys Ile Ser
4400                4405                4410

Tyr Lys Asp Ala Leu Asp Arg Ser Met Val Glu Glu Gly Thr Gly
4415                4420                4425

Leu Arg Leu Leu Glu Ala Ala Ala Gln Ser Thr Lys Gly Tyr Tyr
4430                4435                4440

Ser Pro Tyr Ser Val Ser Gly Ser Gly Ser Thr Ala Gly Ser Arg
4445                4450                4455

Thr Gly Ser Arg Thr Gly Ser Arg Ala Gly Ser Arg Arg Gly Ser
4460                4465                4470

Phe Asp Ala Thr Gly Ser Gly Phe Ser Met Thr Phe Ser Ser Ser
4475                4480                4485

Ser Tyr Ser Ser Ser Gly Tyr Gly Arg Arg Tyr Ala Ser Gly Ser
4490                4495                4500

Ser Ala Ser Leu Gly Gly Pro Glu Ser Ala Val Ala
```

<210> SEQ ID NO 39
<211> LENGTH: 248
<212> TYPE: PRT
<213> ORGANISM: homo sapiens

<400> SEQUENCE: 39

Met Ser Ser Ile Gly Thr Gly Tyr Asp Leu Ser Ala Ser Thr Phe Ser
1               5                   10                  15

Pro Asp Gly Arg Val Phe Gln Val Glu Tyr Ala Met Lys Ala Val Glu
            20                  25                  30

Asn Ser Ser Thr Ala Ile Gly Ile Arg Cys Lys Asp Gly Val Val Phe
        35                  40                  45

Gly Val Glu Lys Leu Val Leu Ser Lys Leu Tyr Glu Glu Gly Ser Asn
50                  55                  60

Lys Arg Leu Phe Asn Val Asp Arg His Val Gly Met Ala Val Ala Gly
65                  70                  75                  80

Leu Leu Ala Asp Ala Arg Ser Leu Ala Asp Ile Ala Arg Glu Glu Ala
                85                  90                  95

Ser Asn Phe Arg Ser Asn Phe Gly Tyr Asn Ile Pro Leu Lys His Leu
            100                 105                 110

Ala Asp Arg Val Ala Met Tyr Val His Ala Tyr Thr Leu Tyr Ser Ala
        115                 120                 125

Val Arg Pro Phe Gly Cys Ser Val Asn Asp Gly Ala Gln Leu Tyr Met
130                 135                 140

Ile Asp Pro Ser Gly Val Ser Tyr Gly Tyr Trp Gly Cys Ala Ile Gly
145                 150                 155                 160

Lys Ala Arg Gln Ala Ala Lys Thr Glu Ile Glu Lys Leu Gln Met Lys
                165                 170                 175

Glu Met Thr Cys Arg Asp Ile Val Lys Glu Val Ala Lys Ile Ile Tyr
            180                 185                 190

Ile Val His Asp Glu Val Lys Asp Lys Ala Phe Glu Leu Glu Leu Ser
        195                 200                 205

Trp Val Gly Glu Leu Thr Asn Gly Arg His Glu Ile Val Pro Lys Asp
210                 215                 220

Ile Arg Glu Glu Ala Glu Lys Tyr Ala Lys Glu Ser Leu Lys Glu Glu
225                 230                 235                 240

Asp Glu Ser Asp Asp Asp Asn Met
                245

<210> SEQ ID NO 40
<211> LENGTH: 398
<212> TYPE: PRT
<213> ORGANISM: homo sapiens

<400> SEQUENCE: 40

Met Glu Leu Glu Glu Gly Lys Ala Gly Ser Gly Leu Arg Gln Tyr Tyr
1               5                   10                  15

Leu Ser Lys Ile Glu Glu Leu Gln Leu Ile Val Asn Asp Lys Ser Gln
            20                  25                  30

Asn Leu Arg Arg Leu Gln Ala Gln Arg Asn Glu Leu Asn Ala Lys Val
        35                  40                  45

Arg Leu Leu Arg Glu Glu Leu Gln Leu Gln Glu Gln Gly Ser Tyr
50                  55                  60

Val Gly Glu Val Val Arg Ala Met Asp Lys Lys Lys Val Leu Val Lys

Val His Pro Glu Gly Lys Phe Val Val Asp Val Asp Lys Asn Ile Asp
            85                  90                  95

Ile Asn Asp Val Thr Pro Asn Cys Arg Val Ala Leu Arg Asn Asp Ser
            100                 105                 110

Tyr Thr Leu His Lys Ile Leu Pro Asn Lys Val Asp Pro Leu Val Ser
            115                 120                 125

Leu Met Met Val Glu Lys Val Pro Asp Ser Thr Tyr Glu Met Ile Gly
        130                 135                 140

Gly Leu Asp Lys Gln Ile Lys Glu Ile Lys Glu Val Ile Glu Leu Pro
145                 150                 155                 160

Val Lys His Pro Glu Leu Phe Glu Ala Leu Gly Ile Ala Gln Pro Lys
                165                 170                 175

Gly Val Leu Leu Tyr Gly Pro Pro Gly Thr Gly Lys Thr Leu Leu Ala
            180                 185                 190

Arg Ala Val Ala His His Thr Asp Cys Thr Phe Ile Arg Val Ser Gly
            195                 200                 205

Ser Glu Leu Val Gln Lys Phe Ile Gly Glu Gly Ala Arg Met Val Arg
210                 215                 220

Glu Leu Phe Val Met Ala Arg Glu His Ala Pro Ser Ile Ile Phe Met
225                 230                 235                 240

Asp Glu Ile Asp Ser Ile Gly Ser Ser Arg Leu Glu Gly Gly Ser Gly
            245                 250                 255

Gly Asp Ser Glu Val Gln Arg Thr Met Leu Glu Leu Leu Asn Gln Leu
            260                 265                 270

Asp Gly Phe Glu Ala Thr Lys Asn Ile Lys Val Ile Met Ala Thr Asn
        275                 280                 285

Arg Ile Asp Ile Leu Asp Ser Ala Leu Leu Arg Pro Gly Arg Ile Asp
        290                 295                 300

Arg Lys Ile Glu Phe Pro Pro Pro Asn Glu Glu Ala Arg Leu Asp Ile
305                 310                 315                 320

Leu Lys Ile His Ser Arg Lys Met Asn Leu Thr Arg Gly Ile Asn Leu
            325                 330                 335

Arg Lys Ile Ala Glu Leu Met Pro Gly Ala Ser Gly Ala Glu Val Lys
            340                 345                 350

Gly Val Cys Thr Glu Ala Gly Met Tyr Ala Leu Arg Glu Arg Arg Val
            355                 360                 365

His Val Thr Gln Glu Asp Phe Glu Met Ala Val Ala Lys Val Met Gln
        370                 375                 380

Lys Asp Ser Glu Lys Asn Met Ser Ile Lys Lys Leu Trp Lys
385                 390                 395

<210> SEQ ID NO 41
<211> LENGTH: 390
<212> TYPE: PRT
<213> ORGANISM: homo sapiens

<400> SEQUENCE: 41

Met Glu Asp Pro Thr Leu Tyr Ile Val Glu Arg Pro Leu Pro Gly Tyr
1               5                   10                  15

Pro Asp Ala Glu Ala Pro Glu Pro Ser Ser Ala Gly Ala Gln Ala Ala
            20                  25                  30

Glu Glu Pro Ser Gly Ala Gly Ser Glu Glu Leu Ile Lys Ser Asp Gln
        35                  40                  45

```
Val Asn Gly Val Leu Val Leu Ser Leu Leu Asp Lys Ile Ile Gly Ala
     50                  55                  60

Val Asp Gln Ile Gln Leu Thr Gln Ala Gln Leu Glu Glu Arg Gln Ala
 65                  70                  75                  80

Glu Met Glu Gly Ala Val Gln Ser Ile Gln Gly Glu Leu Ser Lys Leu
                 85                  90                  95

Gly Lys Ala His Ala Thr Thr Ser Asn Thr Val Ser Lys Leu Leu Glu
            100                 105                 110

Lys Val Arg Lys Val Ser Val Asn Val Lys Thr Val Arg Gly Ser Leu
            115                 120                 125

Glu Arg Gln Ala Gly Gln Ile Lys Lys Leu Glu Val Asn Glu Ala Glu
130                 135                 140

Leu Leu Arg Arg Arg Asn Phe Lys Val Met Ile Tyr Gln Asp Glu Val
145                 150                 155                 160

Lys Leu Pro Ala Lys Leu Ser Ile Ser Lys Ser Leu Lys Glu Ser Glu
                165                 170                 175

Ala Leu Pro Glu Lys Glu Gly Glu Glu Leu Gly Glu Gly Glu Arg Pro
            180                 185                 190

Glu Glu Asp Ala Ala Ala Leu Glu Leu Ser Ser Asp Glu Ala Val Glu
            195                 200                 205

Val Glu Glu Val Ile Glu Glu Ser Arg Ala Glu Arg Ile Lys Arg Ser
210                 215                 220

Gly Leu Arg Arg Val Asp Asp Phe Lys Lys Ala Phe Ser Lys Glu Lys
225                 230                 235                 240

Met Glu Lys Thr Lys Val Arg Thr Arg Glu Asn Leu Glu Lys Thr Arg
                245                 250                 255

Leu Lys Thr Lys Glu Asn Leu Glu Lys Thr Arg His Thr Leu Glu Lys
            260                 265                 270

Arg Met Asn Lys Leu Gly Thr Arg Leu Val Pro Ala Glu Arg Arg Glu
            275                 280                 285

Lys Leu Lys Thr Ser Arg Asp Lys Leu Arg Lys Ser Phe Thr Pro Asp
290                 295                 300

His Val Val Tyr Ala Arg Ser Lys Thr Ala Val Tyr Lys Val Pro Pro
305                 310                 315                 320

Phe Thr Phe His Val Lys Lys Ile Arg Glu Gly Gln Val Glu Val Leu
                325                 330                 335

Lys Ala Thr Glu Met Val Glu Val Gly Ala Asp Asp Glu Gly Gly
            340                 345                 350

Ala Glu Arg Gly Glu Ala Gly Asp Leu Arg Arg Gly Ser Ser Pro Asp
            355                 360                 365

Val His Ala Leu Leu Glu Ile Thr Glu Glu Ser Asp Ala Val Leu Val
370                 375                 380

Asp Lys Ser Asp Ser Asp
385                 390

<210> SEQ ID NO 42
<211> LENGTH: 207
<212> TYPE: PRT
<213> ORGANISM: homo sapiens

<400> SEQUENCE: 42

Met Thr Ser Arg Lys Lys Val Leu Leu Lys Val Ile Ile Leu Gly Asp
 1               5                  10                  15

Ser Gly Val Gly Lys Thr Ser Leu Met Asn Gln Tyr Val Asn Lys Lys
                 20                  25                  30
```

-continued

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
 50                  55                  60

Ala Gly Gln Glu Arg Phe Gln Ser Leu Gly Val Ala Phe Tyr Arg Gly
 65                  70                  75                  80

Ala Asp Cys Cys Val Leu Val Phe Asp Val Thr Ala Pro Asn Thr Phe
                 85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
            115                 120                 125

Leu Glu Asn Arg Gln Val Ala Thr Lys Arg Ala Gln Ala Trp Cys Tyr
        130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
            180                 185                 190

Asp Lys Asn Asp Arg Ala Lys Ala Ser Ala Glu Ser Cys Ser Cys
            195                 200                 205

<210> SEQ ID NO 43
<211> LENGTH: 216
<212> TYPE: PRT
<213> ORGANISM: homo sapiens

<400> SEQUENCE: 43

Met Gly Arg Arg Pro Ala Arg Cys Tyr Arg Tyr Cys Lys Asn Lys Pro
 1                   5                  10                  15

Tyr Pro Lys Ser Arg Phe Cys Arg Gly Val Pro Asp Ala Lys Ile Arg
             20                  25                  30

Ile Phe Asp Leu Gly Arg Lys Lys Ala Lys Val Asp Glu Phe Pro Leu
         35                  40                  45

Cys Gly His Met Val Ser Asp Glu Tyr Glu Gln Leu Ser Ser Glu Ala
 50                  55                  60

Leu Glu Ala Ala Arg Ile Cys Ala Asn Lys Tyr Met Val Lys Ser Cys
 65                  70                  75                  80

Gly Lys Asp Gly Phe His Ile Arg Val Arg Leu His Pro Phe His Val
                 85                  90                  95

Ile Arg Ile Asn Lys Met Leu Ser Cys Ala Gly Ala Asp Arg Ser Thr
            100                 105                 110

Ser Gln Arg Ser Gly Ala Ser Pro Ser Ser Met Leu Met Asn Leu Lys
        115                 120                 125

Thr Trp Trp Leu Lys Ser Gly Ser Gln Met Ala Val Gly Ser Ser
        130                 135                 140

Thr Ser Pro Val Val Ala Leu Trp Thr Ser Gly Pro Cys Thr His
145                 150                 155                 160

Glu Gly Phe Gln Cys Ala Ala Pro Leu Leu Ile Leu Thr Asn Lys Phe
                165                 170                 175

Tyr Phe Leu Ser Thr Tyr Val Phe Val Ser Thr Phe Leu Thr Gly Lys
            180                 185                 190

Glu Leu Pro Leu Gly Thr Phe Gly Ser Leu Pro Phe His Phe Arg Asn

```
                    195                 200                 205
Arg Leu Thr Thr Gln Pro Cys Ser
    210                 215

<210> SEQ ID NO 44
<211> LENGTH: 977
<212> TYPE: PRT
<213> ORGANISM: homo sapiens

<400> SEQUENCE: 44

Met Asp Ile Tyr Asp Thr Gln Thr Leu Gly Val Val Phe Gly Gly
1               5                   10                  15

Phe Met Val Val Ser Ala Ile Gly Ile Phe Leu Val Ser Thr Phe Ser
            20                  25                  30

Met Lys Glu Thr Ser Tyr Glu Glu Ala Leu Ala Asn Gln Arg Lys Glu
        35                  40                  45

Met Ala Lys Thr His His Gln Lys Val Glu Lys Lys Lys Glu Lys
    50                  55                  60

Thr Val Glu Lys Lys Gly Lys Thr Lys Lys Glu Glu Lys Pro Asn
65                  70                  75                  80

Gly Lys Ile Pro Asp His Asp Pro Ala Pro Asn Val Thr Val Leu Leu
                85                  90                  95

Arg Glu Pro Val Arg Ala Pro Ala Val Ala Val Ala Pro Thr Pro Val
            100                 105                 110

Gln Pro Pro Ile Ile Val Ala Pro Val Ala Thr Val Pro Ala Met Pro
        115                 120                 125

Gln Glu Lys Leu Ala Ser Ser Pro Lys Asp Lys Lys Lys Glu Lys
    130                 135                 140

Lys Val Ala Lys Val Glu Pro Ala Val Ser Ser Val Val Asn Ser Ile
145                 150                 155                 160

Gln Val Leu Thr Ser Lys Ala Ala Ile Leu Glu Thr Ala Pro Lys Glu
                165                 170                 175

Gly Arg Asn Thr Asp Val Ala Gln Ser Pro Glu Ala Pro Lys Gln Glu
            180                 185                 190

Ala Pro Ala Lys Lys Lys Ser Gly Ser Lys Lys Lys Gly Pro Pro Asp
        195                 200                 205

Ala Asp Gly Pro Leu Tyr Leu Pro Tyr Lys Thr Leu Val Ser Thr Val
    210                 215                 220

Gly Ser Met Val Phe Asn Glu Gly Glu Ala Gln Arg Leu Ile Glu Ile
225                 230                 235                 240

Leu Ser Glu Lys Ala Gly Ile Ile Gln Asp Thr Trp His Lys Ala Thr
                245                 250                 255

Gln Lys Gly Asp Pro Val Ala Ile Leu Lys Arg Gln Leu Glu Glu Lys
            260                 265                 270

Glu Lys Leu Leu Ala Thr Glu Gln Gly Asp Ala Ala Val Ala Lys Ser
        275                 280                 285

Lys Leu Arg Glu Leu Asn Lys Glu Met Ala Ala Glu Lys Ala Lys Ala
    290                 295                 300

Ala Ala Gly Glu Ala Lys Val Lys Lys Gln Leu Val Ala Arg Glu Gln
305                 310                 315                 320

Glu Ile Thr Ala Val Gln Ala Arg Met Gln Ala Ser Tyr Arg Glu His
                325                 330                 335

Val Lys Glu Val Gln Gln Leu Gln Gly Lys Ile Arg Thr Leu Gln Glu
            340                 345                 350
```

```
Gln Leu Glu Asn Gly Pro Asn Thr Gln Leu Ala Arg Leu Gln Gln Glu
            355                 360                 365
Asn Ser Ile Leu Arg Asp Ala Leu Asn Gln Ala Thr Ser Gln Val Glu
        370                 375                 380
Ser Lys Gln Asn Ala Glu Leu Ala Lys Leu Arg Gln Glu Leu Ser Lys
385                 390                 395                 400
Val Ser Lys Glu Leu Val Lys Ser Glu Ala Val Arg Gln Asp Glu
            405                 410                 415
Gln Gln Arg Lys Ala Leu Glu Ala Ala Ala Phe Glu Lys Gln
            420                 425                 430
Val Leu Gln Leu Gln Ala Ser His Arg Glu Ser Glu Glu Ala Leu Gln
            435                 440                 445
Lys Arg Leu Asp Glu Val Ser Arg Glu Leu Cys His Thr Gln Ser Ser
        450                 455                 460
His Ala Ser Leu Arg Ala Asp Ala Glu Lys Ala Gln Glu Gln Gln Gln
465                 470                 475                 480
Gln Met Ala Glu Leu His Ser Lys Leu Gln Ser Ser Glu Ala Glu Val
            485                 490                 495
Arg Ser Lys Cys Glu Glu Leu Ser Gly Leu His Gly Gln Leu Gln Glu
            500                 505                 510
Ala Arg Ala Glu Asn Ser Gln Leu Thr Glu Arg Ile Arg Ser Ile Glu
            515                 520                 525
Ala Leu Leu Glu Ala Gly Gln Ala Arg Asp Ala Gln Asp Val Gln Ala
            530                 535                 540
Ser Gln Ala Glu Ala Asp Gln Gln Thr Arg Leu Lys Glu Leu Glu
545                 550                 555                 560
Ser Gln Val Ser Gly Leu Glu Lys Glu Ala Ile Glu Leu Arg Glu Ala
            565                 570                 575
Val Glu Gln Gln Lys Val Lys Asn Asn Asp Leu Arg Glu Lys Asn Trp
            580                 585                 590
Lys Ala Met Glu Ala Leu Ala Thr Ala Glu Gln Ala Cys Lys Glu Lys
            595                 600                 605
Leu His Ser Leu Thr Gln Ala Lys Glu Glu Ser Glu Lys Gln Leu Cys
        610                 615                 620
Leu Ile Glu Ala Gln Thr Met Glu Ala Leu Leu Ala Leu Pro Glu
625                 630                 635                 640
Leu Ser Val Leu Ala Gln Gln Asn Tyr Thr Glu Trp Leu Gln Asp Leu
            645                 650                 655
Lys Glu Lys Gly Pro Thr Leu Leu Lys His Pro Pro Ala Pro Ala Glu
            660                 665                 670
Pro Ser Ser Asp Leu Ala Ser Lys Leu Arg Glu Ala Glu Glu Thr Gln
            675                 680                 685
Ser Thr Leu Gln Ala Glu Cys Asp Gln Tyr Arg Ser Ile Leu Ala Glu
        690                 695                 700
Thr Glu Gly Met Leu Arg Asp Leu Gln Lys Ser Val Glu Glu Glu
705                 710                 715                 720
Gln Val Trp Arg Ala Lys Val Gly Ala Glu Glu Leu Gln Lys
            725                 730                 735
Ser Arg Val Thr Val Lys His Leu Glu Ile Val Glu Lys Leu Lys
            740                 745                 750
Gly Glu Leu Glu Ser Ser Asp Gln Val Arg Glu His Thr Ser His Leu
            755                 760                 765
Glu Ala Glu Leu Glu Lys His Met Ala Ala Ala Ser Ala Glu Cys Gln
```

```
              770                 775                 780
Asn Tyr Ala Lys Glu Val Ala Gly Leu Arg Gln Leu Leu Glu Ser
785                 790                 795                 800

Gln Ser Gln Leu Asp Ala Ala Lys Ser Glu Ala Gln Lys Gln Ser Asp
                805                 810                 815

Glu Leu Ala Leu Val Arg Gln Gln Leu Ser Glu Met Lys Ser His Val
                820                 825                 830

Glu Asp Gly Asp Ile Ala Gly Ala Pro Ala Ser Ser Pro Glu Ala Pro
                835                 840                 845

Pro Ala Glu Gln Asp Pro Val Gln Leu Lys Thr Gln Leu Glu Trp Thr
850                 855                 860

Glu Ala Ile Leu Glu Asp Glu Gln Thr Gln Arg Gln Lys Leu Thr Ala
865                 870                 875                 880

Glu Phe Glu Glu Ala Gln Thr Ser Ala Cys Arg Leu Gln Glu Glu Leu
                885                 890                 895

Glu Lys Leu Arg Thr Ala Gly Pro Leu Glu Ser Ser Glu Thr Glu Glu
                900                 905                 910

Ala Ser Gln Leu Lys Glu Arg Leu Glu Lys Glu Lys Lys Leu Thr Ser
                915                 920                 925

Asp Leu Gly Arg Ala Ala Thr Arg Leu Gln Glu Leu Leu Lys Thr Thr
                930                 935                 940

Gln Glu Gln Leu Ala Arg Glu Lys Asp Thr Val Lys Lys Leu Gln Glu
945                 950                 955                 960

Gln Leu Glu Lys Ala Glu Asp Gly Ser Ser Lys Glu Gly Thr Ser
                965                 970                 975

Val

<210> SEQ ID NO 45
<211> LENGTH: 437
<212> TYPE: PRT
<213> ORGANISM: homo sapiens

<400> SEQUENCE: 45

Met Ser Val Ser Ala Arg Ser Ala Ala Glu Glu Arg Ser Val Asn
1               5                   10                  15

Ser Ser Thr Met Val Ala Gln Gln Lys Asn Leu Glu Gly Tyr Val Gly
                20                  25                  30

Phe Ala Asn Leu Pro Asn Gln Val Tyr Arg Lys Ser Val Lys Arg Gly
                35                  40                  45

Phe Glu Phe Thr Leu Met Val Val Gly Glu Ser Gly Leu Gly Lys Ser
50                  55                  60

Thr Leu Ile Asn Ser Leu Phe Leu Thr Asp Leu Tyr Ser Pro Glu Tyr
65                  70                  75                  80

Pro Gly Pro Ser His Arg Ile Lys Lys Thr Val Gln Val Glu Gln Ser
                85                  90                  95

Lys Val Leu Ile Lys Glu Gly Gly Val Gln Leu Leu Thr Ile Val
                100                 105                 110

Asp Thr Pro Gly Phe Gly Asp Ala Val Asp Asn Ser Asn Cys Trp Gln
                115                 120                 125

Pro Val Ile Asp Tyr Ile Asp Ser Lys Phe Glu Asp Tyr Leu Asn Ala
                130                 135                 140

Glu Ser Arg Val Asn Arg Arg Gln Met Pro Asp Asn Arg Val Gln Cys
145                 150                 155                 160

Cys Leu Tyr Phe Ile Ala Pro Ser Gly His Gly Leu Lys Pro Leu Asp
```

-continued

```
                165                 170                 175
Ile Glu Phe Met Lys Arg Leu His Glu Lys Val Asn Ile Ile Pro Leu
                180                 185                 190

Ile Ala Lys Ala Asp Thr Leu Thr Pro Glu Glu Cys Gln Gln Phe Lys
        195                 200                 205

Lys Gln Ile Met Lys Glu Ile Gln Glu His Lys Ile Lys Ile Tyr Glu
    210                 215                 220

Phe Pro Glu Thr Asp Asp Glu Glu Asn Lys Leu Val Lys Lys Ile
225                 230                 235                 240

Lys Asp Arg Leu Pro Leu Ala Val Val Gly Ser Asn Thr Ile Ile Glu
                245                 250                 255

Val Asn Gly Lys Arg Val Arg Gly Arg Gln Tyr Pro Trp Gly Val Ala
                260                 265                 270

Glu Val Glu Asn Gly Glu His Cys Asp Phe Thr Ile Leu Arg Asn Met
            275                 280                 285

Leu Ile Arg Thr His Met Gln Asp Leu Lys Asp Val Thr Asn Asn Val
        290                 295                 300

His Tyr Glu Asn Tyr Arg Ser Arg Lys Leu Ala Ala Val Thr Tyr Asn
305                 310                 315                 320

Gly Val Asp Asn Asn Lys Asn Lys Gly Gln Leu Thr Lys Ser Pro Leu
                325                 330                 335

Ala Gln Met Glu Glu Arg Arg Glu His Val Ala Lys Met Lys Lys
            340                 345                 350

Met Glu Met Glu Met Glu Gln Val Phe Glu Met Lys Val Lys Glu Lys
        355                 360                 365

Val Gln Lys Leu Lys Asp Ser Glu Ala Glu Leu Gln Arg Arg His Glu
    370                 375                 380

Gln Met Lys Lys Asn Leu Glu Ala Gln His Lys Glu Leu Glu Glu Lys
385                 390                 395                 400

Arg Arg Gln Phe Glu Asp Glu Lys Ala Asn Trp Glu Ala Gln Gln Arg
                405                 410                 415

Ile Leu Glu Gln Gln Asn Ser Ser Arg Thr Leu Glu Lys Asn Lys Lys
            420                 425                 430

Lys Gly Lys Ile Phe
        435
```

```
<210> SEQ ID NO 46
<211> LENGTH: 161
<212> TYPE: PRT
<213> ORGANISM: homo sapiens

<400> SEQUENCE: 46
```

```
Met Asn Leu Ala Ile Ser Ile Ala Leu Leu Thr Val Leu Gln Val
1               5                   10                  15

Ser Arg Gly Gln Lys Val Thr Ser Leu Thr Ala Cys Leu Val Asp Gln
                20                  25                  30

Ser Leu Arg Leu Asp Cys Arg His Glu Asn Thr Ser Ser Ser Pro Ile
            35                  40                  45

Gln Tyr Glu Phe Ser Leu Thr Arg Glu Thr Lys Lys His Val Leu Phe
        50                  55                  60

Gly Thr Val Gly Val Pro Glu His Thr Tyr Arg Ser Arg Thr Asn Phe
65                  70                  75                  80

Thr Ser Lys Tyr Asn Met Lys Val Leu Tyr Leu Ser Ala Phe Thr Ser
                85                  90                  95
```

```
Lys Asp Glu Gly Thr Tyr Thr Cys Ala Leu His His Ser Gly His Ser
            100             105                 110
Pro Pro Ile Ser Ser Gln Asn Val Thr Val Leu Arg Asp Lys Leu Val
        115             120                 125
Lys Cys Glu Gly Ile Ser Leu Leu Ala Gln Asn Thr Ser Trp Leu Leu
    130             135                 140
Leu Leu Leu Leu Ser Leu Ser Leu Leu Gln Ala Thr Asp Phe Met Ser
145             150             155                 160
Leu
```